(12) United States Patent
Tanaka et al.

(10) Patent No.: US 11,407,756 B2
(45) Date of Patent: Aug. 9, 2022

(54) HETEROCYCLIC COMPOUNDS AND NOXIOUS ARTHROPOD CONTROL AGENT CONTAINING SAME

(71) Applicant: SUMITOMO CHEMICAL COMPANY, LIMITED, Chuo-ku (JP)

(72) Inventors: Ayaka Tanaka, Chuo-ku (JP); Naoya Sugimoto, Takarazuka (JP); Risa Kono, Chuo-ku (JP); Yoshihiko Nokura, Takarazuka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 212 days.

(21) Appl. No.: 16/957,264

(22) PCT Filed: Dec. 25, 2018

(86) PCT No.: PCT/JP2018/047466
§ 371 (c)(1),
(2) Date: Jun. 23, 2020

(87) PCT Pub. No.: WO2019/131587
PCT Pub. Date: Jul. 4, 2019

(65) Prior Publication Data
US 2020/0399278 A1 Dec. 24, 2020

(30) Foreign Application Priority Data
Dec. 25, 2017 (JP) .............................. JP2017-247334

(51) Int. Cl.
*C07D 487/04* (2006.01)
*A01N 43/90* (2006.01)

(52) U.S. Cl.
CPC ........... *C07D 487/04* (2013.01); *A01N 43/90* (2013.01)

(58) Field of Classification Search
CPC ....... C07D 487/04; A01N 43/90; A01N 25/00
See application file for complete search history.

(56) References Cited

U.S. PATENT DOCUMENTS

2015/0191474 A1  7/2015  Takahashi et al.
2017/0226107 A1  8/2017  Cerezo-Galvez et al.
(Continued)

FOREIGN PATENT DOCUMENTS

EP   2 865 671 A1   4/2015
JP   2011-511080 A   4/2011
(Continued)

OTHER PUBLICATIONS

Extended European Search Report dated Aug. 8, 2021 in corresponding European Patent Application No. 18895706.2, 5 pages.
(Continued)

*Primary Examiner* — Andrew S Rosenthal
(74) *Attorney, Agent, or Firm* — Oblon, McClelland, Maier & Neustadt, L.L.P.

(57) ABSTRACT

A compound controlling harmful arthropods, represented by formula (I)

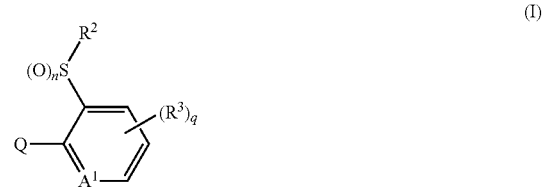

[wherein
Q represents a group represented by Q1 or a group represented by Q2;

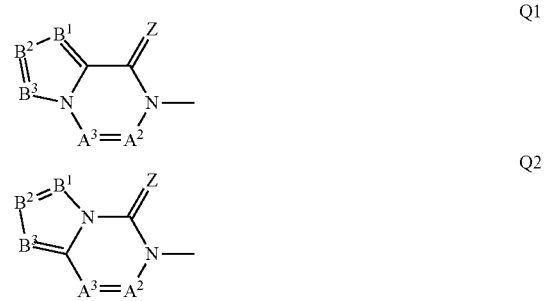

Z represents an oxygen atom or a sulfur atom;
$A^1$ represents a nitrogen atom;
$A^2$ represents a $CR^{4a}$;
$A^3$ represents a nitrogen atom or a $CR^{4b}$;
$B^1$ represents a $CR^1$;
$B^2$ represents a nitrogen atom or a $CR^{6b}$;
$B^3$ represents a nitrogen atom or a $CR^{6c}$;
$R^1$ represents a C1-C6 chain hydrocarbon group having one or more substituent(s) selected from the group consisting of a cyano group and a halogen atom;
$R^2$ represents a C1-C6 chain hydrocarbon group;
$R^3$ represents a C1-C6 chain hydrocarbon group;
$R^{4a}$, $R^{4b}$, $R^{6b}$, and $R^{6c}$ are identical to or different from each other, and each represent a hydrogen atom;
n represents 0, 1, or 2; and
q represents 0, 1, 2, or 3]
or an N-oxide compound thereof.

16 Claims, No Drawings

(56) References Cited

U.S. PATENT DOCUMENTS

2018/0271099 A1  9/2018  Fischer et al.
2018/0303097 A1  10/2018 Wilcke et al.
2019/0021329 A1  1/2019  Wilcke et al.

FOREIGN PATENT DOCUMENTS

| JP | 2017-509626 A | 4/2017 |
|---|---|---|
| WO | WO 2009/099929 A1 | 8/2009 |
| WO | WO 2011/017342 A2 | 2/2011 |
| WO | WO 2013/191112 A1 | 12/2013 |
| WO | WO 2015/135843 A1 | 9/2015 |
| WO | WO 2017/025419 A2 | 2/2017 |
| WO | WO 2017/055185 A1 | 4/2017 |
| WO | WO 2017/121674 A1 | 7/2017 |

OTHER PUBLICATIONS

International Search Report dated Mar. 26, 2019 in PCT/JP2018/047466 (submitting English translation only), 2 pages.
International Preliminary Report on Patentability and Written Opinion dated Jun. 30, 2020 in PCT/JP2018/047466 (submitting English translation only), 4 pages.
Indian Office Action dated Feb. 7, 2022 in Indian Patent Application No. 202047026442, 6 pages.

HETEROCYCLIC COMPOUNDS AND NOXIOUS ARTHROPOD CONTROL AGENT CONTAINING SAME

CROSS-REFERENCE TO RELATED APPLICATIONS

The present application is a 35 U.S.C. § 371 national stage patent application of International patent application PCT/JP2018/047466, filed on Dec. 25, 2018, which is based on and claims the benefits of priority to Japanese Application No. 2017-247334, filed on Dec. 25, 2017. The entire contents of these applications are incorporated herein by reference.

TECHNICAL FIELD

This application claims the priority to and the benefit of Japanese Patent Application No. 2017-247334 filed on Dec. 25, 2017, the entire contents of which are incorporated herein by reference.

The present invention relates to heterocyclic compounds and agents for controlling harmful arthropods comprising the same.

BACKGROUND ART

To date, various compounds have been studied in order to control harmful arthropods. For example, Patent Document 1 discloses that certain kinds of compound have control effects on pests.

CITATION LIST

Patent Document

Patent Document 1: WO 2013/191112 pamphlet

SUMMARY OF THE INVENTION

Problems to be Solved by Invention

An object of the present invention is to provide compounds having excellent control efficacy against harmful arthropods.

Means to Solve Problems

The present invention provides the followings.
[1] A compound represented by formula (I)

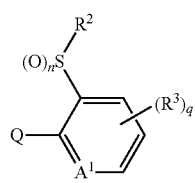

[wherein:
Q represents a group represented by Q1 or a group represented by Q2;

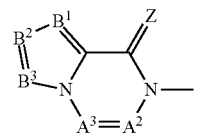

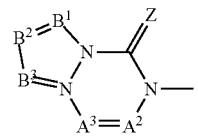

Z represents an oxygen atom or a sulfur atom;
$A^1$ represents a nitrogen atom or a $CR^5$;
$R^5$ represents a halogen atom or a hydrogen atom;
$A^2$ and $A^3$ represents a combination, which is
a combination wherein $A^2$ represents a $CR^{4a}$ and $A^3$ represents a nitrogen atom or a $CR^b$; or
a combination wherein $A^2$ represents a nitrogen atom and $A^3$ represents a $CR^{4b}$;
$B^1$, $B^2$, and $B^3$ represents a combination, which is
a combination wherein $B^1$ represents a $CR^1$, $B^2$ represents a nitrogen atom or a $CR^{6b}$, and $B^3$ represents a nitrogen atom or a $CR^{6c}$;
a combination wherein $B^1$ represents a nitrogen atom or a $CR^{6a}$, $B^2$ represents a $CR^1$, and $B^3$ represents a nitrogen atom or a $CR^{6c}$; or
a combination wherein $B^1$ represents a nitrogen atom or a $CR^{6a}$, $B^2$ represents a nitrogen atom or a $CR^{6b}$, and $B^3$ represents a $CR^1$;
$R^1$ represents a C1-C6 chain hydrocarbon group having one or more substituent(s) selected from the group consisting of a cyano group and a halogen atom, a C3-C4 cycloalkyl group optionally having one or more substituent(s) selected from the group consisting of a cyano group and a halogen atom, a —$SR^8$, a —$S(O)R^8$, a —$S(O)_2R^8$, a —$OR^8$, or a —$OS(O)_2R^8$;
$R^8$ represents a C1-C6 chain hydrocarbon group having one or more substituent(s) selected from the group consisting of a cyano group and a halogen atom, or a C3-C4 cycloalkyl group optionally having one or more substituent(s) selected from the group consisting of a cyano group and a halogen atom;
$R^{4a}$, $R^{4b}$, $R^{6a}$, $R^{6b}$, and $R^{6c}$ are identical to or different from each other, and each represent a C1-C6 chain hydrocarbon group optionally having one or more halogen atom(s), a C3-C7 cycloalkyl group optionally having one or more halogen atom(s), a C1-C6 alkoxy group optionally having one or more halogen atom(s), a —$NR^9R^{10}$, a —$C(O)R^7$, a —$C(O)OR^7$, a —$C(O)NR^{19}R^{20}$, a —$NR^9C(O)R^{10}$, a —$NR^9C(O)OR^{10}$, a —$NR^9C(O)NR^{19}R^{20}$, a cyano group, a halogen atom, or a hydrogen atom;
$R^9$ and $R^{19}$ are identical to or different from each other, and each represent a C1-C6 chain hydrocarbon group optionally having one or more halogen atom(s), or a hydrogen atom;
$R^{10}$ represents a C1-C6 chain hydrocarbon group optionally having one or more substituent(s) selected from Group F, a C3-C7 cycloalkyl group optionally having one or more substituent(s) selected from Group J, a C3-C7 cycloalkenyl group optionally having one or more substituent(s) selected from Group J, a phenyl group optionally having one or more substituent(s) selected from Group D, a 6 membered aromatic heterocyclic group optionally having one or more substituent(s) selected from Group D, a hydrogen atom, or a —S(O)$_2$R$^{21}$;

R$^{21}$ represents a C1-C6 chain hydrocarbon group optionally having one or more halogen atom(s), a C3-C7 cycloalkyl group optionally having one or more halogen atom(s), or a phenyl group optionally having one or more substituent(s) selected from Group D;

R$^7$, R$^{18}$, and R$^{20}$ are identical to or different from each other, and each represent a C1-C6 chain hydrocarbon group optionally having one or more substituent(s) selected from Group F, a C3-C7 cycloalkyl group optionally having one or more substituent(s) selected from Group J, or a hydrogen atom;

R$^2$ represents a C1-C6 chain hydrocarbon group optionally substituted with one or more halogen atom(s), a cyclopropyl group, or a cyclopropylmethyl group;

n represents 0, 1, or 2;

R$^3$ represents a C1-C6 chain hydrocarbon group optionally having one or more substituent(s) selected from Group B, a C3-C7 cycloalkyl group optionally having one or more substituent(s) selected from Group E, a C3-C7 cycloalkenyl group optionally having one or more substituent(s) selected from Group J, a phenyl group optionally having one or more substituent(s) selected from Group H, a 5 or 6 membered aromatic heterocyclic group optionally having one or more substituent(s) selected from Group H, a —OR$^{12}$, a —NR$^{11}$R$^{12}$, a —NR$^{11}$R$^{12a}$, a —NR$^{24}$NR$^{11}$R$^{12}$, a —NR$^{24}$OR$^{11}$, a —NR$^{11}$C(O)R$^{13}$, a —NR$^{24}$NR$^1$C(O)R$^{13}$, a —NR$^{11}$C(O)OR$^{14}$, a —NR$^{24}$NR$^{11}$C(O)OR$^{14}$, a —NR$^{11}$C(O)NR$^{15a}$R$^{16a}$, a —NR$^{24}$NR$^{11}$C(O)NR$^{15a}$R$^{16a}$, a —N=CR$^{24}$NR$^{15a}$R$^{16a}$, a —N=S(O)$_x$R$^{15}$R$^{16}$, a —C(O)R$^{13}$, a —C(O)OR$^{17}$, a —C(O)NR$^{15a}$R$^{16a}$, a —C(O)NR$^{11}$S(O)$_2$R$^{23}$, a —CR$^{24}$=NOR$^{17}$, a —NR$^{11}$CR$^{24}$=NOR$^{17}$, a cyano group, a nitro group, or a halogen atom;

q represents 0, 1, 2, or 3, wherein when q represents 2 or 3, two or three R$^3$ may be identical to or different from each other;

When two R$^3$ are adjacent with each other, the two R$^3$ may be combined with the two carbon atoms to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring {wherein said benzene ring, said pyrrole ring, said furan ring, said thiophene ring, said pyrazole ring, said imidazole ring, said triazole ring, said oxazole ring, said isoxazole ring, said thiazole ring, said pyridine ring, said pyridazine ring, said pyrimidine ring, and said pyrazine ring may optionally have one or more substituent(s) selected from Group H};

R$^{17}$ represents a C1-C6 chain hydrocarbon group optionally having one or more halogen atom(s), a phenyl group optionally having one or more substituent(s) selected from Group D, or a hydrogen atom;

R$^{11}$, R$^{15a}$, and R$^{24}$ are identical to or different from each other, and each represent a C1-C6 chain hydrocarbon group optionally having one or more halogen atom(s), or a hydrogen atom;

R$^{12}$ represents a C1-C6 chain hydrocarbon group optionally having one or more substituent(s) selected from Group F, a C3-C7 cycloalkyl group optionally having one or more substituent(s) selected from Group J, a C3-C7 cycloalkenyl group optionally having one or more substituent(s) selected from Group J, a phenyl group optionally having one or more substituent(s) selected from Group D, a 6 membered aromatic heterocyclic group optionally having one or more substituent(s) selected from Group D, a hydrogen atom, or a —S(O)$_2$R$^{23}$;

R$^{23}$ represents a C1-C6 chain hydrocarbon group optionally having one or more halogen atom(s), a C3-C7 cycloalkyl group optionally having one or more halogen atom(s), or a phenyl group optionally having one or more substituent(s) selected from Group D;

R$^{11a}$ and R$^{12a}$ may be combined with the nitrogen atom to which they are attached to form a 3-7 membered nonaromatic heterocyclic group optionally having one or more substituent(s) selected from Group E;

R$^{13}$ represents a C1-C6 chain hydrocarbon group optionally having one or more halogen atom(s), a C3-C7 cycloalkyl group optionally having one or more halogen atom(s), a (C3-C6 cycloalkyl)C1-C3 alkyl group optionally having one or more halogen atom(s), a phenyl group optionally having one or more substituent(s) selected from Group D, a 5 or 6 membered aromatic heterocyclic group optionally having one or more substituent(s) selected from Group D, or a hydrogen atom;

R$^{14}$ represents a C1-C6 chain hydrocarbon group optionally having one or more halogen atom(s), a C3-C7 cycloalkyl group optionally having one or more halogen atom(s), a (C3-C6 cycloalkyl)C1-C3 alkyl group optionally having one or more halogen atom(s), or a (phenyl optionally having one or more substituent(s) selected from Group D)C1-C3 alkyl group;

R$^{15}$ and R$^{16}$ are identical to or different from each other, and each represent a C1-C6 alkyl group optionally having one or more halogen atom(s);

R$^{16a}$ represents a C1-C6 chain hydrocarbon group optionally having one or more substituent(s) selected from Group F, a C3-C7 cycloalkyl group optionally having one or more substituent(s) selected from Group J, or a hydrogen atom; and x represents 0 or 1;

Group B: a group consisting of a C1-C6 alkoxy group optionally having one or more halogen atom(s), a C3-C6 alkenyloxy group optionally having one or more halogen atom(s), a C3-C6 alkynyloxy group optionally having one or more halogen atom(s), a C1-C6 alkylsulfanyl group optionally having one or more halogen atom(s), a C1-C6 alkylsulfinyl group optionally having one or more halogen atom(s), a C1-C6 alkylsulfonyl group optionally having one or more halogen atom(s), a C3-C6 cycloalkyl group optionally having one or more halogen atom(s), a (C1-C6 alkyl optionally having one or more halogen atom(s))amino group, a di(C1-C4 alkyl)amino group optionally having one or more halogen atom(s), a C2-C6 alkylcarbonyl group optionally having one or more halogen atom(s), a C2-C6 alkoxycarbonyl group optionally having one or more halogen atom(s), a C2-C6 alkoxycarbonyloxy group optionally having one or more halogen atom(s), an aminocarbonyl group, a (C1-C6 alkyl optionally having one or more halogen atom(s))aminocarbonyl group, a (di(C1-C4 alkyl)amino optionally having one or more halogen atom(s))carbonyl group, a (C2-C6 alkoxycarbonyl optionally having one or more halogen atom(s))amino group, a (C2-C6 alkoxycarbonyl)(C1-C6 alkyl)amino group optionally having one or more halogen atom(s), a cyano group, an amino group, a nitro group, a hydroxy group, and a halogen atom;

Group D: a group consisting of a C1-C6 chain hydrocarbon group optionally having one or more halogen atom(s), a C1-C6 alkoxy group optionally having one or more halogen atom(s), a C3-C6 alkenyloxy group optionally having one or more halogen atom(s), a C3-C6 alkynyloxy group optionally having one or more halogen atom(s), a C1-C6 alkylsulfanyl group optionally having one or more halogen atom(s), a C1-C6 alkylsulfinyl group optionally having one or more halogen atom(s), a C1-C6 alkylsulfonyl group optionally having one or more halogen atom(s), a C3-C6 cycloalkyl group optionally having one or more halogen atom(s), a (C1-C6 alkyl optionally having one or more halogen atom(s))amino group, a di(C1-C4 alkyl)amino group optionally having one or more halogen atom(s), a C2-C6 alkylcarbonyl group optionally having one or more halogen atom(s), a C2-C6 alkoxycarbonyl group optionally having one or more halogen atom(s), a C2-C6 alkoxycarbonyloxy group optionally having one or more halogen atom(s), an aminocarbonyl group, a (C1-C6 alkyl optionally having one or more halogen atom(s))aminocarbonyl group, a (di(C1-C4 alkyl)amino optionally having one or more halogen atom(s))carbonyl group, a (C2-C6 alkoxycarbonyl optionally having one or more halogen atom(s))amino group, a (C2-C6 alkoxycarbonyl)(C1-C6 alkyl)amino group optionally having one or more halogen atom(s), a cyano group, an amino group, a nitro group, a hydroxy group, and a halogen atom;

Group E: a group consisting of a C1-C6 chain hydrocarbon group optionally having one or more halogen atom(s), a C1-C6 alkoxy group optionally having one or more halogen atom(s), a C3-C6 alkenyloxy group optionally having one or more halogen atom(s), a C3-C6 alkynyloxy group optionally having one or more halogen atom(s), a (C1-C6 alkyl optionally having one or more halogen atom(s))amino group, a di(C1-C4 alkyl)amino group optionally having one or more halogen atom(s), a C2-C6 alkylcarbonyl group optionally having one or more halogen atom(s), a C2-C6 alkoxycarbonyl group optionally having one or more halogen atom(s), a C2-C6 alkoxycarbonyloxy group optionally having one or more halogen atom(s), an aminocarbonyl group, a (C1-C6 alkyl optionally having one or more halogen atom(s))aminocarbonyl group, a (di(C1-C4 alkyl)amino optionally having one or more halogen atom(s))carbonyl group, a (C2-C6 alkoxycarbonyl optionally having one or more halogen atom(s))amino group, a (C2-C6 alkoxycarbonyl)(C1-C6 alkyl)amino group optionally having one or more halogen atom(s), a cyano group, an amino group, a nitro group, a hydroxy group, an oxo group, and a halogen atom;

Group F: a group consisting of a C3-C6 cycloalkyl group optionally having one or more halogen atom(s), a phenyl group optionally having one or more substituent(s) selected from Group D, a 5 or 6 membered aromatic heterocyclic group optionally having one or more substituent(s) selected from Group D, a C1-C6 alkoxy group optionally having one or more halogen atom(s), a (C1-C6 alkyl optionally having one or more halogen atom(s))amino group, a di(C1-C4 alkyl)amino group optionally having one or more halogen atom(s), a cyano group, an amino group, a nitro group, a hydroxy group, and a halogen atom;

Group H: a group consisting of a C1-C6 chain hydrocarbon group optionally having one or more halogen atom(s), a C3-C6 cycloalkyl group optionally having one or more halogen atom(s), a phenyl group optionally having one or more substituent(s) selected from Group D, a 5 or 6 membered aromatic heterocyclic group optionally having one or more substituent(s) selected from Group D, a C1-C6 alkoxy group optionally having one or more halogen atom(s), a (C1-C6 alkyl optionally having one or more halogen atom(s))amino group, a di(C1-C4 alkyl)amino group optionally having one or more halogen atom(s), a C2-C6 alkylcarbonyl group optionally having one or more halogen atom(s), a C2-C6 alkoxycarbonyl group optionally having one or more halogen atom(s), a C2-C6 alkoxycarbonyloxy group optionally having one or more halogen atom(s), an aminocarbonyl group, a (C1-C6 alkyl optionally having one or more halogen atom(s))aminocarbonyl group, a (di(C1-C4 alkyl)amino optionally having one or more halogen atom(s))carbonyl group, a (C2-C6 alkoxycarbonyl optionally having one or more halogen atom(s))amino group, a (C2-C6 alkoxycarbonyl)(C1-C6 alkyl)amino group optionally having one or more halogen atom(s), a cyano group, an amino group, a nitro group, a hydroxy group, and a halogen atom;

Group J: a group consisting of a C1-C6 alkyl group optionally having one or more halogen atom(s), a C1-C6 alkoxy group optionally having one or more halogen atom(s), a C2-C6 alkoxycarbonyl group optionally having one or more halogen atom(s), an amino group, a cyano group, and a halogen atom]

or an N-oxide compound thereof (hereinafter the compound represented by formula (I) or N-oxide compound thereof is referred to as "Present compound X").

[2] The compound represented by formula (I) according to [1] (hereinafter referred to as "Present compound").

[3] The compound according to [1] or [2], wherein $A^1$ represents a CH.

[4] The compound according to [1] or [2], wherein $A^1$ represents a nitrogen atom.

[5] The compound according to any one of [1] to [4], wherein Q represents the group represented by Q1.

[6] The compound according to any one of [1] to [4], wherein Q represents the group represented by Q2.

[7] The compound according to any one of [1] to [6], wherein $R^1$ represents a C1-C6 alkyl group having one or more substituent(s) selected from the group consisting of a cyano group and a halogen atom, a cyclopropyl group optionally having one or more substituent(s) selected from the group consisting of a cyano group and a halogen atom, or a —OS(O)$_2$R$^8$.

[8] The compound according to any one of [1] to [7], wherein $R^3$ represents a C1-C6 alkyl group optionally having one or more substituent(s) selected from Group B, a C3-C7 cycloalkyl group optionally having one or more substituent(s) selected from Group E, a phenyl group optionally having one or more substituent(s) selected from Group J, a 5 membered aromatic heterocyclic group comprising 1 to 4 nitrogen atom(s) optionally having one or more substituent(s) selected from Group J, a 6 membered aromatic heterocyclic group optionally having one or more substituent(s) selected from Group J, a —OR$^{12}$, a —NR$^{11}$R$^{12}$, a —NR$^{11}$C(O)OR$^{14}$, or a halogen atom.

[9] The compound according to any one of [1] to [8], wherein $R^2$ represents an ethyl group.

[10] The compound according to any one of [1] to [9], wherein Z represents an oxygen atom.

[11] A composition for controlling a harmful arthropod comprising the compound according to any one of [1] to [10] and an inert carrier.

[12] A method for controlling a harmful arthropod which comprises applying an effective amount of the compound according to any one of [1] to [10] to a harmful arthropod or a habitat where a harmful arthropod lives.

[13] A composition comprising one or more ingredient(s) selected from the group consisting of Group (a) and Group (b), and the compound according to any one of [1] to [10]:

Group (a): a group consisting of insecticidal active ingredients, miticidal active ingredients, and nematicidal active ingredients;

Group (b): fungicidal active ingredients.

[14] A method for controlling a harmful arthropod which comprises applying an effective amount of the composition according to [13] to a harmful arthropod or a habitat where a harmful arthropod lives.
[15] A seed or a vegetative reproduction organ holding an effective amount of the compound according to any one of [1] to [10] or an effective amount of the composition according to [13].

Effect of Invention

According to the present invention, harmful arthropods can be controlled.

MODE FOR CARRYING OUT THE INVENTION

The substituents in the present invention are explained as follows.

The term of "halogen atom" represents a fluorine atom, a chlorine atom, a bromine atom, or an iodine atom.

When a substituent has two or more halogen atoms, these halogen atoms may be identical to or different from each other.

When a substituent has two or more substituents selected from a specific group (for example, a group consisting of a cyano group and a halogen atom), these substituents may be identical to or different from each other.

When a group "optionally having one or more substituent(s) selected from Group X" (wherein X represents any one of B, D, E, F, H, and J) as described herein has two or more substituents selected from Group X, these substituents may be identical to or different from each other.

The expression of "CX—CY" as described herein means that the number of carbon atom is X to Y. For example, the expression of "C1-C6" means that the number of carbon atom is 1 to 6.

The term of "chain hydrocarbon group" represents an alkyl group, an alkenyl group, or an alkynyl group.

Examples of the term of "alkyl group" include a methyl group, an ethyl group, a propyl group, an isopropyl group, a 1,1-dimethylpropyl group, a 1,2-dimethylpropyl group, a butyl group, a tert-butyl group, a pentyl group, and a hexyl group.

Examples of the term of "alkenyl group" include a vinyl group, a 1-propenyl group, a 2-propenyl group, a 1-methyl-1-propenyl group, a 1-methyl-2-propenyl group, a 1,2-dimethyl-1-propenyl group, a 3-butenyl group, a 4-pentenyl group, and a 5-hexenyl group.

Examples of the term of "alkynyl group" include an ethinyl group, a 1-propynyl group, a 2-propynyl group, a 1-methyl-2-propynyl group, a 1,1-dimethyl-2-propynyl group, a 2-butynyl group, a 4-pentynyl group, and a 5-hexynyl group.

The term of "C1-C3 perfluoroalkyl group" represents a trifluoromethyl group, a pentafluoroethyl group, a heptafluoropropyl group, or a heptafluoroisopropyl group.

The term of "C1-C2 perfluoroalkyl group" represents a trifluoromethyl group or a pentafluoroethyl group.

The term of "C1-C3 alkoxy group" represents a methoxy group, an ethoxy group, a propoxy group, or an isopropoxy group.

Examples of the term of "cycloalkyl group" include a cyclopropyl group, a cyclobutyl group, a cyclopentyl group, a cyclohexyl group, and a cycloheptyl group.

Examples of the term of "cycloalkenyl group" include a cyclopropenyl group, a cyclobutenyl group, a cyclopentenyl group, a cyclohexenyl group, and a cycloheptenyl group.

The term of "3-7 membered nonaromatic heterocyclic group" represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring. Examples of the 3-7 membered nonaromatic heterocyclic group optionally having one or more substituent(s) selected from Group E include the following groups.

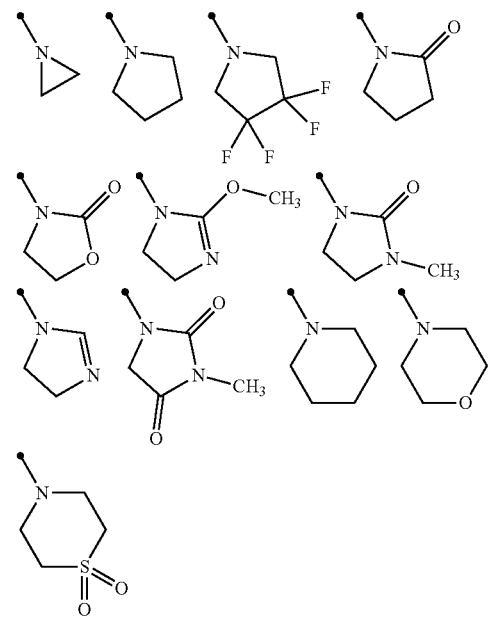

The term of "5 or 6 membered aromatic heterocyclic group" represents a 5 membered aromatic heterocyclic group or a 6 membered aromatic heterocyclic group, and the term of "5 membered aromatic heterocyclic group" represents a pyrrolyl group, a furyl group, a thienyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, or a thiadiazolyl group. The term of "5 membered aromatic heterocyclic group comprising 1 to 4 nitrogen atom(s)" represents a pyrrolyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, or a thiadiazolyl group. The term of "6 membered aromatic heterocyclic group represents a pyridyl group, a pyridazinyl group, a pyrimidinyl group, a pyrazinyl group, a triazinyl group, or a tetrazinyl group.

The term of "(C3-C6 cycloalkyl)C1-C3 alkyl group optionally having one or more halogen atom(s)" means that the (C3-C6 cycloalkyl) moiety and/or the (C1-C3 alkyl) moiety may optionally have one or more halogen atom(s), and examples thereof include a cyclopropylmethyl group, a (2-fluorocyclopropyl)methyl group, a cyclopropyl(fluoro)methyl group, and a (2-fluorocyclopropyl)(fluoro)methyl group.

The term of "(C2-C6 alkoxycarbonyl)(C1-C6 alkyl) amino group optionally having one or more halogen atom(s)" means that the (C2-C6 alkoxycarbonyl) moiety and/or the (C1-C6 alkyl) moiety may optionally have one or more halogen atom(s), and examples thereof include a (2-fluoroethoxycarbonyl)(methyl)amino group, a (methoxycarbonyl)(2-fluoroethyl)amino group, and a (2-fluoroethoxycarbonyl)(2-fluoroethyl)amino group.

The Present compound X may optionally have one or more stereoisomer(s). Examples of the stereoisomer(s) include enantiomers, diastereomers, and geometric isomers. The present invention encompasses each stereoisomer and mixtures of stereoisomers at any ratio.

The Present compound X may optionally form an acid addition salt. Examples of the acid to form the acid addition salt include inorganic acids such as hydrogen chloride, phosphoric acid, and sulfuric acid; and organic acids such as acetic acid, trifluoroacetic acid, benzoic acid, and p-toluenesulfonic acid. Such acid addition salt may be prepared by mixing the Present compound X with an acid.

Embodiments of the Present compound include the following compounds.

[Embodiment 1] The Present compound, wherein
Z represents an oxygen atom;
$R^2$ represents a C1-C6 alkyl group optionally substituted with one or more halogen atom(s);
$A^1$ represents a nitrogen atom or a CH; and
$R^{4a}$ and $R^{4b}$ each represent a hydrogen atom.

[Embodiment 2] The Present compound, wherein
Z represents an oxygen atom;
$R^2$ represents an ethyl group;
$A^1$ represents a nitrogen atom or a CH; and
$R^{4a}$ and $R^{4b}$ each represent a hydrogen atom.

[Embodiment 3] The compound according to Embodiment 2, wherein n represents 2.

[Embodiment 4] The Present compound, wherein
Z represents an oxygen atom;
$R^2$ represents an ethyl group;
$A^1$ represents a nitrogen atom;
$A^2$ and $A^3$ each represent a CH;
n represents 2; and
q represents 0 or 1.

[Embodiment 5] The compound according to Embodiment 4, wherein
$R^3$ represents a C1-C6 chain hydrocarbon group optionally having one or more substituent(s) selected from Group B, a C3-C7 cycloalkyl group optionally having one or more substituent(s) selected from Group E, a phenyl group optionally having one or more substituent(s) selected from Group H, a 5 or 6 membered aromatic heterocyclic group optionally having one or more substituent(s) selected from Group H, a —$OR^{12}$, a —$NR^{11}R^{12}$, a —$NR^{11}C(O)OR^{14}$, a —$NR^{11}C(O)NR^{15a}R^{16a}$, a —$C(O)OR^{17}$, a —$C(O)NR^{15a}R^{16a}$, a cyano group, a nitro group, or a halogen atom.

[Embodiment 6] The compound according to Embodiment 4, wherein
$R^3$ represents a C1-C6 alkyl group optionally having one or more halogen atom(s), a cyclopropyl group optionally having a cyano group, a phenyl group optionally having one or more substituent(s) selected from Group J, a 5 or 6 membered aromatic heterocyclic group optionally having one or more substituent(s) selected from Group J, a —$OR^{12}$, a —$NR^{11}R^{12}$, a —$NR^{11}C(O)OR^{14}$, a —$NR^{11}C(O)NR^{15a}R^{16a}$, a —$C(O)OR^{17}$, a —$C(O)NR^{15a}R^{16a}$, or a halogen atom.

[Embodiment 7] The compound according to Embodiment 4, wherein
$R^3$ represents a phenyl group optionally having one or more substituent(s) selected from the group consisting of a cyano group and a halogen atom, a cyclopropyl group optionally having a cyano group, a trifluoromethyl group, or a halogen atom.

[Embodiment 8] The compound according to any one of Embodiments 1 to 7, wherein
$B^1$ represents a nitrogen atom or a $CR^{6a}$;
the combination of $B^2$ and $B^3$ represents
a combination wherein $B^2$ represents a $CR^1$ and $B^3$ represents a nitrogen atom or a $CR^{6c}$; or
a combination wherein $B^2$ represents a nitrogen atom or a $CR^{6b}$ and $B^3$ represents a $CR^1$;
$R^1$ represents a C1-C3 perfluoroalkyl group, a 1-cyanocyclopropyl group, or a 1-cyano-1-methylethyl group; and
$R^{6a}$, $R^{6b}$, and $R^{6c}$ are identical to or different from each other, and each represent a C1-C3 alkyl group optionally having one or more halogen atom(s), a halogen atom, or a hydrogen atom.

[Embodiment 9] The compound according to any one of Embodiments 1 to 7, wherein
$B^1$ represents a nitrogen atom or a $CR^{6a}$;
the combination of $B^2$ and $B^3$ represents
a combination wherein $B^2$ represents a $CR^1$ and $B^3$ represents a nitrogen atom; or
a combination wherein $B^2$ represents a nitrogen atom and $B^3$ represents a $CR^1$;
$R^1$ represents a C1-C3 perfluoroalkyl group, a 1-cyanocyclopropyl group, or a 1-cyano-1-methylethyl group; and
$R^{6a}$ represents a C1-C3 alkyl group optionally having one or more halogen atom(s), a halogen atom, or a hydrogen atom.

[Embodiment 10] The compound according to any one of Embodiments 1 to 7, wherein
$B^1$ represents a nitrogen atom or a $CR^{6a}$;
the combination of $B^2$ and $B^3$ represents
a combination wherein $B^2$ represents a $CR^1$ and $B^3$ represents a nitrogen atom or a $CR^{6c}$; or
a combination wherein $B^2$ represents a nitrogen atom or a $CR^{6b}$ and $B^3$ represents a $CR^1$;
$R^1$ represents a C1-C2 perfluoroalkyl group; and
$R^{6a}$, $R^{6b}$, and $R^{6c}$ are identical to or different from each other, and each represent a C1-C3 alkyl group optionally having one or more halogen atom(s), a halogen atom, or a hydrogen atom.

[Embodiment 11] The compound according to any one of Embodiments 1 to 7, wherein
$B^1$ represents a nitrogen atom;
the combination of $B^2$ and $B^3$ represents
a combination wherein $B^2$ represents a $CR^1$ and $B^3$ represents a nitrogen atom; or
a combination wherein $B^2$ represents a nitrogen atom and $B^3$ represents a $CR^1$; and
$R^1$ represents a C1-C2 perfluoroalkyl group. [Embodiment 12] The compound according to any one of Embodiments 1 to 7, wherein
$B^1$ represents a nitrogen atom;
the combination of $B^2$ and $B^3$ represents
a combination wherein $B^2$ represents a $CR^1$ and $B^3$ represents a CH; or
a combination wherein $B^2$ represents a CH and $B^3$ represents a $CR^1$; and
$R^1$ represents a C1-C2 perfluoroalkyl group.

[Embodiment 13] The compound according to any one of Embodiments 1 to 7, wherein
$B^1$ represents a CH;
the combination of $B^2$ and $B^3$ represents
a combination wherein $B^2$ represents a $CR^1$ and $B^3$ represents a nitrogen atom; or a combination wherein $B^2$ represents a nitrogen atom and $B^3$ represents a $CR^1$; and
$R^1$ represents a C1-C2 perfluoroalkyl group.

[Embodiment 14] The compound according to any one of Embodiments 1 to 7, wherein
$B^1$ represents a CH;
the combination of $B^2$ and $B^3$ represents
a combination wherein $B^2$ represents a $CR^1$ and $B^3$ represents a CH; or
a combination wherein $B^2$ represents a CH and $B^3$ represents a $CR^1$; and
$R^1$ represents a C1-C2 perfluoroalkyl group.

[Embodiment 15] The compound according to any one of Embodiments 1 to 7, wherein
Q represents the group represented by Q1;
$B^1$ represents a nitrogen atom or a $CR^{6a}$;
the combination of $B^2$ and $B^3$ represents
a combination wherein $B^2$ represents a $CR^1$ and $B^3$ represents a nitrogen atom or a $CR^{6c}$; or
a combination wherein $B^2$ represents a nitrogen atom or a $CR^{6b}$ and $B^3$ represents a $CR^1$;
$R^1$ represents a C1-C3 perfluoroalkyl group, a 1-cyanocyclopropyl group, or a 1-cyano-1-methylethyl group; and
$R^{6a}$, $R^{6b}$, and $R^{6c}$ are identical to or different from each other, and each represent a C1-C3 alkyl group optionally having one or more halogen atom(s), a halogen atom, or a hydrogen atom.

[Embodiment 16] The compound according to any one of Embodiments 1 to 7, wherein
Q represents the group represented by Q1;
$B^1$ represents a nitrogen atom or a $CR^{6a}$;
the combination of $B^2$ and $B^3$ represents
a combination wherein $B^2$ represents a $CR^1$ and $B^3$ represents a nitrogen atom; or
a combination wherein $B^2$ represents a nitrogen atom and $B^3$ represents a $CR^1$;
$R^1$ represents a C1-C3 perfluoroalkyl group, a 1-cyanocyclopropyl group, or a 1-cyano-1-methylethyl group; and
$R^{6a}$ represents a C1-C3 alkyl group optionally having one or more halogen atom(s), a halogen atom, or a hydrogen atom.

[Embodiment 17] The compound according to any one of Embodiments 1 to 7, wherein
Q represents the group represented by Q1;
$B^1$ represents a nitrogen atom or a $CR^{6a}$;
the combination of $B^2$ and $B^3$ represents
a combination wherein $B^2$ represents a $CR^1$ and $B^3$ represents a nitrogen atom or a $CR^{6c}$; or
a combination wherein $B^2$ represents a nitrogen atom or a $CR^{6b}$ and $B^3$ represents a $CR^1$;
$R^1$ represents a C1-C2 perfluoroalkyl group; and
$R^{6a}$, $R^{6b}$, and $R^{6c}$ are identical to or different from each other, and each represent a C1-C3 alkyl group optionally having one or more halogen atom(s), a halogen atom, or a hydrogen atom.

[Embodiment 18] The compound according to any one of Embodiments 1 to 7, wherein
Q represents the group represented by Q1;
$B^1$ represents a nitrogen atom;
the combination of $B^2$ and $B^3$ represents
a combination wherein $B^2$ represents a $CR^1$ and $B^3$ represents a nitrogen atom; or
a combination wherein $B^2$ represents a nitrogen atom and $B^3$ represents a $CR^1$; and
$R^1$ represents a C1-C2 perfluoroalkyl group.

[Embodiment 19] The compound according to any one of Embodiments 1 to 7, wherein
Q represents the group represented by Q1;
$B^1$ represents a nitrogen atom;
the combination of $B^2$ and $B^3$ represents
a combination wherein $B^2$ represents a $CR^1$ and $B^3$ represents a CH; or
a combination wherein $B^2$ represents a CH and $B^3$ represents a $CR^1$; and
$R^1$ represents a C1-C2 perfluoroalkyl group.

[Embodiment 20] The compound according to any one of Embodiments 1 to 7, wherein
Q represents the group represented by Q1;
$B^1$ represents a CH;
the combination of $B^2$ and $B^3$ represents
a combination wherein $B^2$ represents a $CR^1$ and $B^3$ represents a nitrogen atom; or
a combination wherein $B^2$ represents a nitrogen atom and $B^3$ represents a $CR^1$; and
$R^1$ represents a C1-C2 perfluoroalkyl group.

[Embodiment 21] The compound according to any one of Embodiments 1 to 7, wherein
Q represents the group represented by Q1;
$B^1$ represents a CH;
the combination of $B^2$ and $B^3$ represents
a combination wherein $B^2$ represents a $CR^1$ and $B^3$ represents a CH; or
a combination wherein $B^2$ represents a CH and $B^3$ represents a $CR^1$; and
$R^1$ represents a C1-C2 perfluoroalkyl group.

[Embodiment 22] The compound according to any one of Embodiments 1 to 7, wherein
Q represents the group represented by Q2;
$B^1$ represents a nitrogen atom or a $CR^{6a}$;
the combination of $B^2$ and $B^3$ represents
a combination wherein $B^2$ represents a $CR^1$ and $B^3$ represents a nitrogen atom or a $CR^{6c}$; or
a combination wherein $B^2$ represents a nitrogen atom or a $CR^{6b}$ and $B^3$ represents a $CR^1$;
$R^1$ represents a C1-C3 perfluoroalkyl group, a 1-cyanocyclopropyl group, or a 1-cyano-1-methylethyl group; and
$R^{6a}$, $R^{6b}$, and $R^{6c}$ are identical to or different from each other, and each represent a C1-C3 alkyl group optionally having one or more halogen atom(s), a halogen atom, or a hydrogen atom.

[Embodiment 23] The compound according to any one of Embodiments 1 to 7, wherein
Q represents the group represented by Q2;
$B^1$ represents a nitrogen atom or a $CR^{6a}$;
the combination of $B^2$ and $B^3$ represents
a combination wherein $B^2$ represents a $CR^1$ and $B^3$ represents a nitrogen atom; or
a combination wherein $B^2$ represents a nitrogen atom and $B^3$ represents a $CR^1$;
$R^1$ represents a C1-C3 perfluoroalkyl group, a 1-cyanocyclopropyl group, or a 1-cyano-1-methylethyl group; and
$R^{6a}$ represents a C1-C3 alkyl group optionally having one or more halogen atom(s), a halogen atom, or a hydrogen atom.

[Embodiment 24] The compound according to any one of Embodiments 1 to 7, wherein
Q represents the group represented by Q2;
$B^1$ represents a nitrogen atom or a $CR^{6a}$;
the combination of $B^2$ and $B^3$ represents
a combination wherein $B^2$ represents a $CR^1$ and $B^3$ represents a nitrogen atom or a $CR^{6c}$; or
a combination wherein $B^2$ represents a nitrogen atom or a $CR^{6b}$ and $B^3$ represents a $CR^1$;
$R^1$ represents a C1-C2 perfluoroalkyl group; and $R^{6a}$, $R^{6b}$, and $R^{6c}$ are identical to or different from each other, and each represent a C1-C3 alkyl group optionally having one or more halogen atom(s), a halogen atom, or a hydrogen atom.

[Embodiment 25] The compound according to any one of Embodiments 1 to 7, wherein
Q represents the group represented by Q2;
$B^1$ represents a nitrogen atom:
the combination of $B^2$ and $B^3$ represents
a combination wherein $B^2$ represents a $CR^1$ and $B^3$ represents a nitrogen atom; or
a combination wherein $B^2$ represents a nitrogen atom and $B^3$ represents a $CR^1$; and
$R^1$ represents a C1-C2 perfluoroalkyl group.

[Embodiment 26] The compound according to any one of Embodiments 1 to 7, wherein
Q represents the group represented by Q2;
$B^1$ represents a nitrogen atom;
the combination of $B^2$ and $B^3$ represents
a combination wherein $B^2$ represents a $CR^1$ and $B^3$ represents a CH; or
a combination wherein $B^2$ represents a CH and $B^3$ represents a $CR^1$; and
$R^1$ represents a C1-C2 perfluoroalkyl group.

[Embodiment 27] The compound according to any one of Embodiments 1 to 7, wherein
Q represents the group represented by Q2;
$B^1$ represents a CH;
the combination of $B^2$ and $B^3$ represents
a combination wherein $B^2$ represents a $CR^1$ and $B^3$ represents a nitrogen atom; or
a combination wherein $B^2$ represents a nitrogen atom and $B^3$ represents a $CR^1$; and
$R^1$ represents a C1-C2 perfluoroalkyl group.

[Embodiment 28] The compound according to any one of Embodiments 1 to 7, wherein
Q represents the group represented by Q2;
$B^1$ represents a CH;
the combination of $B^2$ and $B^3$ represents
a combination wherein $B^2$ represents a $CR^1$ and $B^3$ represents a CH; or
a combination wherein $B^2$ represents a CH and $B^3$ represents a $CR^1$; and
$R^1$ represents a C1-C2 perfluoroalkyl group.

[Embodiment 29] The compound according to any one of Embodiments 1 to 7, wherein
$B^1$ represents a nitrogen atom or a $CR^{6a}$;
$B^2$ represents a $CR^1$;
$B^3$ represents a nitrogen atom or a $CR^{6c}$;
$R^1$ represents a C1-C3 perfluoroalkyl group, a 1-cyanocyclopropyl group, or a 1-cyano-1-methylethyl group; and
$R^{6a}$ and $R^{6c}$ are identical to or different from each other, and each represent a C1-C3 alkyl group optionally having one or more halogen atom(s), a halogen atom, or a hydrogen atom.

[Embodiment 30] The compound according to any one of Embodiments 1 to 7, wherein
$B^1$ represents a nitrogen atom or a $CR^{6a}$;
$B^2$ represents a $CR^1$;
$B^3$ represents a nitrogen atom;
$R^1$ represents a C1-C3 perfluoroalkyl group, a 1-cyanocyclopropyl group, or a 1-cyano-1-methylethyl group; and
$R^{6a}$ represents a C1-C3 alkyl group optionally having one or more halogen atom(s), a halogen atom, or a hydrogen atom.

[Embodiment 31] The compound according to any one of Embodiments 1 to 7, wherein
$B^1$ represents a nitrogen atom or a $CR^{6a}$;
$B^2$ represents a $CR^1$;
$B^3$ represents a $CR^{6c}$;
$R^1$ represents a C1-C3 perfluoroalkyl group, a 1-cyanocyclopropyl group, or a 1-cyano-1-methylethyl group; and
$R^{6a}$ and $R^{6c}$ are identical to or different from each other, and each represent a C1-C3 alkyl group optionally having one or more halogen atom(s), a halogen atom, or a hydrogen atom.

[Embodiment 32] The compound according to any one of Embodiments 1 to 7, wherein
$B^1$ represents a nitrogen atom or a $CR^{6a}$;
$B^2$ represents a $CR^1$;
$B^3$ represents a nitrogen atom or a $CR^{6c}$;
$R^1$ represents a C1-C2 perfluoroalkyl group; and
$R^{6a}$ and $R^{6c}$ are identical to or different from each other, and each represent a C1-C3 alkyl group optionally having one or more halogen atom(s), a halogen atom, or a hydrogen atom.

[Embodiment 33] The compound according to any one of Embodiments 1 to 7, wherein
$B^1$ represents a nitrogen atom or a $CR^{6a}$;
$B^2$ represents a $CR^1$;
$B^3$ represents a nitrogen atom;
$R^1$ represents a C1-C2 perfluoroalkyl group; and
$R^{6a}$ represents a C1-C3 alkyl group optionally having one or more halogen atom(s), a halogen atom, or a hydrogen atom.

[Embodiment 34] The compound according to any one of Embodiments 1 to 7, wherein
$B^1$ represents a nitrogen atom or a $CR^{6a}$;
$B^2$ represents a $CR^1$;
$B^3$ represents a $CR^{6c}$;
$R^1$ represents a C1-C2 perfluoroalkyl group; and
$R^{6a}$ and $R^{6c}$ are identical to or different from each other, and each represent a C1-C3 alkyl group optionally having one or more halogen atom(s), a halogen atom, or a hydrogen atom.

[Embodiment 35] The compound according to any one of Embodiments 1 to 7, wherein
$B^1$ represents a nitrogen atom;
$B^2$ represents a $CR^1$;
$B^3$ represents a nitrogen atom; and
$R^1$ represents a C1-C2 perfluoroalkyl group.

[Embodiment 36] The compound according to any one of Embodiments 1 to 7, wherein
$B^1$ represents a nitrogen atom;
$B^2$ represents a $CR^1$;
$B^3$ represents a CH; and
$R^1$ represents a C1-C2 perfluoroalkyl group.

[Embodiment 37] The compound according to any one of Embodiments 1 to 7, wherein
$B^1$ represents a CH;
$B^2$ represents a $CR^1$;
$B^3$ represents a nitrogen atom; and
$R^1$ represents a C1-C2 perfluoroalkyl group.

[Embodiment 38] The compound according to any one of Embodiments 1 to 7, wherein
$B^1$ represents a CH;
$B^2$ represents a $CR^1$;
$B^3$ represents a CH; and
$R^1$ represents a C1-C2 perfluoroalkyl group.

[Embodiment 39] The compound according to any one of Embodiments 1 to 7, wherein
Q represents the group represented by Q1;
$B^1$ represents a nitrogen atom or a $CR^{6a}$;
$B^2$ represents a $CR^1$;

B³ represents a nitrogen atom or a CR$^{6c}$;
R¹ represents a C1-C3 perfluoroalkyl group, a 1-cyanocyclopropyl group, or a 1-cyano-1-methylethyl group; and
R$^{6a}$ and R$^{6c}$ are identical to or different from each other, and each represent a C1-C3 alkyl group optionally having one or more halogen atom(s), a halogen atom, or a hydrogen atom.

[Embodiment 40] The compound according to any one of Embodiments 1 to 7, wherein
Q represents the group represented by Q1;
B¹ represents a nitrogen atom or a CR$^{6a}$;
B² represents a CR¹;
B³ represents a nitrogen atom;
R¹ represents a C1-C3 perfluoroalkyl group, a 1-cyanocyclopropyl group, or a 1-cyano-1-methylethyl group; and
R$^{6a}$ represents a C1-C3 alkyl group optionally having one or more halogen atom(s), a halogen atom, or a hydrogen atom.

[Embodiment 41] The compound according to any one of Embodiments 1 to 7, wherein
Q represents the group represented by Q1;
B¹ represents a nitrogen atom or a CR$^{6a}$;
B² represents a CR¹;
B³ represents a CR$^{6c}$;
R¹ represents a C1-C3 perfluoroalkyl group, a 1-cyanocyclopropyl group, or a 1-cyano-1-methylethyl group; and
R$^{6a}$ and R$^{6c}$ are identical to or different from each other, and each represent a C1-C3 alkyl group optionally having one or more halogen atom(s), a halogen atom, or a hydrogen atom.

[Embodiment 42] The compound according to any one of Embodiments 1 to 7, wherein
Q represents the group represented by Q1;
B¹ represents a nitrogen atom or a CR$^{6a}$;
B² represents a CR¹;
B³ represents a nitrogen atom or a CR$^{6c}$;
R¹ represents a C1-C2 perfluoroalkyl group; and
R$^{6a}$ and R$^{6c}$ are identical to or different from each other, and each represent a C1-C3 alkyl group optionally having one or more halogen atom(s), a halogen atom, or a hydrogen atom.

[Embodiment 43] The compound according to any one of Embodiments 1 to 7, wherein
Q represents the group represented by Q1;
B¹ represents a nitrogen atom or a CR$^{6a}$;
B² represents a CR¹;
B³ represents a nitrogen atom;
R¹ represents a C1-C2 perfluoroalkyl group; and
R$^{6a}$ represents a C1-C3 alkyl group optionally having one or more halogen atom(s), a halogen atom, or a hydrogen atom.

[Embodiment 44] The compound according to any one of Embodiments 1 to 7, wherein
Q represents the group represented by Q1;
B¹ represents a nitrogen atom or a CR$^{6a}$;
B² represents a CR¹;
B³ represents a CR$^{6c}$;
R¹ represents a C1-C2 perfluoroalkyl group; and
R$^{6a}$ and R$^{6c}$ are identical to or different from each other, and each represent a C1-C3 alkyl group optionally having one or more halogen atom(s), a halogen atom, or a hydrogen atom.

[Embodiment 45] The compound according to any one of Embodiments 1 to 7, wherein
Q represents the group represented by Q1;
B¹ represents a nitrogen atom;
B² represents a CR¹;
B³ represents a nitrogen atom; and
R¹ represents a C1-C2 perfluoroalkyl group.

[Embodiment 46] The compound according to any one of Embodiments 1 to 7, wherein
Q represents the group represented by Q1;
B¹ represents a nitrogen atom;
B² represents a CR¹;
B³ represents a CH; and
R¹ represents a C1-C2 perfluoroalkyl group.

[Embodiment 47] The compound according to any one of Embodiments 1 to 7, wherein
Q represents the group represented by Q1;
B¹ represents a CH;
B² represents a CR¹;
B³ represents a nitrogen atom; and
R¹ represents a C1-C2 perfluoroalkyl group.

[Embodiment 48] The compound according to any one of Embodiments 1 to 7, wherein
Q represents the group represented by Q1;
B¹ represents a CH;
B² represents a CR¹;
B³ represents a CH; and
R¹ represents a C1-C2 perfluoroalkyl group.

[Embodiment 49] The compound according to any one of Embodiments 1 to 7, wherein
Q represents the group represented by Q2;
B¹ represents a nitrogen atom or a CR$^{6a}$;
B² represents a CR¹;
B³ represents a nitrogen atom or a CR$^{6c}$;
R¹ represents a C1-C3 perfluoroalkyl group, a 1-cyanocyclopropyl group, or a 1-cyano-1-methylethyl group; and
R$^{6a}$ and R$^{6c}$ are identical to or different from each other, and each represent a C1-C3 alkyl group optionally having one or more halogen atom(s), a halogen atom, or a hydrogen atom.

[Embodiment 50] The compound according to any one of Embodiments 1 to 7, wherein
Q represents the group represented by Q2;
B¹ represents a nitrogen atom or a CR$^{6a}$;
B² represents a CR¹;
B³ represents a nitrogen atom;
R¹ represents a C1-C3 perfluoroalkyl group, a 1-cyanocyclopropyl group, or a 1-cyano-1-methylethyl group; and
R$^{6a}$ represents a C1-C3 alkyl group optionally having one or more halogen atom(s), a halogen atom, or a hydrogen atom.

[Embodiment 51] The compound according to any one of Embodiments 1 to 7, wherein
Q represents the group represented by Q2;
B¹ represents a nitrogen atom or a CR$^{6a}$;
B² represents a CR¹;
B³ represents a R$^{6c}$;
R¹ represents a C1-C3 perfluoroalkyl group, a 1-cyanocyclopropyl group, or a 1-cyano-1-methylethyl group; and
R$^{6a}$ and R$^{6c}$ are identical to or different from each other, and each represent a C1-C3 alkyl group optionally having one or more halogen atom(s), a halogen atom, or a hydrogen atom.

[Embodiment 52] The compound according to any one of Embodiments 1 to 7, wherein
Q represents the group represented by Q2;
B¹ represents a nitrogen atom or a CR$^{6a}$;
B² represents a CR¹;
B³ represents a nitrogen atom or a CR$^{6c}$;
R¹ represents a C1-C2 perfluoroalkyl group; and $R^{6a}$ and $R^{6c}$ are identical to or different from each other, and each represent a C1-C3 alkyl group optionally having one or more halogen atom(s), a halogen atom, or a hydrogen atom.

[Embodiment 53] The compound according to any one of Embodiments 1 to 7, wherein
Q represents the group represented by Q2;
$B^1$ represents a nitrogen atom or a $CR^{6a}$;
$B^2$ represents a $CR^1$;
$B^3$ represents a nitrogen atom;
$R^1$ represents a C1-C2 perfluoroalkyl group; and
$R^{6a}$ represents a C1-C3 alkyl group optionally having one or more halogen atom(s), a halogen atom, or a hydrogen atom.

[Embodiment 54] The compound according to any one of Embodiments 1 to 7, wherein
Q represents the group represented by Q2;
$B^1$ represents a nitrogen atom or a $CR^{6a}$;
$B^2$ represents a $CR^1$;
$B^3$ represents a $CR^{6c}$;
$R^1$ represents a C1-C2 perfluoroalkyl group; and
$R^{6a}$ and $R^{6c}$ are identical to or different from each other, and each represent a C1-C3 alkyl group optionally having one or more halogen atom(s), a halogen atom, or a hydrogen atom.

[Embodiment 55] The compound according to any one of Embodiments 1 to 7, wherein
Q represents the group represented by Q2;
$B^1$ represents a nitrogen atom;
$B^2$ represents a $CR^1$;
$B^3$ represents a nitrogen atom; and
$R^1$ represents a C1-C2 perfluoroalkyl group.

[Embodiment 56] The compound according to any one of Embodiments 1 to 7, wherein
Q represents the group represented by Q2;
$B^1$ represents a nitrogen atom;
B2 represents a $CR^1$;
$B^3$ represents a CH; and
$R^1$ represents a C1-C2 perfluoroalkyl group.

[Embodiment 57] The compound according to any one of Embodiments 1 to 7, wherein
Q represents the group represented by Q2;
$B^1$ represents a CH;
$B^2$ represents a $CR^1$;
$B^3$ represents a nitrogen atom; and
$R^1$ represents a C1-C2 perfluoroalkyl group.

[Embodiment 58] The compound according to any one of Embodiments 1 to 7, wherein
Q represents the group represented by Q2;
$B^1$ represents a CH;
$B^2$ represents a $CR^1$;
$B^3$ represents a CH; and
$R^1$ represents a C1-C2 perfluoroalkyl group.

[Embodiment 59] The compound according to any one of Embodiments 1 to 7, wherein
$B^1$ represents a nitrogen atom or a $CR^{6a}$;
$B^2$ represents a nitrogen atom or a $CR^{6b}$;
$B^3$ represents a $CR^1$;
$R^1$ represents a C1-C3 perfluoroalkyl group, a 1-cyano-cyclopropyl group, or a 1-cyano-1-methylethyl group; and
$R^{6a}$ and $R^{6b}$ are identical to or different from each other, and each represent a C1-C3 alkyl group optionally having one or more halogen atom(s), a halogen atom, or a hydrogen atom.

[Embodiment 60] The compound according to any one of Embodiments 1 to 7, wherein
$B^1$ represents a nitrogen atom or a $CR^{6a}$;
$B^2$ represents a nitrogen atom;
$B^3$ represents a $CR^1$;
$R^1$ represents a C1-C3 perfluoroalkyl group, a 1-cyano-cyclopropyl group, or a 1-cyano-1-methylethyl group; and
$R^{6a}$ represents a C1-C3 alkyl group optionally having one or more halogen atom(s), a halogen atom, or a hydrogen atom.

[Embodiment 61] The compound according to any one of Embodiments 1 to 7, wherein
$B^1$ represents a nitrogen atom or a $CR^{6a}$;
$B^2$ represents a $CR^{6b}$;
$B^3$ represents a $CR^1$;
$R^1$ represents a C1-C3 perfluoroalkyl group, a 1-cyano-cyclopropyl group, or a 1-cyano-1-methylethyl group; and
$R^{6a}$ and $R^{6b}$ are identical to or different from each other, and each represent a C1-C3 alkyl group optionally having one or more halogen atom(s), a halogen atom, or a hydrogen atom.

[Embodiment 62] The compound according to any one of Embodiments 1 to 7, wherein
$B^1$ represents a nitrogen atom or a $CR^{6a}$;
$B^2$ represents a nitrogen atom or a $CR^{6b}$;
$B^3$ represents a $CR^1$;
$R^1$ represents a C1-C2 perfluoroalkyl group; and
$R^{6a}$ and $R^{6b}$ are identical to or different from each other, and each represent a C1-C3 alkyl group optionally having one or more halogen atom(s), a halogen atom, or a hydrogen atom.

[Embodiment 63] The compound according to any one of Embodiments 1 to 7, wherein
$B^1$ represents a nitrogen atom or a $CR^{6a}$;
$B^2$ represents a nitrogen atom;
$B^3$ represents a $CR^1$;
$R^1$ represents a C1-C2 perfluoroalkyl group; and
$R^{6a}$ represents a C1-C3 alkyl group optionally having one or more halogen atom(s), a halogen atom, or a hydrogen atom.

[Embodiment 64] The compound according to any one of Embodiments 1 to 7, wherein
$B^1$ represents a nitrogen atom or a $CR^{6a}$;
$B^2$ represents a $R^{6b}$;
$B^3$ represents a $CR^1$;
$R^1$ represents a C1-C2 perfluoroalkyl group; and
$R^{6a}$ and $R^{6b}$ are identical to or different from each other, and each represent a C1-C3 alkyl group optionally having one or more halogen atom(s), a halogen atom, or a hydrogen atom.

[Embodiment 65] The compound according to any one of Embodiments 1 to 7, wherein
$B^1$ represents a nitrogen atom;
$B^2$ represents a nitrogen atom;
$B^3$ represents a $CR^1$; and
$R^1$ represents a C1-C2 perfluoroalkyl group.

[Embodiment 66] The compound according to any one of Embodiments 1 to 7, wherein
$B^1$ represents a nitrogen atom;
$B^2$ represents a CH;
$B^3$ represents a $CR^1$; and
$R^1$ represents a C1-C2 perfluoroalkyl group.

[Embodiment 67] The compound according to any one of Embodiments 1 to 7, wherein
$B^1$ represents a CH;
$B^2$ represents a nitrogen atom;
$B^3$ represents a $CR^1$; and
$R^1$ represents a C1-C2 perfluoroalkyl group.

[Embodiment 68] The compound according to any one of Embodiments 1 to 7, wherein
B$^1$ represents a CH;
B$^2$ represents a CH;
B$^3$ represents a CR$^1$; and
R$^1$ represents a C1-C2 perfluoroalkyl group.

[Embodiment 69] The compound according to any one of Embodiments 1 to 7, wherein
Q represents the group represented by Q1;
B$^1$ represents a nitrogen atom or a CR$^{6a}$;
B$^2$ represents a nitrogen atom or a CR$^{6b}$;
B$^3$ represents a CR$^1$;
R$^1$ represents a C1-C3 perfluoroalkyl group, a 1-cyanocyclopropyl group, or a 1-cyano-1-methylethyl group; and
R$^{6a}$ and R$^{6b}$ are identical to or different from each other, and each represent a C1-C3 alkyl group optionally having one or more halogen atom(s), a halogen atom, or a hydrogen atom.

[Embodiment 70] The compound according to any one of Embodiments 1 to 7, wherein
Q represents the group represented by Q1;
B$^1$ represents a nitrogen atom or a CR$^{6a}$;
B$^2$ represents a nitrogen atom;
B$^3$ represents a CR$^1$;
R$^1$ represents a C1-C3 perfluoroalkyl group, a 1-cyanocyclopropyl group, or a 1-cyano-1-methylethyl group; and
R$^{6a}$ represents a C1-C3 alkyl group optionally having one or more halogen atom(s), a halogen atom, or a hydrogen atom.

[Embodiment 71] The compound according to any one of Embodiments 1 to 7, wherein
Q represents the group represented by Q1;
B$^1$ represents a nitrogen atom or a CR$^{6a}$;
B$^2$ represents a CR$^{6b}$;
B$^3$ represents a CR$^1$;
R$^1$ represents a C1-C3 perfluoroalkyl group, a 1-cyanocyclopropyl group, or a 1-cyano-1-methylethyl group; and
R$^{6a}$ and R$^{6b}$ are identical to or different from each other, and each represent a C1-C3 alkyl group optionally having one or more halogen atom(s), a halogen atom, or a hydrogen atom.

[Embodiment 72] The compound according to any one of Embodiments 1 to 7, wherein
Q represents the group represented by Q1;
B$^1$ represents a nitrogen atom or a CR$^{6a}$;
B$^2$ represents a nitrogen atom or a CR$^{6b}$;
B$^3$ represents a CR$^1$;
R$^1$ represents a C1-C2 perfluoroalkyl group; and
R$^{6a}$ and R$^{6b}$ are identical to or different from each other, and each represent a C1-C3 alkyl group optionally having one or more halogen atom(s), a halogen atom, or a hydrogen atom.

[Embodiment 73] The compound according to any one of Embodiments 1 to 7, wherein
Q represents the group represented by Q1;
B$^1$ represents a nitrogen atom or a CR$^{6a}$;
B$^2$ represents a nitrogen atom;
B$^1$ represents a CR$^1$;
R$^1$ represents a C1-C2 perfluoroalkyl group; and
R$^{6a}$ represents a C1-C3 alkyl group optionally having one or more halogen atom(s), a halogen atom, or a hydrogen atom.

[Embodiment 74] The compound according to any one of Embodiments 1 to 7, wherein
Q represents the group represented by Q1;
B$^1$ represents a nitrogen atom or a CR$^{6a}$;
B$^2$ represents a CR$^{6b}$;
B$^3$ represents a CR$^1$;
R$^1$ represents a C1-C2 perfluoroalkyl group; and
R$^{6a}$ and R$^{6b}$ are identical to or different from each other, and each represent a C1-C3 alkyl group optionally having one or more halogen atom(s), a halogen atom, or a hydrogen atom.

[Embodiment 75] The compound according to any one of Embodiments 1 to 7, wherein
Q represents the group represented by Q1;
B$^1$ represents a nitrogen atom;
B$^2$ represents a nitrogen atom;
B$^3$ represents a CR$^1$; and
R$^1$ represents a C1-C2 perfluoroalkyl group.

[Embodiment 76] The compound according to any one of Embodiments 1 to 7, wherein
Q represents the group represented by Q1;
B$^1$ represents a nitrogen atom;
B$^2$ represents a CH;
B$^3$ represents a CR$^1$; and
R$^1$ represents a C1-C2 perfluoroalkyl group.

[Embodiment 77] The compound according to any one of Embodiments 1 to 7, wherein
Q represents the group represented by Q1;
B$^1$ represents a CH;
B$^2$ represents a nitrogen atom;
B$^3$ represents a CR$^1$; and
R$^1$ represents a C1-C2 perfluoroalkyl group.

[Embodiment 78] The compound according to any one of Embodiments 1 to 7, wherein
Q represents the group represented by Q1;
B$^1$ represents a CH;
B$^2$ represents a CH;
B$^3$ represents a CR$^1$; and
R$^1$ represents a C1-C2 perfluoroalkyl group.

[Embodiment 79] The compound according to any one of Embodiments 1 to 7, wherein
Q represents the group represented by Q2;
B$^1$ represents a nitrogen atom or a CR$^{6a}$;
B$^2$ represents a nitrogen atom or a CR$^{6b}$;
B$^3$ represents a CR$^1$;
R$^1$ represents a C1-C3 perfluoroalkyl group, a 1-cyanocyclopropyl group, or a 1-cyano-1-methylethyl group; and
R$^{6a}$ and R$^{6b}$ are identical to or different from each other, and each represent a C1-C3 alkyl group optionally having one or more halogen atom(s), a halogen atom, or a hydrogen atom.

[Embodiment 80] The compound according to any one of Embodiments 1 to 7, wherein
Q represents the group represented by Q2;
B$^1$ represents a nitrogen atom or a CR$^{6a}$;
B$^2$ represents a nitrogen atom;
B$^3$ represents a CR$^1$;
R$^1$ represents a C1-C3 perfluoroalkyl group, a 1-cyanocyclopropyl group, or a 1-cyano-1-methylethyl group; and
R$^{6a}$ represents a C1-C3 alkyl group optionally having one or more halogen atom(s), a halogen atom, or a hydrogen atom.

[Embodiment 81] The compound according to any one of Embodiments 1 to 7, wherein
Q represents the group represented by Q2;
B$^1$ represents a nitrogen atom or a CR$^{6a}$;
B$^2$ represents a CR$^{6b}$;
B$^3$ represents a CR$^1$;
R$^1$ represents a C1-C3 perfluoroalkyl group, a 1-cyanocyclopropyl group, or a 1-cyano-1-methylethyl group; and $R^{6a}$ and $R^{6b}$ are identical to or different from each other, and each represent a C1-C3 alkyl group optionally having one or more halogen atom(s), a halogen atom, or a hydrogen atom.

[Embodiment 82] The compound according to any one of Embodiments 1 to 7, wherein
Q represents the group represented by Q2;
$B^1$ represents a nitrogen atom or a $CR^{6a}$;
$B^2$ represents a nitrogen atom or a $CR^{6b}$;
$B^3$ represents a $CR^1$;
$R^1$ represents a C1-C2 perfluoroalkyl group; and
$R^{6a}$ and $R^{6b}$ are identical to or different from each other, and each represent a C1-C3 alkyl group optionally having one or more halogen atom(s), a halogen atom, or a hydrogen atom.

[Embodiment 83] The compound according to any one of Embodiments 1 to 7, wherein
Q represents the group represented by Q2;
$B^1$ represents a nitrogen atom or a $CR^{6a}$;
$B^2$ represents a nitrogen atom;
$B^3$ represents a $CR^1$;
$R^1$ represents a C1-C2 perfluoroalkyl group; and
$R^{6a}$ represents a C1-C3 alkyl group optionally having one or more halogen atom(s), a halogen atom, or a hydrogen atom.

[Embodiment 84] The compound according to any one of Embodiments 1 to 7, wherein
Q represents the group represented by Q2;
$B^1$ represents a nitrogen atom or a $CR^{6a}$;
$B^2$ represents a $CR^{6b}$;
$B^3$ represents a $CR^1$;
$R^1$ represents a C1-C2 perfluoroalkyl group; and
$R^{6a}$ and $R^{6b}$ are identical to or different from each other, and each represent a C1-C3 alkyl group optionally having one or more halogen atom(s), a halogen atom, or a hydrogen atom.

[Embodiment 85] The compound according to any one of Embodiments 1 to 7, wherein
Q represents the group represented by Q2;
$B^1$ represents a nitrogen atom;
$B^2$ represents a nitrogen atom;
$B^3$ represents a $CR^1$; and
$R^1$ represents a C1-C2 perfluoroalkyl group.

[Embodiment 86] The compound according to any one of Embodiments 1 to 7, wherein
Q represents the group represented by Q2;
$B^1$ represents a nitrogen atom;
$B^2$ represents a CH;
$B^3$ represents a $CR^1$; and
$R^1$ represents a C1-C2 perfluoroalkyl group.

[Embodiment 87] The compound according to any one of Embodiments 1 to 7, wherein
Q represents the group represented by Q2;
$B^1$ represents a CH;
$B^2$ represents a nitrogen atom;
$B^3$ represents a $CR^1$; and
$R^1$ represents a C1-C2 perfluoroalkyl group.

[Embodiment 88] The compound according to any one of Embodiments 1 to 7, wherein
Q represents the group represented by Q2;
$B^1$ represents a CH;
$B^2$ represents a CH;
$B^3$ represents a $CR^1$; and
$R^1$ represents a C1-C2 perfluoroalkyl group.

[Embodiment 89] The compound according to any one of Embodiments 1 to 7, wherein Q represents the group represented by Q1.

[Embodiment 90] The compound according to any one of Embodiments 1 to 7, wherein Q represents the group represented by Q2.

Embodiment of the Present compound X include the following compounds.

[Embodiment 91] The Present compound X, wherein
Z represents an oxygen atom;
$R^2$ represents a C1-C6 alkyl group optionally substituted with one or more halogen atom(s);
$A^1$ represents a nitrogen atom or a CH; and
$R^{4a}$ and $R^{4b}$ each represent a hydrogen atom.

[Embodiment 92] The Present compound X, wherein
Z represents an oxygen atom;
$R^2$ represents an ethyl group;
$A^1$ represents a nitrogen atom or a CH; and
$R^{4a}$ and $R^{4b}$ each represent a hydrogen atom.

[Embodiment 93] The compound according to Embodiment 92, wherein n represents 2.

[Embodiment 94] The Present compound X, wherein
Z represents an oxygen atom;
$R^2$ represents an ethyl group;
$A^1$ represents a nitrogen atom;
$A^2$ and $A^3$ each represent a CH;
n represents 2; and
q represents 0 or 1.

[Embodiment 95] The compound according to Embodiment 94, wherein
$R^3$ represents a C1-C6 chain hydrocarbon group optionally having one or more substituent(s) selected from Group B, a C3-C7 cycloalkyl group optionally having one or more substituent(s) selected from Group E, a phenyl group optionally having one or more substituent(s) selected from Group H, a 5 or 6 membered aromatic heterocyclic group optionally having one or more substituent(s) selected from Group H, a —$OR^{12}$, a —$NR^{11}R^{12}$, a —$NR^{11}C(O)OR^{14}$, a —$NR^{11}C(O)NR^{15a}R^{16a}$, a —$C(O)OR^{17}$, a —$C(O)NR^{15a}R^{16a}$, a cyano group, a nitro group, or a halogen atom.

[Embodiment 96] The compound according to Embodiment 94, wherein
$R^3$ represents a C1-C6 alkyl group optionally having one or more halogen atom(s), a cyclopropyl group optionally having a cyano group, a phenyl group optionally having one or more substituent(s) selected from Group J, a 5 or 6 membered aromatic heterocyclic group optionally having one or more substituent(s) selected from Group J, a —$OR^{12}$, a —$NR^{11}R^{12}$, a —$NR^{11}C(O)OR^{14}$, a —$NR^{11}C(O)NR^{15a}R^{16a}$, a —$C(O)OR^{17}$, a —$C(O)NR^{15a}R^{16a}$, or a halogen atom.

[Embodiment 97] The compound according to Embodiment 94, wherein
$R^3$ represents a phenyl group optionally having one or more substituent(s) selected from the group consisting of a cyano group and a halogen atom, a cyclopropyl group optionally having a cyano group, a trifluoromethyl group, or a halogen atom.

[Embodiment 98] The compound according to Embodiment 94, wherein
$R^3$ represents a trifluoromethyl group, a cyclopropyl group, a hydroxy group, a phenyl group optionally having one or more halogen atom(s), a C1-C3 alkoxy group optionally substituted with one or more halogen atom(s), or a halogen atom.

[Embodiment 99] The compound according to any one of Embodiments 91 to 98, wherein
$B^1$ represents a nitrogen atom;
$B^2$ represents a $CR^1$;
$B^3$ represents a nitrogen atom; and $R^1$ represents a C1-C2 perfluoroalkyl group.
[Embodiment 100] The compound according to any one of Embodiments 91 to 98, wherein
$B^1$ represents a nitrogen atom;
$B^2$ represents a $CR^1$;
$B^3$ represents a CH; and
$R^1$ represents a C1-C2 perfluoroalkyl group.
[Embodiment 101] The compound according to any one of Embodiments 91 to 98, wherein
$B^1$ represents a CH;
$B^2$ represents a $CR^1$;
$B^3$ represents a nitrogen atom; and
$R^1$ represents a C1-C2 perfluoroalkyl group.
[Embodiment 102] The compound according to any one of Embodiments 91 to 98, wherein
$B^1$ represents a CH;
$B^2$ represents a $CR^1$;
$B^3$ represents a CH; and
$R^1$ represents a C1-C2 perfluoroalkyl group.
[Embodiment 103] The compound according to any one of Embodiments 91 to 98, wherein
Q represents the group represented by Q1;
$B^1$ represents a nitrogen atom;
$B^2$ represents a $CR^1$;
$B^3$ represents a nitrogen atom; and
$R^1$ represents a C1-C2 perfluoroalkyl group.
[Embodiment 104] The compound according to any one of Embodiments 91 to 98, wherein
Q represents the group represented by Q1;
$B^1$ represents a nitrogen atom;
$B^2$ represents a $CR^1$;
$B^3$ represents a CH; and
$R^1$ represents a C1-C2 perfluoroalkyl group.
[Embodiment 105] The compound according to any one of Embodiments 91 to 98, wherein
Q represents the group represented by Q1;
$B^1$ represents a CH;
$B^2$ represents a $CR^1$;
$B^3$ represents a nitrogen atom; and
$R^1$ represents a C1-C2 perfluoroalkyl group.
[Embodiment 106] The compound according to any one of Embodiments 91 to 98, wherein
Q represents the group represented by Q1;
$B^1$ represents a CH;
$B^2$ represents a $CR^1$;
$B^3$ represents a CH; and
$R^1$ represents a C1-C2 perfluoroalkyl group.
[Embodiment 107] The compound according to any one of Embodiments 91 to 98, wherein
Q represents the group represented by Q2;
$B^1$ represents a nitrogen atom;
$B^2$ represents a $CR^1$;
$B^3$ represents a nitrogen atom; and
$R^1$ represents a C1-C2 perfluoroalkyl group.
[Embodiment 108] The compound according to any one of Embodiments 91 to 98, wherein
Q represents the group represented by Q2;
$B^1$ represents a nitrogen atom;
$B^2$ represents a $CR^1$;
$B^3$ represents a CH; and
$R^1$ represents a C1-C2 perfluoroalkyl group.
[Embodiment 109] The compound according to any one of Embodiments 91 to 98, wherein
Q represents the group represented by Q2;
$B^1$ represents a CH;
$B^2$ represents a $CR^1$;
$B^3$ represents a nitrogen atom; and
$R^1$ represents a C1-C2 perfluoroalkyl group.
[Embodiment 110] The compound according to any one of Embodiments 91 to 98, wherein
Q represents the group represented by Q2;
$B^1$ represents a CH;
$B^2$ represents a $CR^1$;
$B^3$ represents a CH; and
$R^1$ represents a C1-C2 perfluoroalkyl group.

Next, processes for preparing the Present compound X are described.

Process 1

A compound represented by formula (I-n1) (hereinafter referred to as "Compound (I-n1)") or a compound represented by formula (I-n2) (hereinafter referred to as "Compound (I-n2)") may be prepared by reacting a compound represented by formula (I-n0) (hereinafter referred to as "Compound (I-n0)") with an oxidizing agent. The Compound (I-n2) may also be prepared by reacting the Compound (I-n1) with an oxidizing agent.

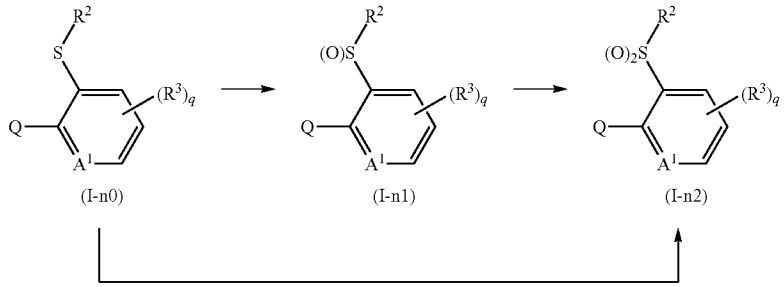

[wherein the symbols are the same as defined above.]

First, a method for producing the Compound (I-n1) from the Compound (I-n0) is described.

The reaction is usually carried out in a solvent. Examples of the solvent to be used in the reaction include halogenated hydrocarbons such as dichloromethane and chloroform (hereinafter collectively referred to as "halogenated hydrocarbons"); nitriles such as acetonitrile (hereinafter collectively referred to as "nitriles"); alcohols such as methanol and ethanol (hereinafter collectively referred to as "alcohols"); acetic acid; water; and mixed solvents thereof.

Examples of the oxidizing agent to be used in the reaction include sodium periodate, m-chloroperbenzoic acid (hereinafter referred to as "mCPBA"), and hydrogen peroxide.

When hydrogen peroxide is used as the oxidizing agent, a base or a catalyst may also be used as needed.

Examples of the base include sodium carbonate. When a base is used, the base is usually used at a ratio of 0.01 to 1 mol, relative to 1 mol of the Compound (I-n0).

Examples of the catalyst include tungstic acid and sodium tungstate. When a catalyst is used, the catalyst is usually used at a ratio of 0.01 to 0.5 mol, relative to 1 mol of the Compound (I-n0).

In the reaction, the oxidizing agent is usually used at a ratio of 1 to 1.2 mol, relative to 1 mol of the Compound (I-n0).

The reaction temperature is usually within the range of −20 to 80° C. The reaction time is usually within the range of 0.1 to 12 hour(s).

When the reaction is completed, the reaction mixture may be subjected to a work-up such as adding water to the reaction mixture, extracting the resulting reaction mixture with organic solvent(s), and washing the resulting organic layer with an aqueous solution of a reducing agent (for example, sodium sulfite or sodium thiosulfate) and an aqueous solution of a base (for example, sodium hydrogen carbonate) as needed. The resulting organic layer may be dried or concentrated to give the Compound (I-n1).

Next, a method for producing the Compound (I-n2) from the Compound (I-n1) is described.

The reaction is usually carried out in a solvent. Examples of the solvent to be used in the reaction include halogenated hydrocarbons, nitriles, alcohols, acetic acid, water, and mixed solvents thereof.

Examples of the oxidizing agent to be used in the reaction include mCPBA and hydrogen peroxide.

When hydrogen peroxide is used as the oxidizing agent, a base or a catalyst may also be used as needed.

Examples of the base include sodium carbonate. When a base is used, the base is usually used at a ratio of 0.01 to 1 mol, relative to 1 mol of the Compound (I-n1).

Examples of the catalyst include sodium tungstate. When a catalyst is used, the catalyst is usually used at a ratio of 0.01 to 0.5 mol, relative to 1 mol of the Compound (I-n1).

In the reaction, the oxidizing agent is usually used at a ratio of 1 to 2 mol, relative to 1 mol of the Compound (I-n1).

The reaction temperature is usually within the range of −20 to 120° C. The reaction time is usually within the range of 0.1 to 12 hour(s).

When the reaction is completed, the reaction mixture may be subjected to a work-up such as adding water to the reaction mixture, extracting the resulting reaction mixture with organic solvent(s), and washing the resulting organic layer with an aqueous solution of a reducing agent (for example, sodium sulfite or sodium thiosulfate) and an aqueous solution of a base (for example, sodium hydrogen carbonate) as needed. The resulting organic layer may be dried or concentrated to give the Compound (I-n2).

Also, the Compound (I-n2) may be prepared in one step reaction (one-pot) by reacting the Compound (I-n0) with an oxidizing agent.

The reaction may be carried out according to the same method as the method for producing the Compound (I-n2) from the Compound (I-n1) by usually using the oxidizing agent at a ratio of 2 to 5 mol relative to 1 mol of the Compound (I-n0).

Process 2

The Compound (I-n0) may be prepared by reacting a compound represented by formula (M-1) (hereinafter referred to as "Compound (M-1)") with a compound represented by formula (R-1) (hereinafter referred to as "Compound (R-1)") in the presence of a base.

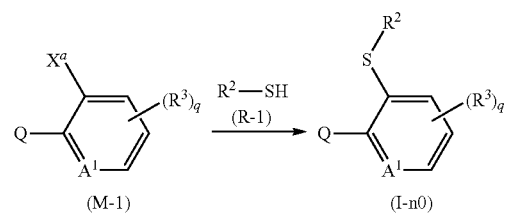

[wherein $X^a$ represents a fluorine atom, a chlorine atom, or a bromine atom; and the other symbols are the same as defined above.]

The reaction is usually carried out in a solvent. Examples of the solvent to be used in the reaction include ethers such as tetrahydrofuran (hereinafter referred to as "THF"), 1,2-dimethoxyethane (hereinafter referred to as "DME"), and methyl tert-butyl ether (hereinafter collectively referred to as "ethers"); aromatic hydrocarbons such as toluene and xylene (hereinafter collectively referred to as "aromatic hydrocarbons"); nitriles; aprotic polar solvents such as dimethylformamide (hereinafter referred to as "DMF"), N-methylpyrrolidone (hereinafter referred to as "NMP"), and dimethyl sulfoxide (hereinafter referred to as "DMSO") (hereinafter collectively referred to as "aprotic polar solvents"); water; and mixed solvents thereof.

Examples of the base to be used in the reaction include alkali metal carbonates such as sodium carbonate and potassium carbonate (hereinafter collectively referred to as "alkali metal carbonates"); alkali metal hydrides such as sodium hydride (hereinafter collectively referred to as "alkali metal hydrides"); and organic bases such as triethylamine, diisopropylethylamine, pyridine, and 4-(dimethylamino)pyridine (hereinafter collectively referred to as "organic bases").

In the reaction, the Compound (R-1) is usually used at a ratio of 1 to 3 mol, and the base is usually used at a ratio of 1 to 3 mol, relative to 1 mol of the Compound (M-1).

The reaction temperature is usually within the range of −20° C. to 150° C. The reaction time is usually within the range of 0.5 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (I-n0).

The Compound (R-1) is a commercially available compound or may be prepared by using known method(s).

Process 3

A compound represented by formula (P2) (hereinafter referred to as "Compound (P2)") may be prepared by reacting a compound represented by formula (P1) (hereinafter referred to as "Compound (P1)") with a sulfating agent.

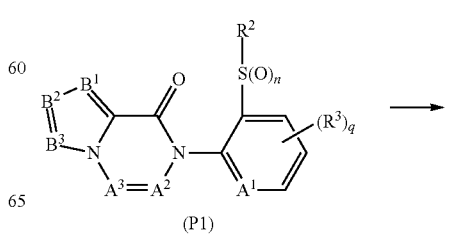

[chemical structure (P2)]

[wherein the symbols are the same as defined above.]

The reaction is carried out in a solvent or in the absence of a solvent. Examples of the solvent include ethers; halogenated hydrocarbons; aromatic hydrocarbons; nitriles; nitrogen-containing aromatic compounds such as pyridine, picoline, lutidine, and quinoline; and mixed solvents thereof.

Examples of the sulfating agent to be used in the reaction include phosphorus pentasulfide and Lawesson's reagent (2,4-bis(4-methoxyphenyl)-1,3-dithia-2,4-diphosphetane-2,4-disulfide).

In the reaction, the sulfating agent is usually used at a ratio of 1 to 3 mol, relative to 1 mol of the Compound (P1).

The reaction temperature is usually within the range of 0° C. to 200° C. The reaction time is usually within the range of 1 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (P2).

Process 4

A compound represented by formula (P4) (hereinafter referred to as "Compound (P4)") may be prepared by reacting a compound represented by formula (P3) (hereinafter referred to as "Compound (P3)") with a sulfating agent.

[chemical structure (P3)]

[chemical structure (P4)]

[wherein the symbols are the same as defined above.]

The reaction may be carried out according to the same method as the Process 3.

Process 5

The Compound (P1) may be prepared by reacting a compound represented by formula (M-2) (hereinafter referred to as "Compound (M-2)") with a compound represented by formula (M-3) (hereinafter referred to as "Compound (M-3)") in the presence of a base.

[chemical structures (M-2) + (M-3) → (P1)]

[wherein $X^b$ represents a halogen atom; and the other symbols are the same as defined above.]

The reaction is usually carried out in a solvent. Examples of the solvent to be used in the reaction include ethers, aromatic hydrocarbons, nitriles, aprotic polar solvents, and mixed solvents thereof.

Examples of the base to be used in the reaction include organic bases, alkali metal carbonates, and alkali metal hydrides.

The reaction may also be carried out by using a metal catalyst as needed. Examples of the metal catalyst include copper catalysts such as copper(I) iodide, copper(I) bromide, copper(I) chloride, copper(I) oxide, copper(I) trifluoromethanesulfonate benzene complex, tetrakis(acetonitrile)copper (I) hexafluorophosphate, and copper(I) 2-thiophenecarboxylate; nickel catalysts such as bis(cyclooctadiene)nickel(0) and nickel(II) chloride; and palladium catalysts such as palladium(II) acetate, tetrakis(triphenylphosphine)palladium(0), and tris(dibenzylideneacetone)dipalladium(II). When a metal catalyst is used in the reaction, the metal catalyst is usually used at a ratio of 0.01 to 0.5 mol, relative to 1 mol of the Compound (M-2).

The reaction may also be carried out by using a ligand as needed. Examples of the ligand include triphenylphosphine, Xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, 1,10-phenanthroline, trans-1,2-cyclohexanediamine, trans-N,N'-dimethylcyclohexane-1,2-diamine, and N,N'-dimethylethylenediamine. When a ligand is used in the reaction, the ligand is usually used at a ratio of 0.01 to 0.5 mol, relative to 1 mol of the Compound (M-2).

In the reaction, the Compound (M-3) is usually used at a ratio of 0.8 to 1.2 mol, and the base is usually used at a ratio of 1 to 3 mol, relative to 1 mol of the Compound (M-2).

The reaction temperature is usually within the range of −20° C. to 150° C. The reaction time is usually within the range of 0.5 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (P1).

Process 6

The Compound (P3) may be prepared by reacting a compound represented by formula (M-4) (hereinafter referred to as "Compound (M-4)") with the Compound (M-3) in the presence of a base.

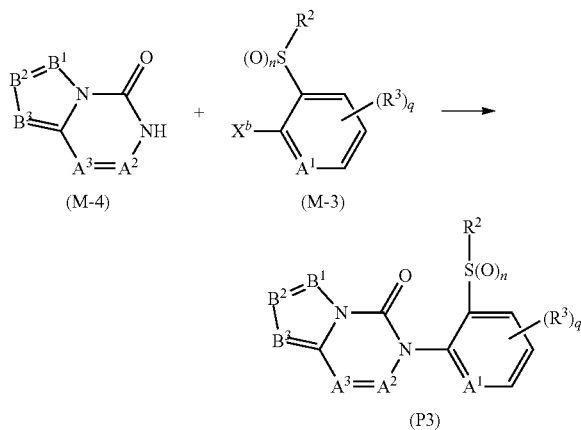

[wherein the symbols are the same as defined above.]

The reaction may be carried out according to the same method as the Process 5.

Process 7

A compound represented by formula (P5) (hereinafter referred to as "Compound (P5)") may be prepared by reacting a compound represented by formula (M-5) (hereinafter referred to as "Compound (M-5)") with a compound represented by formula (R-2) (hereinafter referred to as "Compound (R-2)").

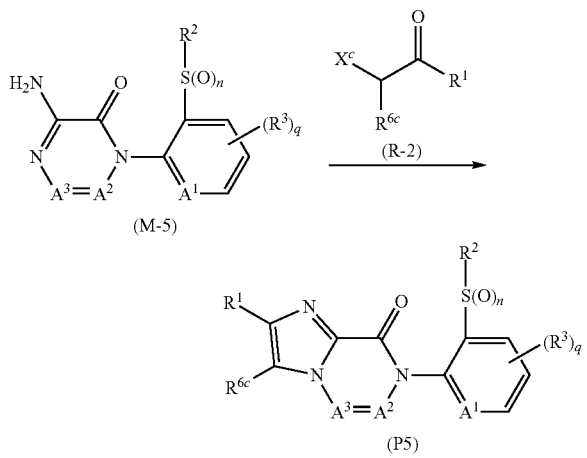

[wherein $X^c$ represents a chlorine atom, a bromine atom, or an iodine atom; and the other symbols are the same as defined above.]

The reaction is carried out in a solvent or in the absence of a solvent. Examples of the solvent include ethers, aromatic hydrocarbons, halogenated hydrocarbons, esters such as ethyl acetate (hereinafter collectively referred to as "esters"), nitriles, aprotic polar solvents, and mixed solvents thereof.

The reaction may also be carried out by using a base as needed. Examples of the base include alkali metal carbonates; and alkali metal hydrogen carbonates such as sodium hydrogen carbonate. When a base is used in the reaction, the base is usually used at a ratio of 1 to 3 mol, relative to 1 mol of the Compound (M-5).

In the reaction, the Compound (R-2) is usually used at a ratio of 1 to 3 mol, relative to 1 mol of the Compound (M-5).

The reaction temperature is usually within the range of 20 to 200° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (P5).

The Compound (R-2) is a commercially available compound or may be prepared by using known method(s).

Process 8

A compound represented by formula (P6) (hereinafter referred to as "Compound (P6)") may be prepared by reacting a compound represented by formula (M-6) (hereinafter referred to as "Compound (M-6)") with a compound represented by formula (R-3) (hereinafter referred to as "Compound (R-3)").

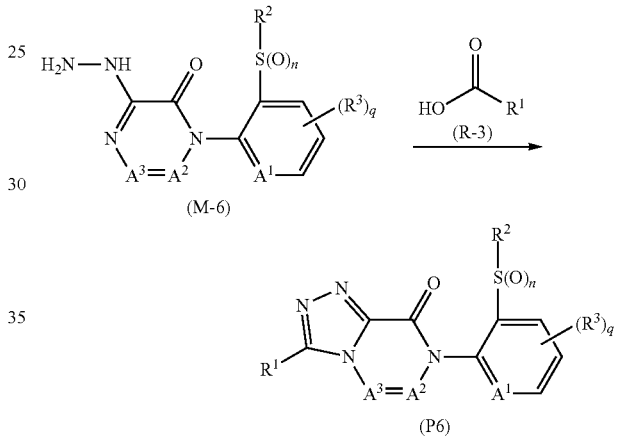

[wherein the symbols are the same as defined above.]

The reaction is carried out in a solvent or in the absence of a solvent. Examples of the solvent include ethers, aromatic hydrocarbons, halogenated hydrocarbons, esters, nitriles, aprotic polar solvents, and mixed solvents thereof.

In the reaction, the Compound (R-3) is usually used at a ratio of 1 to 3 mol, relative to 1 mol of the Compound (M-6).

The reaction temperature is usually within the range of 20 to 200° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (P6).

The Compound (R-3) is a commercially available compound or may be prepared by using known method(s).

Process 9

A compound represented by formula (P7) (hereinafter referred to as "Compound (P7)") may be prepared by reacting a compound represented by formula (M-7) (hereinafter referred to as "Compound (M-7)") with a compound represented by formula (R-4) (hereinafter referred to as "Compound (R-4)").

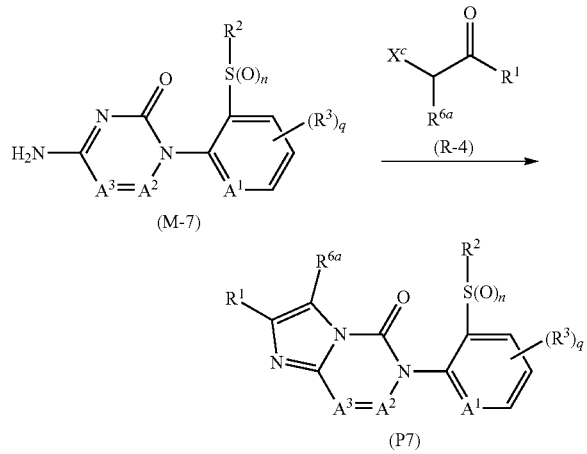

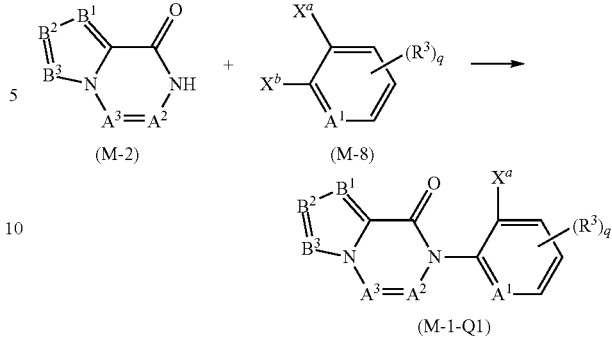

(M-1-Q1)

[wherein the symbols are the same as defined above.]

The reaction may be carried out according to the same method as the Process 5.

The Compound (M-8) is a commercially available compound or may be prepared by using known method(s).

Reference Process 2

A compound represented by formula (M-1-Q2) (hereinafter referred to as "Compound (M-1-Q2)") may be prepared by reacting the Compound (M-4) with the Compound (M-8) in the presence of a base.

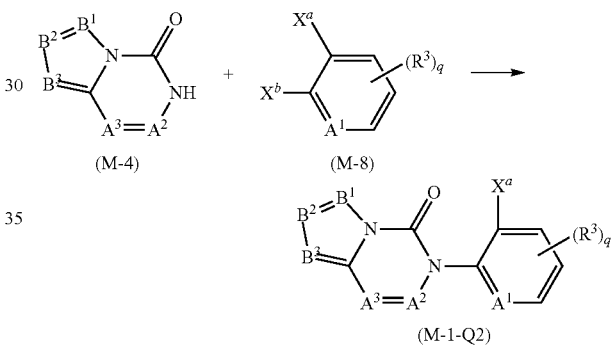

[wherein the symbols are the same as defined above.]

The reaction may be carried out according to the same method as the Process 5.

[wherein the symbols are the same as defined above.]

The reaction may be carried out according to the same method as the Process 7 by using the Compound (M-7) instead of the Compound (M-5) and using the Compound (R-4) instead of the Compound (R-2).

The Compound (R-4) is a commercially available compound or may be prepared by using known method(s).

Process 10

An N-oxide compound of the compound represented by formula (I) may be prepared by reacting the compound represented by formula (I) with an oxidizing agent. The reaction may be carried out according to the same method as described in, for example, the Process 1, US Patent Application Publication No. 2018/0009778, or WO 2016/121970 pamphlet.

Process 11

A compound represented by formula (I-n2-NO) may be prepared by reacting a compound represented by formula (I-n2-N) with an oxidizing agent.

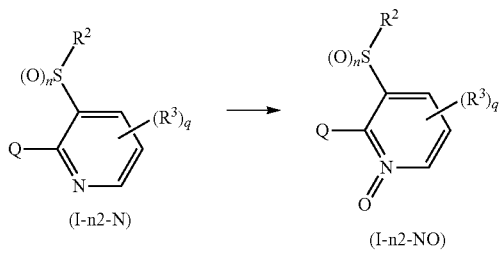

[wherein the symbols are the same as defined above.]

The reaction may be carried out according to the same method as the Process 1 or Process 10.

Hereinafter, processes for preparing the production intermediate compounds are described.

Reference Process 1

A compound represented by formula (M-1-Q1) (hereinafter referred to as "Compound (M-1-Q1)") may be prepared by reacting the Compound (M-2) with a compound represented by formula (M-8) (hereinafter referred to as "Compound (M-8)") in the presence of a base.

Reference Process 3

A compound represented by formula (M-3-n0) (hereinafter referred to as "Compound (M-3-n0)") may be prepared by reacting a compound represented by formula (M-8-1) (hereinafter referred to as "Compound (M-8-1)") with the Compound (R-1) in the presence of a base.

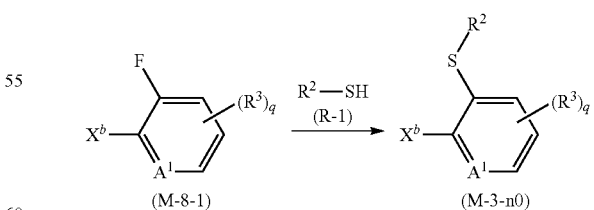

[wherein the symbols are the same as defined above.]

The reaction may be carried out according to the same method as the Process 2.

Reference Process 4

A compound represented by formula (M-3-n1) (hereinafter referred to as "Compound (M-3-n1)") or a compound represented by formula (M-3-n2) (hereinafter referred to as "Compound (M-3-n2)") may be prepared by reacting the Compound (M-3-n0) with an oxidizing agent. The Compound (M-3-n2) may also be prepared by reacting the Compound (M-3-n1) with an oxidizing agent.

Compound (M-1) and using a compound represented by formula (R-5) (hereinafter referred to as "Compound (R-5)") instead of the Compound (R-1).

The Compound (R-5) is a commercially available compound or may be prepared by using known method(s).

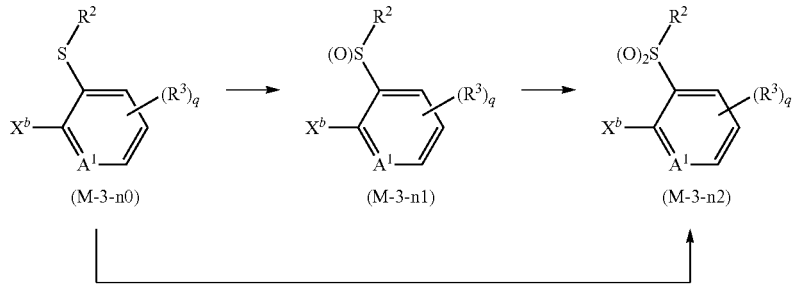

[wherein the symbols are the same as defined above.]

These reactions may be carried out according to the same method as the Process 1.

Reference Process 5

A compound represented by formula (M-2-1) (hereinafter referred to as "Compound (M-2-1)") may be prepared according to the following scheme.

The Compound (M-2-1) may be prepared according to the Process 7 by using a compound represented by formula (M-11) (hereinafter referred to as "Compound (M-11)") instead of the Compound (M-5).

The Compound (M-2-1) may also be prepared by reacting the Compound (M-13) wherein $R^{50}$ represents a benzyl

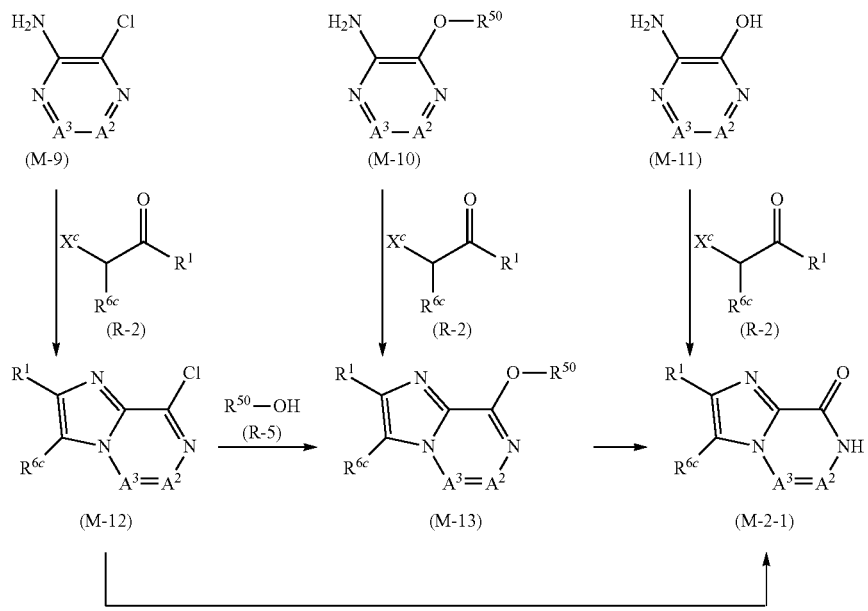

[wherein $R^{50}$ represents a benzyl group or a C1-C3 alkyl group; and the other symbols are the same as defined above.]

A compound represented by formula (M-12) (hereinafter referred to as "Compound (M-12)") may be prepared according to the Process 7 by using a compound represented by formula (M-9) (hereinafter referred to as "Compound (M-9)") instead of the Compound (M-5).

A compound represented by formula (M-13) (hereinafter referred to as "Compound (M-13)") may be prepared according to the Process 7 by using a compound represented by formula (M-10) (hereinafter referred to as "Compound (M-10)") instead of the Compound (M-5).

The Compound (M-13) may also be prepared according to the Process 2 by using the Compound (M-12) instead of the group (hereinafter referred to as "Compound (M-13-1)") with hydrogen in the presence of a catalyst.

The reaction is carried out usually under hydrogen atmosphere of 1 to 100 atm and usually in a solvent. Examples of the solvent to be used in the reaction include ethers, esters, alcohols, water, and mixed solvents thereof.

Examples of the catalyst to be used in the reaction include transition metal compounds such as palladium carbon, palladium(II) hydroxide, Raney nickel, and platinum oxide.

In the reaction, the catalyst is usually used at a ratio of 0.001 to 0.5 mol, relative to 1 mol of the Compound (M-13-1).

The reaction may also be carried out by using an acid, a base, or the like as needed.

Examples of the acid include acetic acid and hydrochloric acid, and examples of the base include tertiary amines such as triethylamine. When an acid is used in the reaction, the acid is usually used at a ratio of 0.001 to 0.5 mol, relative to 1 mol of the Compound (M-13-1). When a base is used in the reaction, the base is usually used at a ratio of 0.1 to 5 mol, relative to 1 mol of the Compound (M-13-1).

The reaction temperature is usually within the range of −20 to 100° C. The reaction time is usually within the range of 0.1 to 24 hour(s).

When the reaction is completed, the reaction mixture may be subjected to a work-up such as filtering it, and as needed, extracting it with organic solvent(s), and drying or concentrating the resulting organic layer to give the Compound (M-2-1).

Also, the Compound (M-2-1) may also be prepared by reacting the Compound (M-13) with an acid.

The reaction is usually carried out in a solvent. Examples of the solvent to be used in the reaction include halogenated hydrocarbons, water, and mixed solvents thereof.

Examples of the acid to be used in the reaction include mineral acids such as hydrochloric acid and sulfuric acid.

In the reaction, the acid is usually used at a ratio of 1 to 100 mol, relative to 1 mol of the Compound (M-13).

The reaction temperature is usually within the range of 50 to 150° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (M-2-1).

In the reaction, the acid is usually used at a ratio of 1 to 100 mol, relative to 1 mol of the Compound (M-12).

The reaction temperature is usually within the range of 50 to 100° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (M-2-1).

When the Compound (M-12) is hydrolyzed in the presence of a base, the reaction is usually carried out in water. Further, ethers, alcohols, or the like may also be added thereto as a solvent.

Examples of the base include alkali metal hydroxides such as sodium hydroxide and potassium hydroxide.

In the reaction, the base is usually used at a ratio of 1 to 10 mol, relative to 1 mol of the Compound (M-12).

The reaction temperature is usually within the range of 50 to 120° C. The reaction time is usually within the range of 0.1 to 24 hour(s).

When the reaction is completed, the reaction mixture may be subjected to a work-up such as adding an acid thereto to acidify the mixture, then extracting the resulting mixture with organic solvent(s), and drying or concentrating the resulting organic layer to give the Compound (M-2-1).

The Compound (M-9), the Compound (M-10), and the Compound (M-11) are commercially available compounds or may be prepared by using known method(s).

Reference Process 6

A compound represented by formula (M-2-2) (hereinafter referred to as "Compound (M-2-2)") may be prepared according to the following scheme.

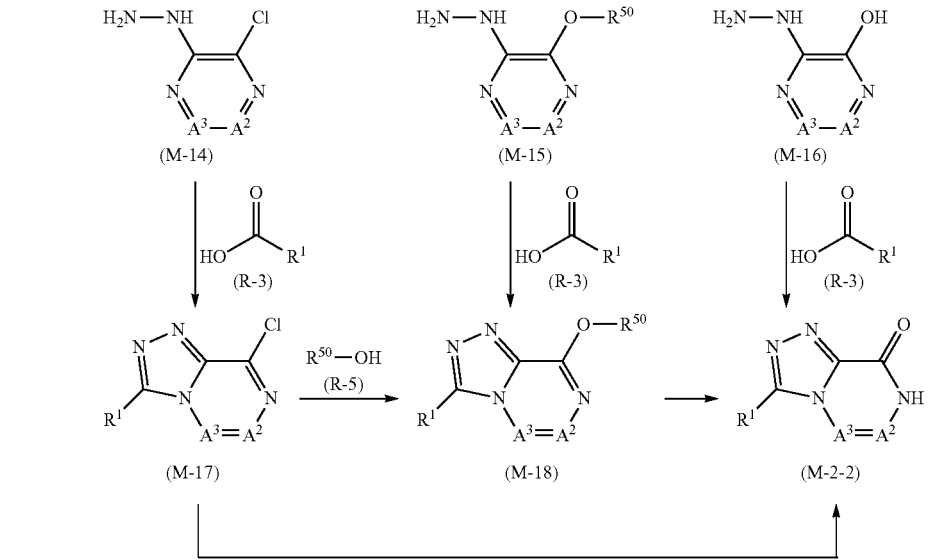

The Compound (M-2-1) may also be prepared by hydrolyzing the Compound (M-12) in the presence of an acid or a base.

When the Compound (M-12) is hydrolyzed in the presence of an acid, the reaction is usually carried out in water. Further, ethers, alcohols, or the like may also be added thereto as a solvent.

Examples of the acid include mineral acids such as hydrochloric acid and sulfuric acid.

[wherein the symbols are the same as defined above.]

A compound represented by formula (M-17) (hereinafter referred to as "Compound (M-17)") may be prepared according to the same method as described in the Process 8 by using a compound represented by formula (M-14) (hereinafter referred to as "Compound (M-14)") instead of the Compound (M-6).

A compound represented by formula (M-18) (hereinafter referred to as "Compound (M-18)") may be prepared according to the Process 8 by using a compound represented by formula (M-15) (hereinafter referred to as "Compound (M-15)") instead of the Compound (M-6).

Also, the Compound (M-18) may also be prepared according to the Process 2 by using the Compound (M-17) instead of the Compound (M-1) and using the Compound (R-5) instead of the Compound (R-1).

The Compound (M-2-2) may be prepared according to the Process 8 by using a compound represented by formula (M-16) (hereinafter referred to as "Compound (M-16)") instead of the Compound (M-6).

The Compound (M-2-2) may also be prepared according to the method for producing the Compound (M-2-1) from the Compound (M-13) in the Reference process 5 by using the Compound (M-18) instead of the Compound (M-13).

The Compound (M-2-2) may also be prepared according to the method for producing the Compound (M-2-1) from the Compound (M-12) in the Reference process 5 by using the Compound (M-17) instead of the Compound (M-12).

The Compound (M-14), the Compound (M-15), and the Compound (M-16) are commercially available compounds or may be prepared by using known method(s).

Reference Process 7

A compound represented by formula (M-4-1) (hereinafter referred to as "Compound (M-4-1)") may be prepared according to the following scheme.

The Compound (M-23) may also be prepared according to the Process 2 by using the Compound (M-22) instead of the Compound (M-1) and using the Compound (R-5) instead of the Compound (R-1).

The Compound (M-4-1) may be prepared according to the Process 7 by using a compound represented by formula (M-21) (hereinafter referred to as "Compound (M-21)") instead of the Compound (M-5) and using the Compound (R-4) instead of the Compound (R-2).

The Compound (M-4-1) may also be prepared according to the method for producing the Compound (M-2-1) from the Compound (M-13) in the Reference process 5 by using the Compound (M-23) instead of the Compound (M-13).

The Compound (M-4-1) may also be prepared according to the method for producing the Compound (M-2-1) from the Compound (M-12) in the Reference process 5 by using the Compound (M-22) instead of the Compound (M-12).

The Compound (M-19), the Compound (M-20), and the Compound (M-21) are commercially available compounds or may be prepared by using known method(s).

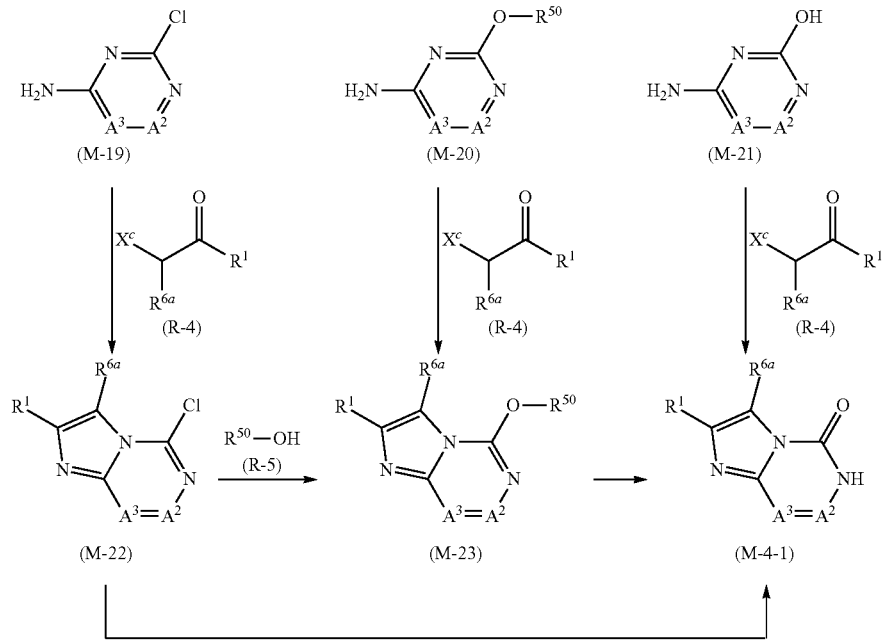

[wherein the symbols are the same as defined above.]

A compound represented by formula (M-22) (hereinafter referred to as "Compound (M-22)") may be prepared according to the Process 7 by using a compound represented by formula (M-19) (hereinafter referred to as "Compound (M-19)") instead of the Compound (M-5) and using the Compound (R-4) instead of the Compound (R-2).

A compound represented by formula (M-23) (hereinafter referred to as "Compound (M-23)") may be prepared according to the Process 7 by using a compound represented by formula (M-20) (hereinafter referred to as "Compound (M-20)") instead of the Compound (M-5) and using the Compound (R-4) instead of the Compound (R-2).

Reference Process 8

A compound represented by formula (M-28) (hereinafter referred to as "Compound (M-28)") may be prepared according to the following scheme.

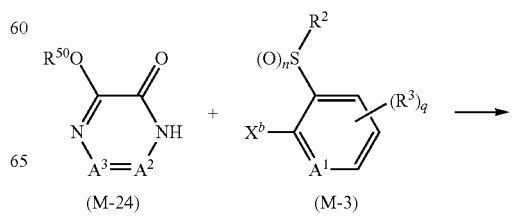

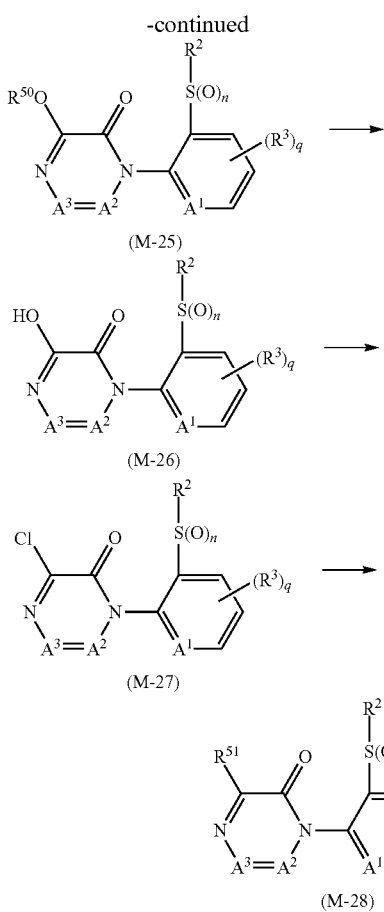

(M-25)

(M-26)

(M-27)

(M-28)

[wherein $R^{51}$ represents an amino group or a hydrazinyl group; and the other symbols are the same as defined above.]

A compound represented by formula (M-25) (hereinafter referred to as "Compound (M-25)") may be prepared according to the Process 5 by using the Compound (M-24) instead of the Compound (M-2).

A compound represented by formula (M-26) (hereinafter referred to as "Compound (M-26)") may be prepared according to the method for producing the Compound (M-2-1) from the Compound (M-13) in the Reference process 5 by using the Compound (M-25) instead of the Compound (M-13).

A compound represented by formula (M-27) (hereinafter referred to as "Compound (M-27)") may be prepared by reacting the Compound (M-26) with a chlorinating agent.

The reaction is usually carried out in a solvent. Examples of the solvent to be used in the reaction include ethers, aromatic hydrocarbons, halogenated hydrocarbons, and mixed solvents thereof.

Examples of the chlorinating agent to be used in the reaction include thionyl chloride, oxalyl chloride, phosphorus oxychloride, and phosphorus pentachloride.

In the reaction, the chlorinating agent is usually used at a ratio of 1 to 5 mol, relative to 1 mol of the Compound (M-26).

The reaction temperature is usually within the range of 0 to 100° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (M-27).

The Compound (M-28) may be prepared by reacting the Compound (M-27) with ammonia or hydrazine.

The reaction is usually carried out in a solvent. Examples of the solvent to be used in the reaction include ethers, aromatic hydrocarbons, nitriles, aprotic polar solvents, water, and mixed solvents thereof.

The reaction may also be carried out by using a base as needed. Examples of the base include alkali metal hydrides; alkali metal carbonates; tertiary amines such as triethylamine and N,N-diisopropylethylamine; and nitrogen-containing aromatic compounds such as pyridine and 4-dimethylaminopyridine. When a base is used in the reaction, the base is usually used at a ratio of 1 to 10 mol, relative to 1 mol of the Compound (M-27).

In the reaction, ammonia or hydrazine is usually used at a ratio of 1 to 10 mol, relative to 1 mol of the Compound (M-27).

The reaction temperature is usually within the range of 0 to 150° C. The reaction time is usually within the range of 0.5 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (M-28).

The Compound (M-24) is a commercially available compound or may be prepared by using known method(s).

Reference Process 9

The Compound (M-7) may be prepared according to the following scheme.

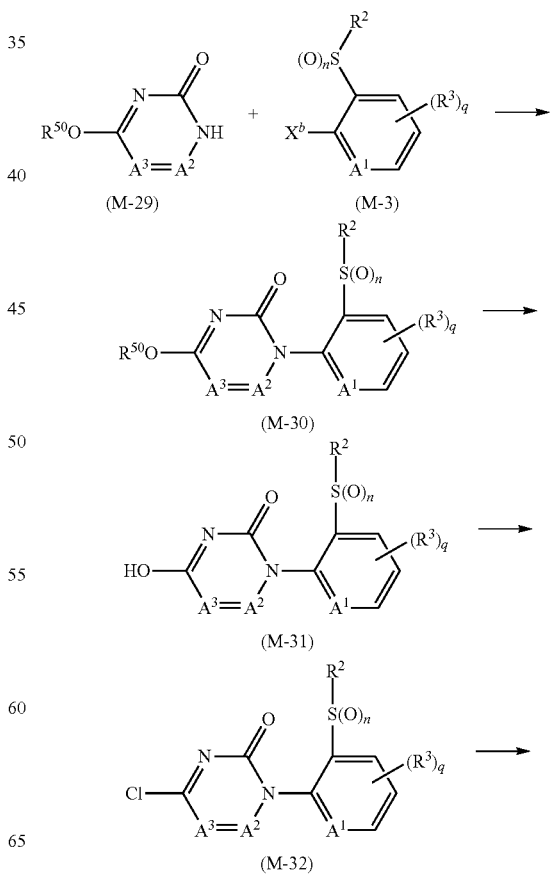

(M-29) + (M-3)

(M-30)

(M-31)

(M-32)

-continued

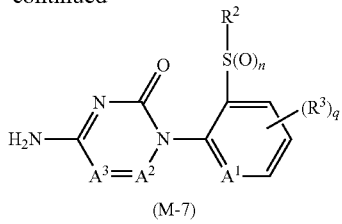

(M-7)

[wherein the symbols are the same as defined above.]

A compound represented by formula (M-30) (hereinafter referred to as "Compound (M-30)") may be prepared according to the Process 5 by using a compound represented by formula (M-29) (hereinafter referred to as "Compound (M-29)") instead of the Compound (M-2).

A compound represented by formula (M-31) (hereinafter referred to as "Compound (M-31)") may be prepared according to the method for producing the Compound (M-2-1) from the Compound (M-13) in the Reference process 5 by using the Compound (M-30) instead of the Compound (M-13).

A compound represented by formula (M-32) (hereinafter referred to as "Compound (M-32)") may be prepared according to the method for producing the Compound (M-27) from the Compound (M-26) in the Reference process 8 by using the Compound (M-31) instead of the Compound (M-26).

The Compound (M-7) may be prepared according to the method for producing the Compound (M-28) from the Compound (M-27) in the Reference process 8 by using the Compound (M-32) instead of the Compound (M-27).

The Compound (M-29) is a commercially available compound or may be prepared by using known method(s).

The Present compound or the Present compound X may be mixed with or used in combination with one or more ingredient(s) selected from the group consisting of the following Group (a), Group (b), Group (c), Group (d), Group (e), Group (f), Group (g), and Group (h) (hereinafter referred to as "Present ingredient").

When the Present compound or the Present compound X is mixed with or used in combination with the Present ingredient, they are used simultaneously, separately, or at time intervals with each other.

When the Present compound or the Present compound X is used simultaneously with the Present ingredient, the Present compound or the Present compound X and the Present ingredient may be contained in separate formulations or contained in one formulation.

One aspect of the present invention provides a composition comprising one or more ingredient(s) selected from the group consisting of Group (a) and Group (b), and the Present compound.

One aspect of the present invention provides a composition comprising one or more ingredient(s) selected from the group consisting of Group (a) and Group (b), and the Present compound X (hereinafter referred to as "Composition A").

Group (a) is a group consisting of each active ingredient of acetylcholinesterase inhibitors (for example, carbamate insecticides and organophosphorus insecticides), GABAergic chloride channel antagonists (for example, phenylpyrazole insecticides), sodium channel modulators (for example, pyrethroid insecticides), nicotinic acetylcholine receptor competitive modulators (for example, neonicotinoid insecticides), nicotinic acetylcholine receptor allosteric modulators, glutamatergic chloride channel allosteric modulators (for example, macrolide insecticides), juvenile hormone mimics, multisite inhibitors, chordotonal organ TRPV channel modulators, mites growth inhibitors, mitochondrial ATP biosynthetic enzyme inhibitors, oxidative phosphorylation uncouplers, nicotinic acetylcholine receptor channel blockers (for example, nereistoxin insecticides), chitin synthesis inhibitors, molting inhibitors, ecdysone receptor agonists, octopamine receptor agonists, mitochondrial electron transport system complex I, II, III, and IV inhibitors, voltage-dependent sodium channel blockers, acetyl CoA carboxylase inhibitors, ryanodine receptor modulators (for example, diamide insecticides), chordotonal organmodulators, and microbial insecticides, and other insecticidal active ingredients, miticidal active ingredients, and nematicidal active ingredients. These ingredients are described in the classification on the basis of action mechanism by IRAC.

Group (b) is a group consisting of nucleic acid synthesis inhibitors (for example, phenylamide fungicides and acylamino acid fungicides), cell division and cytoskeleton inhibitors (for example, MBC fungicides), respiration inhibitors (for example, QoI fungicides and QiI fungicides), amino acid synthesis and protein synthesis inhibitors (for example, anilinopyridine fungicides), signaling inhibitors, lipid synthesis and membrane synthesis inhibitors, sterol biosynthesis inhibitors (for example, DMI fungicides such as triazole fungicides), cell-wall synthesis inhibitors, melanin synthesis inhibitors, plant defense inducers, fungicides with multi-site contact activity, microbial fungicides, and other fungicidal active ingredients. These ingredients are described in the classification on the basis of action mechanism by FRAC.

Group (c) is a group of plant growth regulatory ingredients (including mycorrhizal fungi and root nodule bacteria).

Group (d) is a group of phytotoxicity-reducing ingredients.

Group (e) is a group of synergists.

Group (f) is a group of repellent ingredients consisting of bird repellent ingredients, insect repellent ingredients, and animal repellent ingredients.

Group (g) is a group of molluscicidal ingredients.

Group (h) is a group of insect pheromones.

Hereinafter, examples of the combination of the Present ingredient and the Present compound X are described. For example, alanycarb+SX indicates a combination of alanycarb and SX.

The abbreviation of "SX" indicates any one of the Present compounds X selected from the Compound groups SX1 to SX110 described in Examples. Also, all of the following Present ingredients are known ingredients, and may be obtained from commercially available formulations, or may be prepared by known methods. When the Present ingredient is a microorganism, it may also be available from a bacterial authority depository. Further, the number in parentheses represents the CAS RN (registered trademark).

Combination of the Present ingredient in the above Group (a) and the Present compound X:

abamectin+SX, acephate+SX, acequinocyl+SX, acetamiprid+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium cyanide+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, coumaphos+SX, cryolite+SX, cyanophos+SX, cyantraniliprole+SX, cyconiliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dinotefuran+SX, disodium octaborate+SX, disulfoton+SX, DNOC (2-methyl-4,6-dinitrophenol)+SX, doramectin+SX, dried leaves of *Dryopteris filix*-mas+SX, emamectin-benzoate+SX, empenthrin+SX, endosulfan+SX, EPN (O-ethyl 0-(4-nitrophenyl) phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Cassia nigricans*+SX, extract of *Clitoria ternatea*+SX, extract of *Symphytum officinale*+SX, extracts or simulated blend of *Chenopodium ambrosioides*+SX, extract of *Tanacetum vulgare*+SX, extract of *Urtica dioica*+SX, extract of *Viscum album*+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hv1a peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imiprothrin+SX, indoxacarb+SX, isofenphos+SX, isoprocarb+SX, isopropyl-O-(methoxyaminothiophosphoryl)salicylate+SX, isoxathion+SX, ivermectin+SX, kadethrin+SX, kappa-tefluthrin+SX, kappa-bifenthrin+SX, kinoprene+SX, lambda-cyhalothrin+SX, lepimectin+SX, lime sulfur+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methylbromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, potassium cyanide+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, selamectin+SX, sigma-cypermethrin+SX, silafluofen+SX, sodium borate+SX, sodium cyanide+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *Chenopodium ambrosioides* near *ambrosioides* (Brand name: Terpenoid blend QRD 460)+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of *Quassia amara*+SX, XMC (3,5-dimethylphenyl N-methylcarbamate)+SX, xylylcarb+SX, zeta-cypermethrin+SX, zinc phosphide+SX, 3-bromo-N-[2,4-dichloro-6-(methylcarbamoyl) phenyl]-1-(3,5-dichloropyridin-2-yl)-1H-pyrazole-5-carboxamide (1104384-14-6)+SX, N-[3-chloro-1-(pyridin-3-yl)-1H-pyrazol-4-yl]-N-ethyl-3-(3,3,3-trifluoropropanesulfinyl)propaneamide (1477923-37-7)+SX, 4-[5-(3,5-dichlorophenyl)-5-(trifluoromethyl)-4,5-dihydro-1,2-oxazol-3-yl]-2-methyl-N-(1-oxothietan-3-yl) benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propaneamide (1118626-57-5)+SX, N-[2-bromo-6-chloro-4-(1,1,1,2,3,3,3-heptafluoropropan-2-yl)phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-[2-bromo-6-difluoromethoxy-4-(1,1,1,2,3,3,3-heptafluoropropan-2-yl) phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfinyl]phenyl}-3-(trifluoromethyl)-1H-1,2,4-triazole-5-amine (885026-50-6)+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Ab1/Cry35Ab1+SX, *Adoxophyes orana* granulosis virus BV-0001+SX, *Anticarsia gemmatalis* mNPV+SX, *Autographa californica* mNPV+SX, *Cydia pomonella* GV V15+SX, *Cydia pomonella* GV V22+SX, *Cryptophlebia leucotreta* GV+SX, *Dendrolimus punctatus* cypovirus+SX, *Helicoverpa armigera* NPV BV-0003+SX, *Helicoverpa zea* NPV+SX, *Lymantria dispar* NPV+SX, *Mamestra brassicae* NPV+SX, *Mamestra configurata* NPV+SX, *Neodiprion abietis* NPV+SX, *Neodiprion lecon-*

*tei* NPV+SX, *Neodiprion sertifer* NPV+SX, *Nosema locustae*+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, *Arthrobotrys dactyloides*+SX, *Bacillus firmus* GB-126+SX, *Bacillus firmus* I-1582+SX, *Bacillus megaterium*+SX, *Bacillus* sp. AQ175+SX, *Bacillus* sp. AQ177+SX, *Bacillus* sp. AQ178+SX, *Bacillus sphaericus* 2362+SX, *Bacillus sphaericus* ABTS1743+SX, *Bacillus sphaericus* Serotype H5a5b+SX, *Bacillus thuringiensis* AQ52+SX, *Bacillus thuringiensis* BD #32+SX, *Bacillus thuringiensis* CR-371+SX, *Bacillus thuringiensis* subsp. *aizawai* ABTS-1857+SX, *Bacillus thuringiensis* subsp. *aizawai* AM65-52+SX, *Bacillus thuringiensis* subsp. *aizawai* GC-91+SX, *Bacillus thuringiensis* subsp. *aizawai* Serotype H-7+SX, *Bacillus thuringiensis* subsp. *kurstaki* ABTS351+SX, *Bacillus thuringiensis* subsp. *kurstaki* BMP123+SX, *Bacillus thuringiensis* subsp. *kurstaki* EG234+SX, *Bacillus thuringiensis* subsp. *kurstaki* EG7841+SX, *Bacillus thuringiensis* subsp. *kurstaki* EVB113-19+SX, *Bacillus thuringiensis* subsp. *kurstaki* F810+SX, *Bacillus thuringiensis* subsp. *kurstaki* HD-1+SX, *Bacillus thuringiensis* subsp. *kurstaki* PB54+SX, *Bacillus thuringiensis* subsp. *kurstaki* SA-11+SX, *Bacillus thuringiensis* subsp. *kurstaki* SA-12+SX, *Bacillus thuringiensis* subsp. *tenebriosis* NB176+SX, *Bacillus thuringiensis* subsp. *thuringiensis* MPPL002+SX, *Bacillus thuringiensis* subsp. *morrisoni*+SX, *Bacillus thuringiensis* var. *colmeri*+SX, *Bacillus thuringiensis* var. *darmstadiensis* 24-91+SX, *Bacillus thuringiensis* var. *dendrolimus*+SX, *Bacillus thuringiensis* var. *galleriae*+SX, *Bacillus thuringiensis* var. *israelensis* BMP144+SX, *Bacillus thuringiensis* var. *israelensis* serotype H-14+SX, *Bacillus thuringiensis* var. *japonensis buibui*+SX, *Bacillus thuringiensis* var. *san diego* M-7+SX, *Bacillus thuringiensis* var. 7216+SX, *Bacillus thuringiensis* var. *aegypti*+SX, *Bacillus thuringiensis* var. T36+SX, *Beauveria bassiana* ANT-03+SX, *Beauveria bassiana* ATCC74040+SX, *Beauveria bassiana* GHA+SX, *Beauveria brongniartii*+SX, *Burkholderia rinojensis* A396+SX, *Chromobacterium subtsugae* PRAA4-1T+SX, *Dactyllela ellipsospora*+SX, *Dectylaria thaumasia*+SX, *Hirsutella minnesotensis*+SX, *Hirsutella rhossiliensis*+SX, *Hirsutella thompsonii*+SX, *Lagenidium giganteum*+SX, *Lecanicillium lecanii* KV01+SX, *Lecanicillium lecanii* conidia of strain DAOM198499+SX, *Lecanicillium lecanii* conidia of strain DAOM216596+SX, *Metarhizium anisopliae* F52+SX, *Metarhizium anisopliae* var. *acridum*+SX, *Metarhizium flavoviride*+SX, *Monacrosporium phymatopagum*+SX, *Paecilomyces fumosoroseus* Apopka97+SX, *Paecilomyces lilacinus* 251+SX, *Paecilomyces tenuipes* T1+SX, *Paenibacillus popilliae*+SX, *Pasteuria nishizawae* Pn1+SX, *Pasteuria penetrans*+SX, *Pasteuria usgae*+SX, *Pasteuria thoynei*+SX, *Serratia entomophila*+SX, *Verticillium chlamydosporium*+SX, *Verticillium lecani* NCIM1312+SX, lenoremycin+SX, concanamycin A+SX, acetoprole+SX, lotilaner+SX, sarolaner+SX, isocycloseram+SX, *Metarhizium anisopliae* var. *anisopliae* BIPESCO 5/F52+SX, *Lecanicillium muscarium* Ve6+SX, N-ethyl-5-methyl-1-(3-methylbutan-2-yl)-N-(pyridazin-4-yl)-1H-pyrazole-4-carboxamide (1403615-77-9)+SX, imidaclothiz+SX.

Combination of the Present ingredient in the above Group (b) and the Present compound X:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthivalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from *Melaleuca alternifolia*+SX, extract from *Reynoutria sachalinensis*+SX, extract from the cotyledons of lupine plantlets ("BLAD")+SX, extract of *Allium sativum*+SX, extract of *Equisetum arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, *Quillaja* extract+SX, quinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, 3-(difluoromethyl)-N-methoxy-1-methyl-N-[(1R)-1-methyl-2-(2,4,6-trichlorophenyl)ethyl]pyrazole-4-carboxamide (1639015-48-7)+SX, 3-(difluoromethyl)-N-methoxy-1-methyl-N-[(1S)-1-methyl-2-(2,4,6-trichlorophenyl)ethyl]pyrazole-4-carboxamide (1639015-49-8)+SX, 3-(difluoromethyl)-1-methyl-N-(1,1,3-trimethylindan-4-yl)pyrazole-4-carboxamide (141573-94-6)+SX, 3-(difluoromethyl)-N-[(3R)-7-fluoro-1,1,3-trimethylindan-4-yl]-1-methylpyrazole-4-carboxamide (1513466-73-3)+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6)+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo-4-fluorophenyl)-N-(2-chloro-6-fluorophenyl)-1,3-dimethyl-1H-pyrazole-5-amine (1362477-26-6)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidineamine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridine-2-amine (1446247-98-8)+SX, α-[3-(4-chloro-2-fluorophenyl)-5-(2,4-difluorophenyl)-4-isoxazolyl]-3-pyridinemethanol (1229605-96-2)+SX, (αS)-[3-(4-chloro-2-fluorophenyl)-5-(2,4-difluorophenyl)-4-isoxazolyl]-3-pyridinemethanol (1229606-46-5)+SX, (αR)-[3-(4-chloro-2-fluorophenyl)-5-(2,4-difluorophenyl)-4-isoxazolyl]-3-pyridinemethanol (1229606-02-3)+SX, 2-{[3-(2-chlorophenyl)-2-(2,4-difluorophenyl)oxiran-2-yl]methyl}-2,4-dihydro-3H-1,2,4-triazole-3-thione (1342260-19-8)+SX, 2-{[(2R,3S)-3-(2-chlorophenyl)-2-(2,4-difluorophenyl)oxiran-2-yl]methyl}-2,4-dihydro-3H-1,2,4-triazole-3-thione (1638897-70-7)+SX, 2-{[(2S,3R)-3-(2-chlorophenyl)-2-(2,4-difluorophenyl)oxiran-2-yl]methyl}-2,4-dihydro-3H-1,2,4-triazole-3-thione (1638897-71-8)+SX, 2-{[(2R,3R)-3-(2-chlorophenyl)-2-(2,4-difluorophenyl)oxiran-2-yl]methyl}-2,4-dihydro-3H-1,2,4-triazole-3-thione (1638897-72-9)+SX, 2-{[(2S,3S)-3-(2-chlorophenyl)-2-(2,4-difluorophenyl)oxiran-2-yl]methyl}-2,4-dihydro-3H-1,2,4-triazole-3-thione (1638897-73-0)+SX, 1-{[3-(2-chlorophenyl)-2-(2,4-difluorophenyl)oxiran-2-yl]methyl}-1H-1,2,4-triazol-5-yl thiocyanate (1342260-26-7)+SX, 1-{[(2R,3S)-3-(2-chlorophenyl)-2-(2,4-difluorophenyl)oxiran-2-yl]methyl}-1H-1,2,4-triazol-5-yl thiocyanate (1638897-82-1)+SX, 1-{[(2S,3R)-3-(2-chlorophenyl)-2-(2,4-difluorophenyl)oxiran-2-yl]methyl}-1H-1,2,4-triazol-5-yl thiocyanate (1638897-84-3)+SX, 1-{[(2R,3R)-3-(2-chlorophenyl)-2-(2,4-difluorophenyl)oxiran-2-yl]methyl}-1H-1,2,4-triazol-5-yl thiocyanate (1638897-86-5)+SX, 1-{[(2S,3S)-3-(2-chlorophenyl)-2-(2,4-difluorophenyl)oxiran-2-yl]methyl}-1H-1,2,4-triazol-5-yl thiocyanate (1638897-89-8)+SX, 5-(4-chlorobenzyl)-2-chloromethyl-2-methyl-1-(1H-1,2,4-triazol-1-ylmethyl)cyclopentanol (1394057-11-4)+SX, (1R,2S,5S)-5-(4-chlorobenzyl)-2-chloromethyl-2-methyl-1-(1H-1,2,4-triazol-1-ylmethyl)cyclopentanol (1801930-06-2)+SX, (1S,2R,5R)-5-(4-chlorobenzyl)-2-chloromethyl-2-methyl-1-(1H-1,2,4-triazol-1-ylmethyl)cyclopentanol (1801930-07-3)+SX, (1R,2R,5R)-5-(4-chlorobenzyl)-2-chloromethyl-2-methyl-1-(1H-1,2,4-triazol-1-ylmethyl)cyclopentanol (1801919-53-8)+SX, (1S,2S,5S)-5-(4-chlorobenzyl)-2-chloromethyl-2-methyl-1-(1H-1,2,4-triazol-1-ylmethyl)cyclopentanol (1801919-54-9)+SX, (1R,2R,5S)-5-(4-chlorobenzyl)-2-chloromethyl-2-methyl-1-(1H-1,2,4-triazol-1-ylmethyl)cyclopentanol (1801919-55-0)+SX, (1S,2S,5R)-5-(4-chlorobenzyl)-2-chloromethyl-2-methyl-1-(1H-1,2,4-triazol-1-ylmethyl)cyclopentanol (1801919-56-1)+SX, (1R,2S,5R)-5-(4-chlorobenzyl)-2-chloromethyl-2-methyl-1-(1H-1,2,4-triazol-1-ylmethyl)cyclopentanol (1801919-57-2)+SX, (1S,2R,5S)-5-(4-chlorobenzyl)-2-chloromethyl-2-methyl-1-(1H-1,2,4-triazol-1-ylmethyl)cyclopentanol (1801919-58-3)+SX, methyl=3-[(4-chlorophenyl)methyl]-2-hydroxy-1-methyl-2-(1H-1,2,4-triazol-1-ylmethyl)cyclopentanecarboxylate (1791398-02-1)+SX, methyl=(1R,2S,3S)-3-[(4-chlorophenyl)methyl]-2-hydroxy-1-methyl-2-(1H-1,2,4-triazol-1-ylmethyl)cyclopentanecarboxylate (2080743-90-2)+SX, methyl=(1S,2R,3R)-3-[(4-chlorophenyl)methyl]-2-hydroxy-1-methyl-2-(1H-1,2,4-triazol-1-ylmethyl)cyclopentanecarboxylate (2080743-91-3)+SX, methyl=(1R,2R,3R)-3-[(4-chlorophenyl)methyl]-2-hydroxy-1-methyl-2-(1H-1,2,4-triazol-1-ylmethyl)cyclopentanecarboxylate (2080743-92-4)+SX, methyl=(1S,2S,3S)-3-[(4-chlorophenyl)methyl]-2-hydroxy-1-methyl-2-(1H-1,2,4-triazol-1-ylmethyl)cyclopentanecarboxylate (2080743-93-5)+SX, methyl=(1R,2R,3S)-3-[(4-chlorophenyl)methyl]-2-hydroxy-1-methyl-2-(1H-1,2,4-triazol-1-ylmethyl)cyclopentanecarboxylate (2080743-94-6)+SX, methyl=(1S,2S,3R)-3-[(4-chlorophenyl)methyl]-2-hydroxy-1-methyl-2-(1H-1,2,4-triazol-1-ylmethyl)cyclopentanecarboxylate (2080743-95-7)+SX, methyl=(1R,2S,3R)-3-[(4-chlorophenyl)methyl]-2-hydroxy-1-methyl-2-(1H-1,2,4-triazol-1-ylmethyl)cyclopentanecarboxylate (2081061-22-3)+SX, methyl=(1S,2R,3S)-3-[(4-chlorophenyl)methyl]-2-hydroxy-1-methyl-2-(1H-1,2,4-triazol-1-ylmethyl)cyclopentanecarboxylate (2081061-23-4)+SX, 2-chloromethyl-5-(4-fluorobenzyl)-2-methyl-1-(1H-1,2,4-triazol-1-ylmethyl)cyclopentanol (1394057-13-6)+SX, (1R,2S,5S)-2-chloromethyl-5-(4-fluorobenzyl)-2-methyl-1-(1H-1,2,4-triazol-1-ylmethyl)cyclopentanol (1801930-08-4)+SX, (1S,2R,5R)-2-chloromethyl-5-(4-fluorobenzyl)-2-methyl-1-(1H-1,2,4-triazol-1-ylmethyl)cyclopentanol (1801930-09-5)+SX, (1R,2R,5R)-2-chloromethyl-5-(4-fluorobenzyl)-2-methyl-1-(1H-1,2,4-triazol-1-ylmethyl)cyclopentanol (1638898-08-4)+SX, (1S,2S,5S)-2-chloromethyl-5-(4-fluorobenzyl)-2-methyl-1-(1H-1,2,4-triazol-1-ylmethyl)cyclopentanol (1638898-10-8)+SX, (1R,2R,5S)-2-chloromethyl-5-(4-fluorobenzyl)-2-methyl-1-(1H-1,2,4-triazol-1-ylmethyl)cyclopentanol (1638898-13-1)+SX, (S,2S,5R)-2-chloromethyl-5-(4-fluorobenzyl)-2-methyl-1-(1H-1,2,4-triazol-1-ylmethyl)cyclopentanol (1638898-16-

4)+SX, (1R,2S,5R)-2-chloromethyl-5-(4-fluorobenzyl)-2-methyl-1-(1H-1,2,4-triazol-1-ylmethyl)cyclopentanol (1638898-20-0)+SX, (1S,2R,5S)-2-chloromethyl-5-(4-fluorobenzyl)-2-methyl-1-(1H-1,2,4-triazol-1-ylmethyl)cyclopentanol (1638898-24-4)+SX, (R)-2-[2-chloro-4-(4-chlorophenoxy)phenyl]-1-(1,2,4-triazol-1-yl)pent-3-yn-2-ol (1801919-59-4)+SX, (R)-2-[4-(4-chlorophenoxy)-2-(trifluoromethyl)phenyl]-1-(1,2,4-triazol-1-yl)propan-2-ol (1616236-94-2)+SX, (R)-1-[4-(4-chlorophenoxy)-2-(trifluoromethyl)phenyl]-1-cyclopropyl-2-(1,2,4-triazol-1-yl) ethanol (1801919-60-7)+SX, (R)-2-[4-(4-chlorophenoxy)-2-(trifluoromethyl)phenyl]-3-methyl-1-(1,2,4-triazol-1-yl) butan-2-ol (1801919-61-8)+SX, 3-[5-(4-chlorophenyl)-2,3-dimethyl-1,2-oxazolidin-3-yl]pyridine (847749-37-5)+SX, *Agrobacterium radiobacter* K1026+SX, *Agrobacterium radiobacter* K84+SX, *Bacillus amyloliquefaciens* AT332+SX, *Bacillus amyloliquefaciens* B3+SX, *Bacillus amyloliquefaciens* D747+SX, *Bacillus amyloliquefaciens* DB101+SX, *Bacillus amyloliquefaciens* DB102+SX, *Bacillus amyloliquefaciens* GB03+SX, *Bacillus amyloliquefaciens* FZB24+SX, *Bacillus amyloliquefaciens* FZB42+SX, *Bacillus amyloliquefaciens* IN937a+SX, *Bacillus amyloliquefaciens* MBI600+SX, *Bacillus amyloliquefaciens* QST713+SX, *Bacillus amyloliquefaciens* isolate B246+SX, *Bacillus amyloliquefaciens* F727+SX, *Bacillus licheniformis* HB-2+SX, *Bacillus licheniformis* SB3086+SX, *Bacillus pumilus* AQ717+SX, *Bacillus pumilus* BUF-33+SX, *Bacillus pumilus* GB34+SX, *Bacillus pumilus* QST2808+SX, *Bacillus simplex* CGF2856+SX, *Bacillus subtilis* AQ153+SX, *Bacillus subtilis* AQ743+SX, *Bacillus subtilis* BU1814+SX, *Bacillus subtilis* D747+SX, *Bacillus subtilis* DB101+SX, *Bacillus subtilis* FZB24+SX, *Bacillus subtilis* GB03+SX, *Bacillus subtilis* HA10404+SX, *Bacillus subtilis* IAB/BSO3+SX, *Bacillus subtilis* MBI600+SX, *Bacillus subtilis* QST30002/AQ30002+SX, *Bacillus subtilis* QST30004/AQ30004+SX, *Bacillus subtilis* QST713+SX, *Bacillus subtilis* QST714+SX, *Bacillus subtilis* var. *Amyloliquefaciens* FZB24+SX, *Bacillus subtilis* Y1336+SX, *Burkholderia cepacia*+SX, *Burkholderia cepacia* type Wisconsin J82+SX, *Burkholderia cepacia* type Wisconsin M54+SX, *Candida oleophila* O+SX, *Candida saitoana*+SX, *Chaetomium cupreum*+SX, *Clonostachys rosea*+SX, *Coniothyrium minitans* CGMCC8325+SX, *Coniothyrium minitans* CON/M/91-8+SX, *Cryptococcus albidus*+SX, *Erwinia carotovora* subsp. *carotovora* CGE234M403+SX, *Fusarium oxysporum* Fo47+SX, *Gliocladium catenulatum* J1446+SX, *Paenibacillus polymyxa* AC-1+SX, *Paenibacillus polymyxa* BS-0105+SX, *Pantoea agglomerans* E325+SX, *Phlebiopsis gigantea* VRA1992+SX, *Pseudomonas aureofaciens* TX-1+SX, *Pseudomonas chlororaphis* 63-28+SX, *Pseudomonas chlororaphis* MA342+SX, *Pseudomonas fluorescens* 1629RS+SX, *Pseudomonas fluorescens* A506+SX, *Pseudomonas fluorescens* CL145A+SX, *Pseudomonas fluorescens* G7090+SX, *Pseudomonas* sp. CAB-02+SX, *Pseudomonas syringae* 742RS+SX, *Pseudomonas syringae* MA-4+SX, *Pseudozyma flocculosa* PF-A22UL+SX, *Pseudomonas rhodesiae* HAI-0804+SX, *Pythium oligandrum* DV74+SX, *Streptomyces griseoviridis* K61+SX, *Streptomyces lydicus* WYCD108US+SX, *Streptomyces lydicus* WYEC108+SX, *Talaromyces flavus* SAY-Y-94-01+SX, *Talaromyces flavus* V117b+SX, *Trichoderma asperellum* ICC012+SX, *Trichoderma asperellum* SKT-1+SX, *Trichoderma asperellum* T34+SX, *Trichoderma atroviride* CNCM 1-1237+SX, *Trichoderma atroviride* LC52+SX, *Trichoderma atroviride* SC1+SX, *Trichoderma atroviride* SKT-1+SX, *Trichoderma gamsii* ICC080+SX, *Trichoderma harzianum* 21+SX, *Trichoderma harzianum* DB104+SX, *Trichoderma harzianum* DSM 14944+SX, *Trichoderma harzianum* ESALQ-1303+SX, *Trichoderma harzianum* ESALQ-1306+SX, *Trichoderma harzianum* IIHR-Th-2+SX, *Trichoderma harzianum* kd+SX, *Trichoderma harzianum* MO1+SX, *Trichoderma harzianum* SF+SX, *Trichoderma harzianum* T22+SX, *Trichoderma harzianum* T39+SX, *Trichoderma harzianum* TH35+SX, *Trichoderma polysporum* IMI206039+SX, *Trichoderma stromaticum*+SX, *Trichoderma virens* G-41+SX, *Trichoderma virens* GL-21+SX, *Trichoderma viride*+SX, *Variovorax paradoxus* CGF4526+SX, Harpin protein+SX, *Trichoderma harzianum* ITEM908+SX, *Trichoderma harzianum* T78+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, *Bacillus amyloliquefaciens* subsp. *plantarum* D747+SX, *Pythium oligandrum* M1+SX, *Trichoderma asperellum* T25+SX, *Trichoderma asperellum* TV1+SX, *Trichoderma atroviride* IMI 206040+SX, *Trichoderma atroviride* T11+SX, *Bacillus amyloliquefaciens* (Aveo (trademark) EZ Nematicide)+SX.

Combination of the Present ingredient in the above Group (c) and the Present compound X:

1-methylcyclopropene+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, Gibberellin A+SX, Gibberellin A3+SX, inabenfide+SX, Kinetin+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide(2-(naphthalene-1-yl)acetamide)+SX, [4-oxo-4-(2-phenylethyl)amino]butyric acid+SX, methyl 5-(trifluoromethyl)benzo[b]thiophene-2-carboxylate+SX, 3-[(6-chloro-4-phenylquinazolin-2-yl) amino]-1-propanol+SX, formononetin+SX, *Glomus intraradices*+SX, *Glomus mosseae*+SX, *Glomus aggregatum*+SX, *Glomus etunicatum*+SX, *Bradyrhizobium elkani*+SX, *Bradyrhizobium japonicum*+SX, *Bradyrhizobium lupini*+SX, *Rhizobium leguminosarum* bv. *trifolii*+SX, *Rhizobium leguminosarum* bv. *phaseoli*+SX, *Rhizobium leguminosarum* bv. *viciae*+SX, *Sinorhizobium meliloti*+SX, *Rhizobium fredii*+SX, *Rhizobium loti*+SX, *Rhizobium trifolii*+SX, *Rhizobium tropici*+SX, 1,3-diphenylurea+SX,

*Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Delftia acidovorans* RAY209+SX, *Gigaspora margarita*+SX, *Gigaspora rosea*+SX, *Glomus deserticola*+SX, *Glomus monosporum*+SX, *Mesorhizobium ciceri*+SX, *Mesorhizobium huakii*+SX, *Rhizophagus clarus*+SX, *Rhizobium etli*+SX, *Rhizobium galegae*+SX, *Rhizophagus irregularis* DAOM 197198+SX, *Paraglomus brasillianum*+SX, *Claroideoglomus claroideum*+SX, lipochitooligosaccharide SP104+SX, Zucchini Yellow Mosaik Virus weak strain+SX.

Combination of the Present ingredient in the above Group (d) and the Present compound X:

allidochlor+SX, benoxacor+SX, cloquintocet+SX, cloquintocet-mexyl+SX, cyometrinil+SX, cyprosulfamide+SX, dichlormid+SX, dicyclonone+SX, dimepiperate+SX, disulfoton+SX, dymron+SX, fenchlorazole+SX, fenchlorazole-ethyl+SX, fenclorim+SX, flurazole+SX, furilazole+SX, fluxofenim+SX, Hexim+SX, isoxadifen+SX, isoxadifen-ethyl+SX, mecoprop+SX, mefenpyr+SX, mefenpyr-ethyl+SX, mefenpyr-diethyl+SX, mephenate+SX, metcamifen+SX, oxabetrinil+SX, 1,8-naphthalic anhydride+SX, 1,8-octamethylene diamine+SX, AD-67 (4-(dichloroacetyl)-1-oxa-4-azaspiro[4.5]decane)+SX, CL-304415 (4-carboxy-3,4-dihydro-2H-1-benzopyran-4-acetic acid)+SX, CSB (1-bromo-4-[(chloromethyl)sulfonyl]benzene)+SX, DKA-24 (2,2-dichloro-N-[2-oxo-2-(2-propenylamino)ethyl]-N-(2-propenyl)acetamide)+SX, MG191 (2-(dichloromethyl)-2-methyl-1,3-dioxolane)+SX, MG-838 (2-propenyl 1-oxa-4-azaspiro[4.5]decane-4-carbodithioate)+SX, PPG-1292 (2,2-dichloro-N-(1,3-dioxan-2-ylmethyl)-N-(2-propenyl)acetamide)+SX, R-28725 (3-(dichloroacetyl)-2,2-dimethyl-1,3-oxazolidine)+SX, R-29148 (3-(dichloroacetyl)-2,2,5-trimethyl-1,3-oxazolidine)+SX, TI-35 (1-(dichloroacetyl)azepane)+SX.

Combination of the Present ingredient in the above Group (e) and the Present compound X:

1-dodecyl-1H-imidazole+SX, N-(2-ethylhexyl)-8,9,10-trinorborn-5-ene-2,3-dicarboximide+SX, bucarpolate+SX, N,N-dibutyl-4-chlorobenzenesulfonamide+SX, dietholate+SX, diethylmaleate+SX, piperonyl butoxide+SX, piperonyl cyclonene+SX, piprotal+SX, propyl isome+SX, safroxan+SX, sesamex+SX, sesamolin+SX, sulfoxide+SX, Verbutin+SX, DMC (1,1-bis(4-chlorophenyl)ethanol)+SX, FDMC (1,1-bis(4-chlorophenyl)-2,2,2-trifluoroethanol)+SX, ETN (1,2-epoxy-1,2,3,4-tetrahydronaphthalene)+SX, ETP (1,1,1-trichloro-2,3-expoxypropane)+SX, PSCP (phenylsaligenin cyclic phosphate)+SX, TBPT (S,S,S-tributyl phosphorotrithioate)+SX, TPP (triphenyl phosphate)+SX.

Combination of the Present ingredient in the above Group (f) and the Present compound X:

anthraquinone+SX, chloralose+SX, acrep+SX, butopyronoxyl+SX, camphor+SX, d-camphor+SX, carboxide+SX, dibutyl phthalate+SX, deet+SX, dimethylcarbate+SX, dimethylphthalate+SX, dibutyl succinate+SX, dibutyl adipate+SX, ethohexadiol+SX, hexamide+SX, icaridin+SX, methoquin-butyl+SX, methylneodecanamide+SX, 2-(octylthio)ethanol+SX, butoxypolypropylene glycol+SX, oxamate+SX, quwenzhi+SX, quyingding+SX, zengxiaon+SX, rebemide+SX, copper naphthenate+SX, zinc naphthenate+SX.

Combination of the Present ingredient in the above Group (g) and the Present compound X:

bis(tributyltin) oxide+SX, allicin+SX, bromoacetamide+SX, cloethocarb+SX, copper sulfate+SX, fentin+SX, ferric phosphate+SX, metaldehyde+SX, niclosamide+SX, pentachlorophenol+SX, sodium pentachlorophenoxide+SX, tazimcarb+SX, tralopyril+SX, trifenmorph+SX.

Combination of the Present ingredient in the above Group (h) and the Present compound X:

(E)-2-hexenal+SX, (E)-2-octadecenal+SX, (E)-4-tridecen-1-yl acetate+SX, (E)-5-decen-1-yl acetate+SX, (E)-5-decen-1-ol+SX, (E)-3,3-dimethylcyclohexylideneacetaldehyde+SX, (E)-7-dodecen-1-yl acetate+SX, (E)-8-dodecen-1-yl acetate+SX, (E)-9-dodecen-1-yl acetate+SX, (E)-10-hexadecenal+SX, (E)-11-hexadecen-1-yl acetate+SX, (E)-11-tetradecen-1-yl acetate+SX, (E)-11-tetradecen-1-ol+SX, (E)-4-tridecen-1-yl acetate+SX, (E)-6-methylhept-2-en-4-ol+SX, (Z)-2-(3,3-dimethylcyclohexylidene)ethanol+SX, (Z)-4-decen-1-yl acetate+SX, (Z)-4-tridecen-1-yl acetate+SX, (Z)-5-decen-1-yl acetate+SX, (Z)-5-decen-1-ol+SX, (Z)-7-tetradecenal+SX, (Z)-7-dodecen-1-yl acetate+SX, (Z)-8-dodecen-1-yl acetate+SX, (Z)-9-dodecen-1-yl acetate+SX, (Z)-8-dodecen-1-ol+SX, (Z)-9-hexadecenal+SX, (Z)-10-hexadecen-1-yl acetate+SX, (Z)-11-hexadecen-1-ol+SX, (Z)-11-hexadecenal+SX, (Z)-11-hexadecen-1-yl acetate+SX, (Z)-11-octadecenal+SX, (Z)-13-octadecenal+SX, (Z)-hexadec-13-en-11-yn-1-yl acetate+SX, (Z)-13-octadecenal+SX, (Z)-icos-13-en-10-one+SX, (Z)-7-tetradecenal+SX, (Z)-tetradec-9-en-1-ol+SX, (Z)-9-tetradecen-1-yl acetate+SX, (Z)-11-tetradecen-1-yl acetate+SX, (Z)-13-icosen-10-one+SX, (Z,E)-7,11-hexadecadien-1-yl acetate+SX, (Z,E)-9,12-tetradecadien-1-yl acetate+SX, (E,Z)-4,10-tetradecadien-1-yl acetate+SX, (E,E)-8,10-dodecadien-1-ol+SX, (E,E)-10,12-hexadecadienal+SX, (E,E)-9,11-tetradecadien-1-yl acetate+SX, (E,Z)-2,13-octadecadien-1-ol+SX, (E,Z)-3,13-octadecadien-1-ol+SX, (E,Z)-2,13-octadecadien-1-yl acetate+SX, (E,Z)-3,13-octadecadien-1-yl acetate+SX, (E,Z)-7,9-dodecadien-1-yl acetate+SX, (E,E)-7,9-dodecadien-1-yl acetate+SX, (Z,E)-9,12-tetradecadien-1-yl acetate+SX, (Z,E)-9,11-tetradecadien-1-yl acetate+SX, (Z,E)-7,11-hexadecadien-1-yl acetate+SX, (Z,Z)-3,13-octadecadien-1-ol+SX, (Z,Z)-4,7-decadien-1-yl acetate+SX, (Z,Z)-3,13-octadecadien-1-yl acetate+SX, (Z,Z)-7,11-hexadecadien-1-yl acetate+SX, (Z,Z,E)-7,11,13-hexadecatrienal+SX, (5R)-5-[(1Z)-1-decen-1-yl]dihydro-2(3H)-furanone+SX, (2R,5R)-ethyl-1,6-dioxaspiro[4,4]nonane+SX, (2R,5S)-ethyl-1,6-dioxaspiro[4,4]nonane+SX, (4R,8R)-4,8-dimethyldecanal+SX, (4R,8S)-4,8-dimethyldecanal+SX, 2,4-dimethyl-5-ethyl-6,8-dioxabicyclo[3,2,1]octane+SX, (−)-4-methyl-3-heptanol+SX, 1,7-dioxaspiro[5,5]undecane+SX, 3-carene+SX, 3-methylcyclohex-2-en-1-one+SX, 14-methyloctadec-1-ene+SX, 4-methylnonan-5-ol+SX, 4-methylnonan-5-one+SX, 4-(3-oxobutyl)phenyl acetate+SX, dodecyl acetate+SX, dodeca-8,10-dien-1-yl acetate+SX, ethyl (2E,4Z)-decadienoate+SX, ethyl 4-methyloctanoate+SX, methyl 2,6,10-trimethyldodecanoate+SX, tetradecan-1-ol+SX, tetradec-11-en-1-ol+SX, tetradec-11-en-1-yl acetate+SX, tridec-4-en-1-yl acetate+SX, (3S,6R)-3-methyl-6-isopropenyl-9-decen-1-yl acetate+SX, (3S,6S)-3-methyl-6-isopropenyl-9-decen-1-yl acetate+SX, alpha-multistriatin+SX, alpha-pinene+SX, endo-brevicomin+SX, exo-brevicomin+SX, camphene+SX, codlelure+SX, codlemone+SX, cuelure+SX, disparlure+SX, dominicalure+SX, eugenol+SX, farnesol+SX, ferrolure+SX, frontalin+SX, gossyplure+SX, grandlure+SX, grandlure I+SX, grandlure II+SX, grandlure III+SX, grandlure IV+SX, hexalure+SX, ipsdienol+SX, ipsenol+SX, japonilure+SX, lineatin+SX, litlue+SX, looplure+SX, medlure+SX, megatomoic acid+SX, methyleugenol+SX, muscalure+SX, nerolidol+SX, orfralure+SX, oryctalure+SX, ostramone+SX, rhyncolure+SX, siglure+SX, sordidin+SX, sulcatol+SX, trimedlure+SX, trimedlure A+SX, trimedlure B1+SX, trimedlure B2+SX, trimedlure C+SX, trunc-call+SX, (E)-verbenol+SX, (Z)-verbenol+SX, trans-verbenol+SX, (S)-verbenone+SX.

Examples of the mixture ratio of the Present compound X and the Present ingredient include, but are not limited to, 1000:1 to 1:1000, 500:1 to 1:500, 100:1 to 1:100, 50:1 to 1:50, 20:1 to 1:20, 10:1 to 1:10, 3:1 to 1:3, 1:1 to 1:500, 1:1 to 1:100, 1:1 to 1:50, 1:1 to 1:20, and 1:1 to 1:10 in the ratio by weight (Present compound X: Present ingredient).

The Present compounds or the Present compounds X have control effects on harmful arthropods such as harmful insects and harmful mites, harmful nematodes, and harmful mollusks. Examples of the harmful arthropods, harmful nematodes, and harmful mollusks include the followings.

Hemiptera:

from the family Delphacidae, for example, small brown planthopper (*Laodelphax striatellus*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), and *Tagosodes orizicolus;* from the family Cicadellidae, for example, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), and rice leafhopper (*Cofana spectra*);

from the family Cercopidae, for example, *Mahanarva posticata* and *Mahanarva fimbriolata;* from the family Aphididae, for example, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), and apple woolly aphid (*Eriosoma lanigeruin*);

from the family Phylloxeridae, for example, grapevine phylloxera (*Daktulosphaira vitifoliae*), Pecan *phylloxera* (*Phylloxera devastatrix*), Pecan leaf *phylloxera* (*Phylloxera notabilis*), and Southern pecan leaf *phylloxera* (*Phylloxera russellae*);

from the family Adelgidae, for example, hemlock woolly aphid (*Adelges tsugae*), *Adelges piceae*, and *Aphrastasia pectinatae;* from the family Pentatomidae, for example, black rice bug (*Scotinophara lurida*), Malayan rice black bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris annamita*, brown marmorated stink bug (*Halyomorpha halys*), green plant bug (*Nezara viridula*), Brown stink bug (*Euschistus heros*), Red banded stink bug (*Piezodorus guildinii*), *Oebalus pugnax*, and *Dichelops melacanthus;* from the family Cydnidae, for example, Burrower brown bug (*Scaptocoris castanea*);

from the family Alydidae, for example, bean bug (*Riptortus pedestris*), corbett rice bug (*Leptocorisa chinensis*), and rice bug (*Leptocorisa acuta*);

from the family Coreidae, for example, *Cletus punctiger* and Australian leaf-footed bug (*Leptoglossus australis*);

from the family Lygaeidae, for example, oriental chinch bug (*Caverelius saccharivorus*), seed bug (Togo hemipterus), and chinch bug (*Blissus leucopterus*);

from the family Miridae, for example, rice leaf bug (*Trigonotylus caelestialium*), sorghum plant bug (*Stenotus rubrovittatus*), wheat leaf bug (*Stenodema calcarata*), and American tarnished plant bug (*Lygus lineolaris*);

from the family Aleyrodidae, for example, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), and *Pealius euryae;* from the family Diaspididae, for example, *Abgrallaspis cyanophylli*, red scale (*Aonidiella aurantii*), San José scale (*Diaspidiotus perniciosus*), white peach scale (*Pseudaulacaspis pentagona*), arrowhead scale (*Unaspis yanonensis*), and citrus snow scale (*Unaspis citri*);

from the family Coccidae, for example, pink wax scale (*Ceroplastes rubens*);

from the family Margarodidae, for example, fluted scale (*Icerya purchasi*) and seychelles fluted scale (*Icerya seychellarum*);

from the family Pseudococcidae, for example, *solanum* mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), and tuttle mealybug (*Brevennia rehi*);

from the family Psyllidae, for example, citrus *psylla* (*Diaphorina citri*), two-spotted citrus psyllid (*Trioza erytreae*), pear sucker (*Cacopsylla pyrisuga*), *Cacopsylla chinensis*, potato psyllid (*Bactericera cockerelli*), and Pear psylla (*Cacopsylla pyricola*);

from the family Tingidae, for example, sycamore lace bug (*Corythucha ciliata*), aster tingid (*Corythucha marmorata*), Japanese pear lace bug (*Stephanitis nashi*), and azalea lace bug (*Stephanitis pyrioides*);

from the family Cimicidae, for example, common bed bug (*Cimex lectularius*);

from the family Cicadidae, for example, Giant Cicada (*Quesada gigas*);

*Triatoma* spp. (such as *Triatoma infestans*);

and the others.

Lepidoptera:

from the family Crambidae, for example, rice stem borer (*Chilo suppressalis*), Dark-headed stem borer (*Chilo polychrysus*), white stem borer (*Scirpophaga innotata*), yellow paddy borer (*Scirpophaga incertulas*), *Rupela albina*, rice leaf roller (*Cnaphalocrocis medinalis*), *Marasmia patnalis*, rice leaf roller (*Marasmia exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma luctuosale*), bluegrass webworm (*Pediasia teterrellus*), rice case-worm (*Nymphula depunctalis*), and Sugarcane borer (*Diatraea saccharalis*);

from the family Pyralidae, for example, lesser cornstalk borer (*Elasmopalpus lignosellus*), mealworm moth (*Plodia interpunctella*), and persimmon bark borer (*Euzophera batangensis*);

from the family Noctuidae, for example, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), black cutworm (*Agrotis ipsilon*), beet worm (*Autographa nigrisigna*), rice looper (*Plusia festucae*), soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*) and corn earworm (*Helicoverpa zea*)), Velvetbean caterpillar (*Anticarsia gemmatalis*), Cotton leafworm (*Alabama argillacea*), and Hop vine borer (*Hydraecia immanis*);

from the family Pieridae, for example, common cabbage worm (*Pieris rapae*);

from the family Tortricidae, for example, oriental fruit moth (*Grapholita molesta*), *Grapholita dimorpha*, soybean moth (*Leguminivora glycinivorella*), *Matsumuraeses azukivora*, summer fruit tortrix (*Adoxophyes orana fasciata*), smaller tea tortrix (*Adoxophyes honmai*), Japanese tea tortrix (*Homona magnanima*), apple tortrix (*Archips fuscocupreanus*), codling moth (*Cydia pomonella*), sugarcane shoot borer (*Tetramoera schistaceana*), Bean Shoot Borer (*Epinotia aporema*), and Citrus fruit borer (*Ecdytolopha aurantiana*);

from the family Gracillariidae, for example, tea leaf roller (*Caloptilia theivora*) and Asiatic apple leaf miner (*Phyllonorycter ringoniella*);

from the family Carposinidae, for example, peach fruit moth (*Carposina sasakii*);

from the family Lyonetiidae, for example, Coffee Leaf miner (*Leucoptera coffeella*), peach leaf miner (*Lyonetia clerkella*), and *Lyonetia prunifoliella*;

from the family Lymantriidae, for example, *Lymantria* spp. (such as gypsy moth (*Lymantria dispar*)) and *Euproctis* spp. (such as tea lymantriid (*Euproctis pseudoconspersa*));

from the family Plutellidae, for example, diamondback moth (*Plutella xylostella*);

from the family Gelechiidae, for example, peach worm (*Anarsia lineatella*), sweetpotato leaf folder (*Helcystogramma triannulella*), pink bollworm (*Pectinophora gossypiella*), potato moth (*Phthorimaea operculella*), and *Tuta absoluta*;

from the family Arctiidae, for example, American white moth (*Hyphantria cunea*);

from the family Castniidae, for example, Giant Sugarcane borer (*Telchin licus*);

from the family Cossidae, for example, *Cossus insularis*;

from the family Geometridae, for example, *Ascotis selenaria*;

from the family Limacodidae, for example, blue-striped nettle grub (*Parasa lepida*);

from the family Stathmopodidae, for example, persimmon fruit moth (*Stathmopoda masinissa*);

from the family Sphingidae, for example, tobacco hornworm (*Acherontia lachesis*);

from the family Sesiidae, for example, *Nokona feralis*, cherry borer (*Synanthedon hector*), and *Synanthedon tenuis*:

from the family Hesperiidae, for example, rice skipper (*Parnara guttata*);

from the family Tineidae, for example, casemaking clothes moth (*Tinea translucens*) and common clothes moth (*Tineola bisselliella*);

and the others.

Thysanoptera:

from the family Thripidae, for example, western flower thrips (*Frankliniella occidentalis*), oriental thrips (*Thrips palmi*), yellow tea thrips (*Scirtothrips dorsalis*), onion thrips (*Thrips tabaci*), eastern flower thrips (*Frankliniella intonsa*), rice thrips (*Stenchaetothrips biformis*), and *Echinothrips americanus*;

from the family Phlaeothripidae, for example, aculeated rice thrips (*Haplothrips aculeatus*);

and the others.

Diptera:

from the family Anthomyiidae, for example, seedcorn maggot (*Delia platura*), onion maggot (*Delia antiqua*), and beet leaf miner (*Pegomya cunicularia*);

from the family Ulidiidae, for example, sugarbeet root maggot (*Tetanops myopaeformis*);

from the family Agromyzidae, for example, rice leaf miner (*Agromyza oryzae*), tomato leaf miner (*Liriomyza sativae*), chrysanthemum leaf miner (*Liriomyza trifolii*), and pea leafminer (*Chromatomyia horticola*);

from the family Chloropidae, for example, rice stem maggot (*Chlorops oryzae*);

from the family Tephritidae, for example, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*), Mediterranean fruit fly (*Ceratitis capitata*), apple maggot (*Rhagoletis pomonella*), and Japanese cherry fruit fly (*Rhacochlaena japonica*);

from the family Ephydridae, for example, smaller rice leaf miner (*Hydrellia griseola*), whorl maggot (*Hydrellia philippina*), and paddy stem maggot (*Hydrellia sasakii*);

from the family Drosophilidae, for example, cherry drosophila (*Drosophila suzukii*);

from the family Phoridae, for example, *Megaselia spiracularis*;

from the family Psychodidae, for example, *Clogmia albipunctata*;

from the family Sciaridae, for example, *Bradysia difformis*;

from the family Cecidomyiidae, for example, hessian fly (*Mayetiola destructor*) and paddy gall fly (*Orseolia oryzae*);

from the family Diopsidae, for example, *Diopsis macrophthalma*;

from the family Tipulidae, for example, rice crane fly (*Tipula aino*), Common cranefly (*Tipula oleracea*), and European cranefly (*Tipula paludosa*);

from the family Culicidae, for example, southern house mosquito (*Culex pipiens pallens*), dengue mosquito (*Aedes aegypti*), Asian tiger mosquito (*Aedes albopictus*), Chinese malaria mosquito (*Anopheles hyracanus sinensis*), *Culex quinquefasciatus*, *Culex pipiens molestus Forskal*, and brown house mosquito (*Culex quinquefasciatus*);

from the family Simulidae, for example, *Prosimulium yezoensis* and *Simulium ornatum*;

from the family Tabanidae, for example, *Tabanus trigonus*;

from the family Muscidae, for example, house fly (*Musca domestica*), false stable fly (*Muscina stabulans*), biting house fly (*Stomoxys calcitrans*), and buffalo fly (*Haematobia irritans*);

from the family Calliphoridae;

from the family Sarcophagidae;

from the family Chironomidae, for example, *Chironomus plumosus, Chironomus yoshimatsui,* and *Glyptotendipes tokunagai;* from the family Fannidae;

and the others.

Coleoptera:

from the family Chrysomelidae, for example, western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), Cucurbit Beetle (*Diabrotica speciosa*), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), Cabbage flea beetle (*Phyllotreta cruciferae*), Western black flea beetle (*Phyllotreta pusilla*), Cabbage stem flea beetle (*Psyllioodes chrysocephala*), Colorado potato beetle (*Leptinotarsa decemlineata*), rice leaf beetle (*Oulema oryzae*), grape *colaspis* (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (*Dicladispa armigera*), southern corn leaf beetle (*Myochrous denticollis*), *Laccoptera quadrimaculata,* and tobacco flea beetle (*Epitrix hirtipennis*);

from the family Carabidae, for example, Seedcorn beetle (*Stenolophus lecontei*) and slender seed-corn ground beetle (*Clivina impressifrons*);

from the family Scarabaeidae, for example, cupreus chafer (*Anomala cuprea*), soybean beetle (*Anomala rufocuprea*), *Anomala albopilosa,* Japanese beetle (*Popillia japonica*), yellowish elongate chafer (*Heptophylla picea*), European Chafer (*Rhizotrogus majalis*), *Tomarus gibbosus, Holotrichia* spp., *Phyllophaga* spp. (such as June beetle (*Phyllophaga crinita*)), and *Diloboderus* spp. (such as *Diloboderus abderus*);

from the family Curculionidae, for example, coffee bean weevil (*Araecerus coffeae*), sweet-potato weevil (*Cylas formicarius*), West Indian sweet-potato weevil (*Euscepes postfasciatus*), alfalfa weevil (*Hypera postica*), maize wevil (*Sitophilus zeamais*), rice plant weevil (*Echinocnemus squameus*), rice water weevil (*Lissorhoptrus oryzophilus*), *Rhabdoscelus lineatocollis,* boll weevil (*Anthonomus grandis*), nunting billbug (*Sphenophorus venatus*), Southern Corn Billbug (*Sphenophorus callosus*), Soybean stalk weevil (*Sternechus subsignatus*), Sugarcane weevil (*Sphenophorus levis*), rusty gourd-shaped weevil (*Scepticus griseus*), brown gourd-shaped weevil (*Scepticus uniformis*), Mexican bean weevil (*Zabrotes subfasciatus*), pine beetle (*Tomicus piniperda*), Coffee Berry Borer (*Hypothenemus hampei*), *Aracanthus* spp. (such as *Aracanthus mourei*), and cotton root borer (*Eutinobothrus brasiliensis*);

from the family Tenebrionidae, for example, red meal beetle (*Tribolium castaneum*) and mason beetle (*Tribolium confusum*);

from the family Coccinellidae, for example, twenty-eight-spotted ladybird (*Epilachna vigintioctopunctata*); from the family Bostrychidae, for example, common powder-post beetle (*Lyctus brunneus*);

from the family Ptinidae;

from the family Cerambycidae, for example, citrus long-horned beetle (*Anoplophora malasiaca*) and *Migdolus fryanus;* from the family Elateridae, for example, *Melanotus okinawensis,* barley wireworm (*Agriotes fuscicollis*), *Melanotus legatus, Anchastus* spp., *Conoderus* spp., *Ctenicera* spp., *Limonius* spp., and *Aeolus* spp.; from the family Staphylinidae, for example, *Paederus fuscipes;* from the family Dermestidae, for example, varied carpet beetle (*Anthrenus verbasci*) and hide beetle (*Dermestes maculates*);

from the family Anobiidae, for example, tobacco beetle (*Lasioderma serricorne*) and biscuit beetle (*Stegobium paniceum*);

and the others.

Orthoptera:

from the family Acrididae, for example, oriental migratory locust (*Locusta migratoria*), Moroccan locust (*Dociostaurus maroccanus*), Australian plague locust (*Chortoicetes terminifera*), red locust (*Nomadacris septemfasciata*), Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), desert locust (*Schistocerca gregaria*), Yellow-winged locust (*Gastrimargus musicus*), Spur-throated locust (*Austracris guttulosa*), Japanese grasshopper (*Oxya yezoensis*), rice grasshopper (*Oxya japonica*), and Bombay locust (*Patanga succincta*);

from the family Gryllotalpidae, for example, oriental mole cricket (*Gryllotalpa orientalis*);

from the family Gryllidae, for example, house cricket (*Acheta domestica*) and emma field cricket (*Teleogryllus emma*);

from the family Tettigoniidae, for example, Mormon cricket (*Anabrus simplex*);

and the others.

Hymenoptera:

from the family Tenthredinidae, for example, beet sawfly (*Athalia rosae*) and nippon cabbage sawfly (*Athalia japonica*);

from the family Formicidae, for example, *Solenopsis* spp. (such as red imported fire ant (*Solenopsis invicta*) and tropical fire ant (*Solenopsis geminata*)), *Atta* spp. (such as Brown leaf-cutting ant (*Atta capiguara*)), *Acromyrmex* spp., *Paraponera clavata,* black house ant (*Ochetellus glaber*), little red ant (*Monomorium pharaonis*), Argentine ant (*Linepithema humile*), *Formica fusca japonica, Pristomyrmex punctutus, Pheidole* noda, big-headed ant (*Pheidole megacephala*), *Camponotus* spp. (such as *Camponotus japonicus* and *Camponotus obscuripes*), *Pogonomyrmex* spp. (such as western harvester ant (*Pogonomyrmex occidentalis*)), *Wasmania* spp. (such as *Wasmania auropunctata*), and long-legged ant (*Anoplolepis gracilipes*);

from the family Vespidae, for example, Asian giant hornet (*Vespa mandarinia japonica*), *Vespa simillima, Vespa analis Fabriciusi,* Asian hornet (*Vespa velutina*), and *Polistes jokahamae;* from the family Siricidae, for example, pine wood wasp (*Urocerus gigas*);

from the family Bethylidae;

and the others.

Blattodea:

from the family Blattellidae, for example, German cockroach (*Blattella germanica*);

from the family Blattidae, for example, smoky-brown cockroach (*Periplaneta fuliginosa*), American cockroach (*Periplaneta americana*), brown cockroach (*Periplaneta brunnea*), and black cockroach (*Blatta orientalis*);

from the family Termitidae, for example, Japanese termite (*Reticulitermes speratus*), Formosan termite (*Coptotermes*

*formosanus*), western drywood termite (*Incisitermes minor*), *Cryptotermes domesticus*, *Odontotermes formosanus*, *Neotermes koshunensis*, *Glyptotermes satsumensis*, *Glyptotermes nakajimai*, *Glyptotermes fuscus*, *Hodotermopsis sjostedti*, *Coptotermes guangzhouensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, and *Cornitermes cumulans*; and the others.

Siphonaptera:

cat flea (*Ctenocephalides felis*), dog flea (*Ctenocephalides canis*), human flea (*Pulex irritans*), oriental rat flea (*Xenopsylla cheopis*), chigoe flea (*Tunga penetrans*), chicken flea (*Echidnophaga gallinacea*), and European rat flea (*Nosopsyllus fasciatus*);

and the others.

Anoplura:

pig louse (*Haematopinus suis*), short-nosed cattle louse (*Haematopinus eurysternus*), *Dalmalinia ovis*, *Linognathus seypsus*, *Pediculus humanis*, *Pediculuc humanus corporis*, *Pediculus humanus humanus*, and *Phthirus pubis*; and the others.

Mallophagida:

*Bovicola* spp. (such as *Dalmalinia bovis* and *Dalmalinia ovis*), *Trichodectes* spp. (such as *Trichodectes canis*), *Felocpla* spp. (such as *Felicola subrostrata*), and *Lipeurus* spp. (such as *Lipeurus caponis*);

from the family Menoponidae, for example, *Trimenopon* spp. and *Menopon* spp.;

and the others.

Acari:

from the family Tetranychidae, for example, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), and *Oligonychus* spp.;

from the family Eriophyidae, for example, Japanese citrus rust mite (*Aculops pelekassi*), *Phyllocoptruta citri*, tomato mite (*Aculops lycopersici*), purple mite (*Calacarus carinatus*), tea rust mite (*Acaphylla theavagrans*), *Eriophyes chibaensis*, apple bud mite (*Aculus schlechtendali*), *Aceria diospyri*, *Aceria tosichella*, and *Shevtchenkella* sp.;

from the family Tarsonemidae, for example, broad mite (*Polyphagotarsonemus latus*);

from the family Tenuipalpidae, for example, *Brevipalpus phoenicis*;

from the family Tuckerellidae;

from the family Ixodidae, for example, *Haemaphysalis longicornis*, *Haemaphysalis flava*, *Dermacentor taiwanensis*, American dog tick (*Dermacentor variabilis*), *Dermacentor andersoni*, *Ixodes ovatus*, *Ixodes persulcatus*, *Ixodes ricinus*, black-legged tick (*Ixodes scapularis*), lone star tick (*Amblyomma americanum*), gulf coast tick (*Amblyomma maculatuin*), *Boophilus microplus*, *Boophilus annulatus*, and brown dog tick (*Rhipicephalus sanguineus*);

from the family Acaridae, for example, cereal mite (*Tyrophagus putrescentiae*) and grassland mite (*Tyrophagus similis*);

from the family Pyroglyphidae, for example, American house dust mite (*Dermatophagoides farinae*) and European house dust mite (*Dermatophagoides pteronyssinus*);

from the family Cheyletidae, for example, *Cheyletus eruditus*, *Cheyletus malaccensis*, *Cheyletus moorei*, and *Cheyletiella yasguri*;

from the family Sarcoptidae, for example, mange mite (*Otodectes cynotis*) and itch mite (*Sarcoptes scabiei*);

from the family Demodicidae, for example, dog follicle mite (*Demodex canis*);

from the family Listrophoridae;

from the family Haplochthoniidae;

from the family Macronyssidae, for example, tropical rat mite (*Ornithonyssus bacoti*) and feather mite (*Ornithonyssus sylviarum*);

from the family Dermanyssidae, for example, bird mite (*Dermanyssus gallinae*);

from the family Trombiculidae, for example, *Leptotrombidium akamushi*;

and the others.

Araneae:

from the family Eutichuridae, for example, *Cheiracanthium japonicum*;

from the family Theridiidae, for example, red-back spider (*Latrodectus hasseltii*);

and the others.

Polydesmida:

from the family Paradoxosomatidae, for example, flat-backed millipede (*Oxidus gracilis*) and *Nedyopus tambanus*;

and the others.

Isopoda:

from the family Armadillidiidae, for example, common pill bug (*Armadillidium vulgare*);

and the others.

Chilopoda:

from the family Scutigeridae, for example, *Thereuonema hilgendorfi*;

from the family Scolopendridae, for example, giant tropical centipede (*Scolopendra subspinipes*);

from the family Ethopolyidae, for example, *Bothropolys rugosus*;

and the others.

Gastropoda:

from the family Limacidae, for example, tree slug (*Limax marginatus*) and garden tawny slug (*Limax flavus*);

from the family Philomycidae, for example, *Meghimatium bilineatum*;

from the family Ampullariidae, for example, golden apple snail (*Pomacea canaliculata*);

from the family Lymnaeidae, for example, *Austropeplea ollula*;

and the others.

Nematoda:

from the family Aphelenchoididae, for example, rice white-tip nematode (*Aphelenchoides besseyi*);

from the family Pratylenchidae, for example, root lesion nematode (*Pratylenchus coffeae*), *Pratylenchus* brachyurus, California meadow nematode (*Pratylenchus neglectus*), and *Radopholus similis*;

from the family Heteroderidae, for example, javanese root-knot nematode (*Meloidogyne javanica*), southern root-knot nematode (*Meloidogyne incognita*), northern root-knot nematode (*Meloidogyne hapla*), soybean cyst nematode (*Heterodera glycines*), potato cyst nematode (*Globodera rostochiensis*), and white potato cyst nematode (*Globodera pallida*);

from the family Hoplolaimidae, for example, *Rotylenchulus reniformis*;

from the family Anguinidae, for example, strawberry bud nematode (*Nothotylenchus acris*) and stem nematode (*Ditylenchus dipsaci*);

from the family Tylenchulidae, for example, citrus nematode (*Tylenchulus semipenetrans*);

from the family Longidoridae, for example, dagger nematode (*Xiphinema index*);

from the family Trichodoridae;

from the family Parasitaphelenchidae, for example, pine wilt disease (*Bursaphelenchus xylophilus*); and the others.

The target harmful arthropods such as harmful insects and harmful mites, harmful mollusks, and harmful nematodes may have a reduced agent-sensitivity to or a developed agent-resistance to an insecticide, a miticide, a molluscicide or a nematicide. However, when the agent-sensitivity is greatly reduced or the agent-resistance is greatly developed, a composition comprising an insecticide, a miticide, a molluscicide, and a nematicide other than the intended insecticide, miticide, molluscicide, and nematicide is preferably used.

The Present compounds X may be also used to protect plants from plant diseases caused by insect-borne viruses or insect-borne bacteria.

Examples of the insect-borne viruses are recited as follows.

Rice tungro spherical virus, Rice tungro bacilliform virus, Rice grassy stunt virus, Rice ragged stunt virus, Rice stripe virus, Rice black streaked dwarf virus, Southern rice black-streaked dwarf virus, Rice gall dwarf virus, Rice hoja blanca virus, Rice yellow stunt virus, Rice yellow mottle virus, Rice dwarf virus, Northern cereal mosaic virus, Barley yellow dwarf virus, Barley mild mosaic virus, Barley yellow dwarf virus-PAV, Cereal yellow dwarf virus-RPS, Wheat yellow leaf virus, Oat sterile dwarf virus, Wheat streak mosaic virus, Maize dwarf mosaic virus, Maize stripe virus, Maize chlorotic mottle virus, Maize chlorotic dwarf virus, Maize rayado fino virus, Sugarcane mosaic virus, Fiji disease virus, Sugarcane yellow leaf virus, Soybean mild mosaic virus, Cycas necrotic stunt virus, Soybean dwarf virus, Milk vetch dwarf virus, Soybean mosaic virus, Alfalfa mosaic virus, Bean yellow mosaic virus, Bean common mosaic virus, Southern bean mosaic virus, Peanut stunt virus, Broad bean wilt virus 1, Broad bean wilt virus 2, Broad bean necrosis virus, Broad bean yellow vein virus, Clover yellow vein virus, Peanut mottle virus, Tobacco streak virus, Bean pod mottle virus, Cowpea chlorotic mottle virus, Mung bean yellow mosaic virus, Soybean crinkle leaf virus, Tomato chlorosis virus, Tomato spotted wilt virus, Tomato yellow leaf curl virus, Tomato aspermy virus, Tomato infectious chlorosis virus, Potato leafroll virus, Potato virus Y, Melon yellow spot virus, Melon necrotic spot virus, Watermelon mosaic virus, Cucumber mosaic virus, Zucchini yellow mosaic virus, Turnip mosaic virus, Turnip yellow mosaic virus, Cauliflower mosaic virus, Lettuce mosaic virus, Celery mosaic virus, Beet mosaic virus, Cucurbit chlorotic yellows virus, Capsicum chlorosis virus, Beet pseudo yellows virus, Leak yellow stripe virus, Onion yellow dwarf virus, Sweet potato feathery mottle virus, Sweet potato shukuyo mosaic virus, Strawberry mottle virus, Strawberry mild yellow edge virus, Strawberry pseudo mild yellow edge virus, Strawberry crinkle virus, Strawberry vein banding virus, Plum pox virus, Chrysanthemum stem necrosis virus, Impatiens necrotic spot virus, Iris yellow spot virus, Lily mottle virus, Lilly symptomless virus, Tulip mosaic virus, and the others.

Examples of the insect-borne bacteria are recited as follows.

*Candidatus Phytoplasma oryzae, Candidatus Phytoplasma asteris, Maize bushy stunt phytoplasma, Candidatus Liberbacter asiaticus, Candidatus Liberbacter africanus, Candidatus Liberbacter americanus*, and the others.

The composition for controlling harmful arthropods of the present invention comprises the Present compound, the Present compound X, or the Composition A and inert carrier(s) (hereinafter referred to as "Present composition"). The Present composition is usually prepared by mixing the Present compound, the Present compound X, or the Composition A with inert carrier(s) such as solid carrier(s), liquid carrier(s), and gaseous carrier(s), and as needed, adding surfactant(s) and other auxiliary agent(s) for formulation, to formulate into an emulsifiable concentrate, an oil solution, a dust formulation, a granule, a wettable powder, a granular wettable powder, a flowable, a dry flowable, a microcapsule, an aerosol, a poison bait, a resin formulation, a shampoo formulation, a paste-like formulation, a foam, a carbon dioxide formulation, a tablet, or the like. Such formulation may be processed into and used as a mosquito repellent coil, an electric mosquito repellent mat, a liquid mosquito repellent formulation, a smoking agent, a fumigant, a sheet formulation, a spot-on formulation, or a formulation for oral treatment. The Present composition usually comprises 0.0001 to 95% by weight of the Present compound, the Present compound X, or the Composition A.

Examples of the solid carrier(s) to be used in the formulation include fine powders and granules of clays (for example, kaolin clay, diatomaceous earth, bentonite, Fubasami clay, and acid white clay), dry silica, wet silica, talc, ceramic, other inorganic minerals (for example, sericite, quartz, sulfur, active carbon, and calcium carbonate), chemical fertilizers (for example, ammonium sulfate, ammonium phosphate, ammonium nitrate, urea, and ammonium chloride), and the others; as well as synthetic resins (for example, polyester resins such as polypropylene, polyacrylonitrile, polymethylmethacrylate, and polyethylene terephthalate; nylon resins such as nylon-6, nylon-11, and nylon-66; polyamide resins; polyvinyl chloride, polyvinylidene chloride, vinyl chloride-propylene copolymers, and the others).

Examples of the liquid carrier(s) include water; alcohols (for example, methanol, ethanol, isopropyl alcohol, butanol, hexanol, benzyl alcohol, ethylene glycol, propylene glycol, and phenoxy ethanol); ketones (for example, acetone, methyl ethyl ketone, and cyclohexanone); aromatic hydrocarbons (for example, toluene, xylene, ethyl benzene, dodecyl benzene, phenyl xylyl ethane, and methylnaphthalene); aliphatic hydrocarbons (for example, hexane, cyclohexane, kerosene, and light oil); esters (for example, ethyl acetate, butyl acetate, isopropyl myristate, ethyl oleate, diisopropyl adipate, diisobutyl adipate, and propylene glycol monomethyl ether acetate); nitriles (for example, acetonitrile and isobutyronitrile); ethers (for example, diisopropyl ether, 1,4-dioxane, 1,2-dimethoxyethane, diethylene glycol dimethyl ether, diethylene glycol monomethyl ether, propylene glycol monomethyl ether, dipropylene glycol monomethyl ether, and 3-methoxy-3-methyl-1-butanol); amides (for example, DMF and N,N-dimethylacetamide); sulfoxides (for example, DMSO); propylene carbonate; and vegetable oils (for example, soybean oil and cottonseed oil).

Examples of the gaseous carrier(s) include fluorocarbon, butane gas, LPG (liquefied petroleum gas), dimethyl ether, and carbon dioxide.

Examples of the surfactant(s) include nonionic surfactants such as polyoxyethylene alkyl ethers, polyoxyethylene alkyl aryl ethers, and polyethylene glycol fatty acid esters; and anionic surfactants such as alkyl sulfonates, alkylbenzene sulfonates, and alkyl sulfates.

Examples of the other auxiliary agent(s) for formulation include binders, dispersants, colorants, and stabilizers. Specific examples thereof include casein, gelatin, saccharides (for example, starch, gum arabic, cellulose derivatives, and alginic acid), lignin derivatives, bentonite, water-soluble synthetic polymers (for example, polyvinyl alcohol, polyvinyl pyrrolidone, and polyacrylic acids), acidic isopropyl phosphate, 2,6-di-tert-butyl-4-methylphenol, and BHA (a mixture of 2-tert-butyl-4-methoxyphenol and 3-tert-butyl-4-methoxyphenol).

Examples of the base material of the resin formulation include vinyl chloride polymers, polyurethane, and the others, and plasticizer(s) such as phthalic acid esters (for example, dimethyl phthalate and dioctyl phthalate), adipic acid esters, and stearic acid may also be added to these base materials, as needed. The resin formulation may be prepared by mixing a compound with the above-mentioned base material, kneading the mixture in a conventional kneading apparatus, followed by molding it by injection molding, extrusion molding, pressure molding, or the like. The resultant resin formulation may be subjected to further molding, cutting procedure, or the like, as needed, to be processed into a shape such as plate, film, tape, net, and string shapes. These resin formulations may be processed into an animal collar, an animal ear tag, a sheet formulation, a trap string, a gardening support, or other products.

Examples of the base material for the poison bait include grain powders, vegetable oils, saccharides, crystalline celluloses, and the others, and further, antioxidant(s) such as dibutylhydroxytoluene and nordihydroguaiaretic acid, preservative(s) such as dehydroacetic acid, accidental ingestion inhibitor(s) for children and pets such as chili powder, insect attraction fragrance(s) such as cheese flavor, onion flavor, and peanut oil, or the other ingredient(s) may be added thereto as needed.

The method for controlling harmful arthropods of the present invention is carried out by applying an effective amount of the Present compound, the Present compound X, or the Composition A to harmful arthropods directly and/or habitats where harmful arthropods live (for example, plant bodies, soil, interiors of houses, and animal bodies). Also, the Present compound may be applied to seeds. Examples of the method for controlling harmful arthropods of the present invention include foliage treatment, soil treatment, root treatment, shower treatment, smoking treatment, water surface treatment, and seed treatment.

In the present invention, examples of the plants include whole plants, foliages, flowers, ears, fruits, tree stems, branches, tree crowns, seeds, vegetative reproduction organs, and seedlings.

A vegetative reproduction organ means a part of plant such as root, stem, and leaf which has a growth capability even when said part is separated from the plant body and placed into soil. Examples of the vegetative reproduction organ include tuberous root, creeping root, bulb, corm or solid bulb, tuber, rhizome, stolon, rhizophore, cane cuttings, propagule, and vine cutting. Stolon is also referred to as "runner", and propagule is also referred to as "propagulum" and categorized into broad bud and bulbil. Vine cutting means a shoot (collective term of leaf and stem) of sweet potato, glutinous yam, or the like. Bulb, corm or solid bulb, tuber, rhizome, cane cuttings, rhizophore, and tuberous root are also collectively referred to as "bulb". For example, cultivation of potato starts with planting a tuber into soil, and the tuber to be used is generally referred to as "seed potato".

Examples of the method for controlling harmful arthropods by applying an effective amount of the Present compound, the Present compound X, or the Composition A to soil include a method for applying an effective amount of the composition of the present invention to soil before or after planting plants, a method for applying an effective amount of the composition of the present invention to rhizosphere of crops to be protected from harm such as eating by harmful arthropods, and, a method for controlling plant-eating harmful arthropods by impregnating an effective amount of the composition of the present invention from roots or the like and migrating it to inside plant bodies. More specific examples thereof include planting hole treatments (for example, planting hole application and planting hole soil incorporation), plant foot treatments (for example, plant foot application, plant foot soil incorporation, plant foot irrigation, and plant foot treatment at latter half of raising of seedling period), planting trench treatments (for example, planting trench application and planting trench soil incorporation), row treatments (for example, row application, row soil incorporation, and row application at growing season), row treatments at seeding (for example, row application at seeding and row soil incorporation at seeding), overall treatments (for example, overall soil application and overall soil incorporation), side row treatments, water surface treatments (for example, water surface application and water surface application after flooding), other soil application treatments (for example, foliar application of granule at growing season, application under tree crown or around trunk, soil surface application, soil surface incorporation, seeding hole application, ridge area surface application, and intrarow spacing application), other irrigation treatments (for example, soil irrigation, irrigation at raising of seedling period, chemical injection treatment, ground area irrigation, chemical drip irrigation, and chemigation), raising seedling box treatments (for example, raising seedling box application, raising seedling box irrigation, raising seedling box chemical flooding), raising seedling tray treatments (for example, raising seedling tray application, raising seedling tray irrigation, and raising seedling tray chemical flooding), nursery treatments (for example, nursery application, nursery irrigation, flooded nursery application, and seedling soaking), bed soil incorporation treatments (for example, bed soil incorporation, bed soil incorporation before seeding, application at seeding before soil covering, application at seeding after soil covering, and soil covering incorporation), and other treatments (for example, culture soil incorporation, plowing, surface soil incorporation, rain dropping point soil incorporation, planting position treatment, flower cluster application of granule, and paste fertilizer incorporation).

When the Present composition is used for controlling harmful arthropods in the agricultural field, the application dose as an amount of the Present compound or the Present compound X is usually within the range from 1 to 10,000 g per 10,000 $m^2$. When the Present composition is applied to seeds or vegetative reproduction organs, the application dose as an amount of the Present compound or the Present compound X is usually within the range from 0.001 to 100 g per 1 Kg of the seeds or vegetative reproduction organs. An emulsifiable concentrate, a wettable powder, a flowable, or the like of the Present composition is usually applied by diluting it with water in such a way that a concentration of the active ingredient is within the range from 0.01 to 10,000 ppm. A granule, a dust formulation, or the like is usually applied as itself without diluting it.

These formulations and diluents of the formulations with water may be directly sprayed to harmful arthropods or plants such as crops to be protected from harmful arthropods, or applied to soil in cultivated areas to control harmful arthropods that inhabit the soil.

Also, a resin formulation processed into a sheet shape or a string shape may be wrapped around crops, stretched near crops, spread on plant foot soil, or the like.

When the Present composition is used to control harmful arthropods that live inside a house, the application dose as an amount of the Present compound or the Present compound X is usually within the range from 0.01 to 1,000 mg per 1 $m^2$ of an area to be treated in the case of using it on a planar area. In the case of using it spatially, the application dose as an amount of the Present compound or the Present compound X is usually within the range from 0.01 to 500 mg per 1 $m^3$ of the space to be treated. When the Present composition is formulated into an emulsifiable concentrate, a wettable powder, a flowable, or the like, such formulation is usually applied after diluting it with water in such a way that a concentration of the active ingredient is within the range from 0.1 to 10,000 ppm, and then sparging it. In the case of being formulated into an oil solution, an aerosol, a smoking agent, a poison bait, or the like, such formulation is used as itself without diluting it.

When the Present composition is used for controlling external parasites of livestock such as cows, horses, pigs, sheep, goats, and chickens, and small animals such as dogs, cats, rats, and mice, the Present composition may be applied to the animals by a known method in the veterinary field. Examples of the specific method for using the Present composition include administration by a tablet, a mixture with feed, a suppository, or an injection (for example, intramuscular, subcutaneous, intravenous, or intraperitoneal injection) when systemic control is intended, and include spraying of an oil solution or an aqueous liquid, pour-on treatment or spot-on treatment, washing of animals with a shampoo formulation, or application of a resin formulation in the form of a collar, an ear tag, or the like to animals when non-systemic control is intended. In case of administered to animals, the dose of the Present compound or the Present compound X is usually within the range from 0.1 to 1,000 mg per 1 kg of animal body weight.

Also, the Present compound, the Present compound X, or the Composition A may be used as an agent for controlling harmful arthropods in croplands such as fields, paddy fields, grasses, and orchards. Examples of the plants include the followings.

Crops: corn, rice, wheat, barley, rye, oat, sorghum, cotton, soybean, peanut, buckwheat, beet, rapeseed, sunflower, sugar cane, tobacco, and the others; Vegetables: solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, welsh onion, onion, garlic, and asparagus), ammiaceous vegetables (for example, carrot, parsley, celery, and parsnip), chenopodiaceous vegetables (for example, spinach and Swiss chard), lamiaceous vegetables (for example, perilla, mint, and basil), strawberry, sweet potato, glutinous yam, eddoe, and the others;

Flowers;

Foliage plants;

Fruits: pomaceous fruits (for example, apple, pear, Japanese pear, Chinese quince, and quince), stone fleshy fruits (for example, peach, plum, nectarine, Japanese apricot (*Prunus mume*), cherry fruit, apricot, and prune), citrus fruits (for example, Citrus unshiu, orange, lemon, lime, and grapefruit), nuts (for example, chestnuts, walnuts, hazelnuts, almond, pistachio, cashew nuts, and macadamia nuts), berry fruits (for example, blueberry, cranberry, blackberry, and raspberry), grapes, Japanese persimmon, olive, Japanese plum, banana, coffee, date palm, coconuts, and the others; and Trees other than fruit trees: tea, mulberry, flowering plants, roadside trees (for example, ash, birch, dogwood, eucalyptus, ginkgo (*Ginkgo biloba*), lilac, maple, oak (quercus), poplar, Judas tree, Formosan gum (*Liquidambar formosana*), plane tree, zelkova, Japanese arborvitae (*Thuja standishii*), fir wood, hemlock, juniper, pinus, picea, and yew (*Taxus cuspidate*)), and the others.

The above plants also include plants which may be produced by natural breeding, plants which may be generated by mutation, F1 hybrid plants, and genetically modified crops. Examples of the genetically modified crops include plants which have resistance to HPPD (4-hydroxyphenylpyruvate dioxygenase enzyme) inhibitors such as isoxaflutole, ALS (acetolactate synthase) inhibitors such as imazethapyr and thifensulfuron-methyl, EPSP (5-enolpyruvylshikimate-3-phosphate synthase) inhibitors, glutamine synthetase inhibitors, PPO (protoporphyrinogen oxidase) inhibitors, or herbicide such as bromoxynil and dicamba; plants which can synthesize a selective toxin known in *Bacillus* such as *Bacillus thuringiensis* or the like; and plants which can synthesize a gene fragment or the like which is partially identical to an endogenous gene derived from a harmful insect, and induce a gene silencing (RNAi; RNA interference) in the target harmful insect to achieve a specific insecticidal activity.

The above plants are not specifically limited as long as they are generally cultivated cultivars.

EXAMPLES

The following Examples including Preparation Examples, Formulation Examples, and Test Examples serve to illustrate the present invention more in detail, but the present invention is not limited to these Examples only.

First, Preparation Examples of the Present compounds X are shown below.

In the present description, Me represents a methyl group, Et represents an ethyl group, Pr represents a propyl group, i-Pr represents an isopropyl group, c-Pr represents a cyclopropyl group, Ph represents a phenyl group, Py2 represents a 2-pyridyl group, Py3 represents a 3-pyridyl group, Py4 represents a 4-pyridyl group, and Bn represents a benzyl group. When c-Pr, Ph, Py2, Py3, and Py4 have substituent(s), the substituent(s) is/are indicated before the symbols with the substitution position(s). For example, 1-CN-c-Pr represents a 1-cyanocyclopropyl group, 3,4-$F_2$-Ph represents a 3,4-difluorophenyl group, 4-$CF_3$—Py2 represents a 4-(trifluoromethyl)-2-pyridyl group, and 5-$OCH_2CF_2CF_3$-Py2 represents a 5-(2,2,3,3,3-pentafluoropropoxy)-2-pyridyl group.

Reference Preparation Example 1

A mixture of 4-amino-2-oxo-1,2-dihydropyrimidine (2.0 g), 1-bromo-3,3,3-trifluoro-2-propanone (1.9 mL), and methanol (20 mL) was added to a vial, the vial was covered, and the mixture was stirred in microwave at 120° C. for 3 hours. The resulting mixture was cooled to room temperature, water was added thereto, and the resulting mixture was extracted with ethyl acetate. The resulting organic layer was dried over anhydrous sodium sulfate, and concentrated under reduced pressure. The resulting residue was subjected to silica gel chromatography to give the Intermediate compound A-1 represented by the following formula (0.5 g).

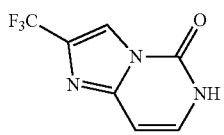 [SMILES: O=c1[nH]ccc2nc(C(F)(F)F)cn12]

Intermediate compound A-1: ¹H-NMR (DMSO-d$_6$) δ: 11.89 (1H, s), 8.38 (1H, s), 7.41 (1H, d), 6.64 (1H, d).

Reference Preparation Example 1A

The following Intermediate compound A-13 was prepared according to the Reference Preparation Example 1 by using 1-bromo-3,3,4,4,4-pentafluoro-2-butanone instead of 1-bromo-3,3,3-trifluoro-2-propanone.

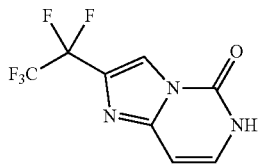 [SMILES: O=c1[nH]ccc2nc(C(F)(F)C(F)(F)F)cn12]

Intermediate compound A-13: ¹H-NMR (CDCl$_3$) δ: 9.19 (1H, s), 8.11 (1H, s), 7.16 (1H, dd), 6.76 (1H, d).

Reference Preparation Example 2-1

A mixture of 3-chloro-2-aminopyrazine (1.0 g) and 1-bromo-3,3,3-trifluoro-2-propanone (4.0 mL) in a closed container was stirred at 100° C. for 10.5 hours. The resulting mixture was cooled to room temperature, and filtered. The resulting solids were washed with hexane to give the Intermediate compound A-2 represented by the following formula (2.45 g).

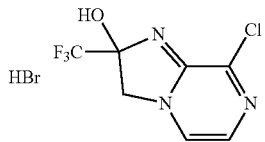 [SMILES: Br ; OC1(C(F)(F)F)CN2C=CN=C(Cl)C2=N1]

Intermediate compound A-2: ¹H-NMR (DMSO-d$_6$) δ: 8.36 (1H, s), 7.99 (1H, s), 5.05 (1H, d), 4.89 (1H, d).

Reference Preparation Example 2-2

A mixture of the Intermediate compound A-2 (2.16 g) and propionitrile (10 mL) was stirred under stirring for 2 hours. The resulting mixture was cooled to room temperature, 2N hydrochloric acid was added thereto until the mixture became weakly acidic, and the resulting mixture was extracted with ethyl acetate. The resulting organic layer was dried over anhydrous sodium sulfate, and concentrated under reduced pressure to give the Intermediate compound A-3 represented by the following formula (1.32 g).

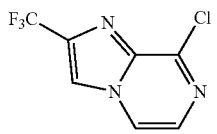 [SMILES: FC(F)(F)c1cn2ccnc(Cl)c2n1]

Intermediate compound A-3: ¹H-NMR (CDCl$_3$) δ: 8.10-8.09 (2H, m), 7.82 (1H, t).

Reference Preparation Example 2-3

A mixture of the Intermediate compound A-3 (1.32 g), concentrated hydrochloric acid (3 mL), and water (1 mL) was stirred at 100° C. for 4 hours. The resulting mixture was cooled to room temperature, the precipitated solids were collected by filtration, and washed sequentially with water and chloroform to give the Intermediate compound A-4 represented by the following formula (0.92 g).

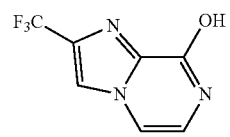

Intermediate compound A-4: ¹H-NMR (DMSO-d$_6$) δ: 11.45 (1H, s), 8.42 (1H, d), 7.50 (1H, d), 6.99 (1H, d).

Reference Preparation Example 13

Under nitrogen atmosphere, to a mixture of 2-(trifluoromethyl)pyrazolo[1,5-a]pyrazin-4(5H)-one (prepared according to the method described in WO 2006/023750 pamphlet) (0.20 g) and DMF (5 mL) was added N-chlorosuccinimide (0.15 g) at room temperature, and the resulting mixture was stirred at room temperature for 2.5 hours and then stirred at 80° C. for 1.5 hours. The resulting mixture was allowed to cool to room temperature, a saturated aqueous solution of sodium hydrogen carbonate was added thereto, and the resulting mixture was extracted with ethyl acetate. The resulting organic layer was dried over anhydrous magnesium sulfate, and then concentrated under reduced pressure. The resulting residue was subjected to silica gel column chromatography (hexane ethyl acetate=2:1) to give the Intermediate compound A-5 represented by the following formula (0.18 g).

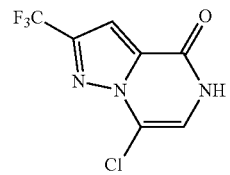

Intermediate compound A-5: ¹H-NMR (CDCl$_3$) δ: 9.81 (1H, br s), 7.46 (1H, s), 6.94 (1H, s).

Reference Preparation Example 13A

The following Intermediate compound A-6 was prepared according to the Reference Preparation Example 13.

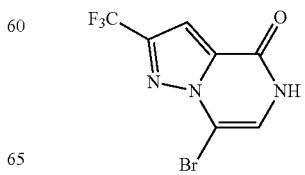

Intermediate compound A-6: ¹H-NMR (CDCl₃) δ: 10.15 (1H, br s), 7.49 (1H, s), 7.03 (1H, s).

Reference Preparation Example 14

Under nitrogen atmosphere, to a mixture of 3-trifluoromethyl-1H-pyrazole-5-carboxylic acid methyl ester (0.58 g) and DMF (10 mL) was added N-bromosuccinimide (0.59 g), and the resulting mixture was stirred at 60° C. for 1 day. To the resulting mixture were added a 1 M aqueous solution of sodium thiosulfate and a saturated aqueous solution of sodium hydrogen carbonate, and the resulting mixture was extracted with tert-butyl methyl ether. The resulting organic layer was dried over anhydrous magnesium sulfate, and then concentrated under reduced pressure. The resulting residue was subjected to silica gel column chromatography (hexane:ethyl acetate=2:1) to give the Intermediate compound A-7 represented by the following formula (0.53 g).

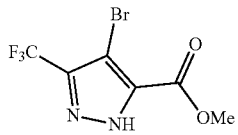 [SMILES: COC(=O)c1[nH]nc(C(F)(F)F)c1Cl]

Intermediate compound A-7: ¹H-NMR (CDCl₃) δ: 11.35 (1H, br s), 4.02 (3H, s).

Reference Preparation Example 14A

The following Intermediate compound A-8 was prepared according to the Reference Preparation Example 14.

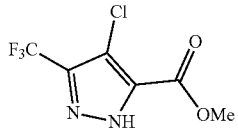

Intermediate compound A-8: ¹H-NMR (CDCl₃) δ: 11.46 (1H, br s), 4.02 (3H, s).

Reference Preparation Example 15

Under nitrogen atmosphere, to a mixture of 4-bromo-3-(trifluoromethyl)-1H-pyrazole-5-carboxylic acid methyl ester (0.53 g), THF (2 mL), water (2 mL), and methanol (2 mL) was added lithium hydroxide monohydrate (0.21 g) at room temperature, and the resulting mixture was stirred at room temperature for 1 hour. To the resulting mixture was added sodium hydroxide (0.21 g), and the resulting mixture was stirred at room temperature for 1 day. To the resulting mixture was added a saturated aqueous solution of sodium hydrogen carbonate, and the resulting mixture was extracted with ethyl acetate. To the resulting aqueous layer was added 1N hydrochloric acid, and the resulting mixture was extracted with ethyl acetate. The resulting organic layer was dried over anhydrous magnesium sulfate, and then concentrated under reduced pressure to give the Intermediate compound A-9 represented by the following formula (0.37 g).

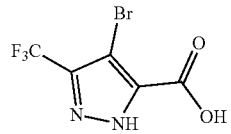

Intermediate compound A-9: ¹H-NMR (DMSO-D₆) δ: 8.28 (1H, s).

Reference Preparation Example 15A

The following Intermediate compound A-10 was prepared according to the Reference Preparation Example 15.

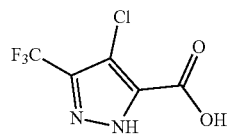

Intermediate compound A-10: ¹H-NMR (DMSO-D₆) δ: 7.21 (1H, S).

Reference Preparation Example 16

The following compound was synthesized according to the method described in WO 2006/023750 pamphlet.

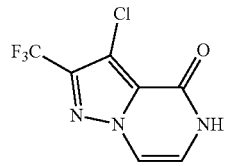 [SMILES: O=c1[nH]ccn2nc(C(F)(F)F)c(Cl)c12]

Intermediate compound A-11: ¹H-NMR (DMSO-D₆) δ: 10.98 (1H, s), 7.77 (1H, d), 7.10 (1H, d).

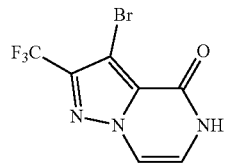 [SMILES: O=c1[nH]ccn2nc(C(F)(F)F)c(Br)c12]

Intermediate compound A-12: ¹H-NMR (DMSO-D₆) δ: 7.79 (1H, d), 7.10 (1H, d).

Reference Preparation Example 3

To a mixture of 2,2,6,6-tetramethylpiperidine (17.5 mL) and THF (150 mL) was added dropwise a 1.6 M solution of butyllithium in hexane (64.4 mL) at −78° C. To the resulting mixture was added dropwise 2-fluoropyridine (10 g) at −78° C., and then the resulting mixture was stirred for 30 minutes. Further, diethyl disulfide (12.7 mL) was added dropwise thereto at −78° C., and then the resulting mixture was stirred for 1 hour. To the resulting mixture was added a saturated aqueous solution of ammonium chloride under ice-cooling, the resulting mixture was warmed to room temperature, and then extracted with ethyl acetate. The resulting organic layer was washed with saturated brine, dried over anhydrous sodium sulfate, and concentrated under reduced pressure. The resulting residue was subjected to silica gel chromatography to give the Intermediate compound B-1 represented by the following formula (14.23 g).

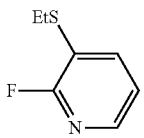

Intermediate compound B-1: $^1$H-NMR (CDCl$_3$) δ: 8.03 (1H, td), 7.74-7.69 (1H, m), 7.14 (1H, ddd), 2.97 (2H, q), 1.33 (3H, t).

Reference Preparation Example 4

To a mixture of sodium hydride (oily, 60%) (0.3 g), 2,3-dichloro-5-(trifluoromethyl)pyridine (0.5 mL), and DMF (5 mL) was added dropwise ethanethiol (0.54 mL) under ice-cooling, and then the resulting mixture was stirred at 40° C. for 12 hours. To the resulting mixture was added a saturated aqueous solution of ammonium chloride, and the resulting mixture was extracted with ethyl acetate. The resulting organic layer was dried over anhydrous sodium sulfate, and concentrated under reduced pressure. The resulting residue was subjected to silica gel chromatography to give the Intermediate compound B-3 represented by the following formula (0.61 g).

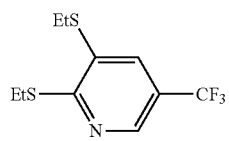

Intermediate compound B-3: $^1$H-NMR (CDCl$_3$) δ: 8.50 (1H, dd), 7.59 (1H, d), 3.24 (2H, q), 2.99 (2H, q), 1.39 (3H, t), 1.36 (3H, t).

Reference Preparation Example 5

The following Intermediate compound B-5 was prepared according to the Reference Preparation Example 4 by using 5-bromo-2-chloro-3-fluoropyridine.

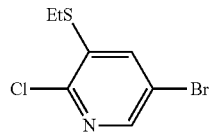

Intermediate compound B-5: $^1$H-NMR (CDCl$_3$) δ: 8.19 (1H, d), 7.57 (1H, d), 2.97 (2H, q), 1.42 (3H, t).

Reference Preparation Example 6

A mixture of the Intermediate compound B-5 (5.0 g), (trimethylsilyl)acetonitrile (5.4 mL), zinc fluoride (1.2 g), 4,5'-bis(diphenylphosphino)-9,9'-dimethylxanthene (1.14 g), tris(dibenzylideneacetone)dipalladium(0) (0.9 g), and DMF (10 mL) was stirred at 100° C. for 5 hours. The resulting mixture was cooled to room temperature, water was added thereto, and the resulting mixture was extracted with ethyl acetate. The resulting organic layer was washed with saturated brine, dried over anhydrous sodium sulfate, and concentrated under reduced pressure. The resulting residue was subjected to silica gel chromatography to give the Intermediate compound B-9 represented by the following formula (2.63 g).

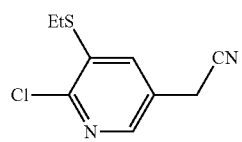

Intermediate compound B-9: $^1$H-NMR (CDCl$_3$) δ: 8.08 (1H, d), 7.49 (1H, d), 3.76 (2H, s), 3.00 (2H, q), 1.42 (3H, t).

Reference Preparation Example 7

A mixture of the Intermediate compound B-9 (3.27 g), 1,2-dibromoethane (1.6 mL), sodium hydride (oily, 60%) (1.29 g), and THF (30 mL) was stirred at room temperature for 3 hours. To the resulting mixture was added water, and the resulting mixture was extracted with ethyl acetate. The resulting organic layer was dried over anhydrous sodium sulfate, and concentrated under reduced pressure. The resulting residue was subjected to silica gel chromatography to give the Intermediate compound B-10 represented by the following formula (2.17 g).

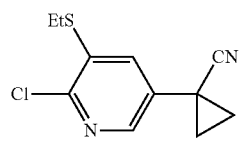

Intermediate compound B-10: $^1$H-NMR (CDCl$_3$) δ: 7.97 (1H, d), 7.51 (1H, d), 3.01 (2H, q), 1.83 (2H, m), 1.46 (2H, m), 1.42 (3H, t).

Reference Preparation Example 8

To a mixture of the Intermediate compound B-1 (8.9 g) and chloroform (100 mL) was added 70% mCPBA (28.0 g) under ice-cooling, and the resulting mixture was stirred at room temperature for 12 hours. To the resulting mixture were added a saturated aqueous solution of sodium hydrogen carbonate and a 1 M aqueous solution of sodium thiosulfate, and the resulting mixture was extracted with chloroform. The resulting organic layer was dried over anhydrous sodium sulfate, and concentrated under reduced pressure. The resulting residue was subjected to silica gel chromatography to give the Intermediate compound B-2 represented by the following formula (11.99 g).

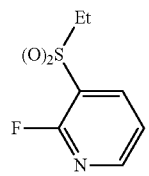

Intermediate compound B-2: $^1$H-NMR (CDCl$_3$) δ: 8.50 (1H, d), 8.43-8.38 (1H, m), 7.47-7.43 (1H, m), 3.38 (2H, q), 1.34 (3H, t).

Reference Preparation Example 9

The compounds prepared according to the Reference Preparation Example 8 and the physical properties thereof are shown below.

A compound represented by formula (B-1)

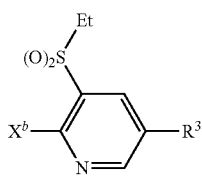

(B-1)

wherein the combination of $R^3$ and $X^b$ represents any one combination indicated in [Table B1].

TABLE B1

| Intermediate compound | $R^3$ | $X^b$ |
|---|---|---|
| B-4 | CF$^3$ | S(O)$_2$Et |
| B-6 | Br | Cl |
| B-11 | 1-CN-c-Pr | Cl |

Intermediate compound B-4: $^1$H-NMR (CDCl$_3$) δ: 9.17 (1H, s), 8.84 (1H, s), 3.81-3.79 (2H, m), 3.71-3.67 (2H, m), 1.46-1.43 (3H, m), 1.41-1.36 (3H, m).

Intermediate compound B-6: $^1$H-NMR (CDCl$_3$) δ: 8.69 (1H, d), 8.56 (1H, d), 3.51 (2H, q), 1.33 (3H, t).

Intermediate compound B-11: $^1$H-NMR (CDCl$_3$) δ: 8.71 (1H, d), 8.18 (1H, d), 3.51 (2H, q), 1.94-1.93 (2H, m), 1.55-1.53 (2H, m), 1.33 (3H, t).

Reference Preparation Example 10

A mixture of the Intermediate compound B-11 (1.09 g), cesium fluoride (1.2 g), and DMSO (10 mL) was stirred at 70° C. for 11 hours. To the resulting mixture was added water, and the resulting mixture was extracted with ethyl acetate. The resulting organic layer was dried over anhydrous sodium sulfate, and concentrated under reduced pressure. The resulting residue was subjected to silica gel chromatography to give the Intermediate compound B-12 represented by the following formula (0.85 g).

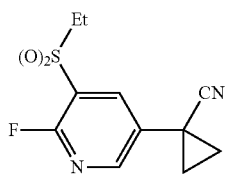

Intermediate compound B-12: $^1$H-NMR (CDCl$_3$) δ: 8.54 (1H, dd), 8.17 (1H, dd), 3.38 (2H, q), 1.92-1.90 (2H, m), 1.55-1.53 (2H, m), 1.35 (3H, t).

Reference Preparation Example 11

The Intermediate compound B-7 represented by the following formula was prepared according to the Reference Preparation Example 10.

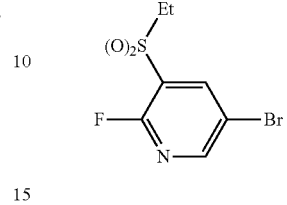

Intermediate compound B-7: $^1$H-NMR (CDCl$_3$) δ: 8.53 (1H, dd), 8.48 (1H, dd), 3.38 (2H, q), 1.36 (3H, t).

Reference Preparation Example 12

A mixture of the Intermediate compound B-7 (1.0 g), cyclopropylboronic acid (0.96 g), [1,1-bis(diphenylphosphino)ferrocene]palladium(II) dichloride (0.13 g), tripotassium phosphate (2.3 g), water (0.5 mL), and DME (5 mL) was stirred at 80° C. for 4 hours. The resulting mixture was cooled to room temperature, water was added thereto, and the resulting mixture was extracted with ethyl acetate. The resulting organic layer was washed with saturated brine, dried over anhydrous sodium sulfate, and concentrated under reduced pressure. The resulting residue was subjected to silica gel chromatography to give the Intermediate compound B-8 represented by the following formula (0.27 g).

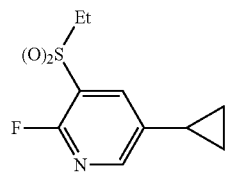

Intermediate compound B-8: $^1$H-NMR (CDCl$_3$) δ: 8.24 (1H, s), 7.95 (1H, dd), 3.35 (2H, q), 2.03-1.96 (1H, m), 1.33 (3H, t), 1.15-1.12 (2H, m), 0.80-0.77 (2H, m).

Reference Preparation Example 17

The Intermediate compounds which may be prepared according to the methods described in the Reference Preparation Examples 1 to 16 are shown below.

A compound represented by formula (C-7)

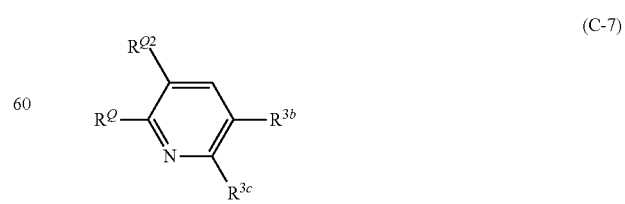

(C-7)

wherein the combination of $R^Q$, $R^{Q2}$, $R^{3b}$, and $R^{3c}$ represents any one combination indicated in (Table C7].

TABLE C7

| Intermediate compound | $R^Q$ | $R^{Q2}$ | $R^{3b}$ | $R^{3c}$ |
|---|---|---|---|---|
| B-13 | OH | SEt | c-Pr | H |
| B-14 | OH | S(O)Et | c-Pr | H |
| B-15 | OH | S(O)$_2$Et | c-Pr | H |
| B-16 | Cl | SEt | c-Pr | H |
| B-17 | Cl | S(O)Et | c-Pr | H |
| B-18 | Cl | S(O)$_2$Et | c-Pr | H |
| B-19 | SEt | SEt | Cl | H |
| B-20 | S(O)$_2$Et | S(O)$_2$Et | Cl | H |
| B-21 | Cl | SEt | Cl | H |
| B-22 | Cl | S(O)Et | Cl | H |
| B-23 | Cl | S(O)$_2$Et | Cl | H |
| B-24 | OH | SEt | Cl | H |
| B-25 | OH | S(O)Et | Cl | H |
| B-26 | OH | S(O)$_2$Et | Cl | H |
| B-27 | Cl | Cl | c-Pr | H |
| B-28 | F | F | c-Pr | H |
| B-29 | F | SEt | Cl | H |
| B-30 | F | S(O)Et | Cl | H |
| B-31 | F | S(O)$_2$Et | Cl | H |
| B-32 | F | SEt | c-Pr | H |
| B-33 | F | S(O)Et | c-Pr | H |
| B-34 | OH | S(O)$_2$Et | Br | H |

Intermediate compound B-16: $^1$H-NMR (CDCl$_3$) δ: 7.93 (1H, d), 7.17 (1H, d), 2.95 (2H, q), 1.91-1.84 (1H, in), 1.37 (3H, t), 1.06-1.04 (2H, in), 0.73-0.70 (2H, m).

Intermediate compound B-19: $^1$H-NMR (CDCl$_3$) δ: 8.22 (1H, d), 7.42 (1H, d), 3.18 (2H, q), 2.96 (2H, q), 1.37-1.35 (6H, m).

Intermediate compound B-20: $^1$H-NMR (CDCl$_3$) δ: 8.88 (1H, d), 8.60 (1H, d), 3.78 (2H, q), 3.64 (2H, q), 1.42 (3H, t), 1.37 (3H, t).

Intermediate compound B-23: $^1$H-NMR (CDCl$_3$) δ: 8.59 (1H, d), 8.42 (1H, d), 3.51 (2H, q), 1.34 (3H, t).

Intermediate compound B-26: $^1$H-NMR (CDCl$_3$) δ: 8.28 (1H, d), 7.87 (1H, d), 3.48 (2H, q), 1.32 (3H, t).

Intermediate compound B-28: $^1$H-NMR (CDCl$_3$) δ: 7.78 (1H, s), 7.19-7.14 (1H, m), 1.95-1.88 (1H, m), 1.07-1.04 (2H, m), 0.71-0.68 (2H, m).

Intermediate compound B-31: $^1$H-NMR (CDCl$_3$) δ: 8.43 (1H, dd), 8.35 (1H, m), 3.40 (2H, q), 1.36 (3H, t).

Reference Preparation Example 18

A mixture of the Present compound 9 (225 mg), bis(pinacolato)diboron (253 mg), [1,1'-bis(diphenylphosphino)ferrocene]dichloropalladium(II) (18 mg), potassium acetate (147 mg), and toluene (1.7 mL) was stirred at 80° C. for 1 hour. To the resulting mixture was added water under ice-cooling, and the resulting mixture was extracted with ethyl acetate. The resulting organic layer was dried over anhydrous sodium sulfate, and concentrated under reduced pressure to give the Intermediate compound D-1 as a crude product.

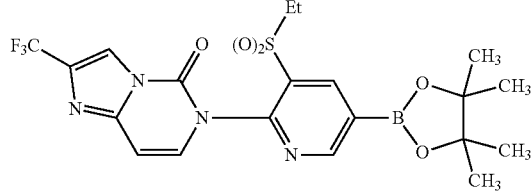

Intermediate compound D-1: $^1$H-NMR (CDCl$_3$) δ: 9.13 (1H, d), 8.79 (1H, d), 8.07 (1H, s), 7.23-7.16 (1H, d), 6.80 (1H, d), 3.43-3.40 (2H, m), 1.31-1.26 (15H, m).

Preparation Example 1

Under nitrogen atmosphere, to a mixture of the Intermediate compound A-1 (0.2 g), sodium hydride (oily, 60%) (0.05 g), and DMF (3 mL) was added the Intermediate compound B-2 (0.22 g) under ice-cooling, and the resulting mixture was stirred at 90° C. for 5 hours. The resulting mixture was cooled to room temperature, water was added thereto, and the resulting mixture was extracted with ethyl acetate. The resulting organic layer was dried over anhydrous sodium sulfate, and then concentrated under reduced pressure. The resulting residue was subjected to silica gel column chromatography (chloroform:methanol=10:1) to give the Present compound 4 represented by the following formula (0.2 g).

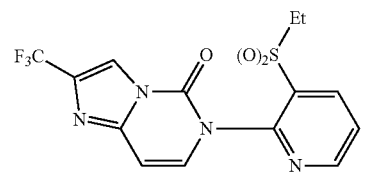

Present compound 4: $^1$H-NMR (CDCl$_3$) δ: 8.89 (1H, dd), 8.49 (1H, dd), 8.08 (1H, s), 7.77 (1H, dd), 7.23 (1H, d), 6.81 (1H, d), 3.40 (2H, q), 1.38 (3H, t).

Preparation Example 1A

The compounds prepared according to the Preparation Example 1 and the physical properties thereof are shown below.

A compound represented by formula (C-1)

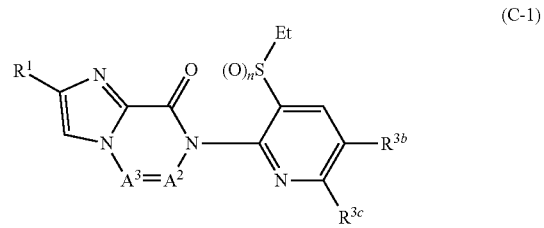

wherein the combination of R$^1$, A$^2$, A$^3$, R$^{3b}$, R$^{3c}$, and n represents any one combination indicated in [Table C1].

TABLE C1

| Present compound | $R^1$ | $A^2$ | $A^3$ | $R^{3b}$ | $R^{3c}$ | n |
|---|---|---|---|---|---|---|
| 1 | CF$_3$ | CH | CH | H | H | 2 |
| 2 | CF$_3$ | CH | CH | c-Pr | H | 2 |
| 3 | CF$_3$ | CH | CH | CF$_3$ | H | 2 |

Present compound 1: $^1$H-NMR (CDCl$_3$) δ: 8.87 (1H, dd), 8.48 (1H, dd), 7.78 (1H, s), 7.72 (1H, dd), 7.24 (1H, d), 6.93 (1H, d), 3.52-3.46 (2H, m), 1.36 (3H, t).

Present compound 2: $^1$H-NMR (CDCl$_3$) δ: 8.59 (1H, d), 8.01 (1H, d), 7.77 (1H, d), 7.23 (1H, d), 6.87 (1H, d), 3.43 (2H, q), 2.08-2.07 (1H, m), 1.34 (3H, t), 1.28-1.23 (2H, m), 0.94-0.88 (2H, m).

Present compound 3: $^1$H-NMR (CDCl$_3$) δ: 9.11 (1H, dd), 8.67 (1H, d), 7.82 (1H, s), 7.32 (1H, d), 6.96 (1H, d), 3.56 (2H, q), 1.40 (3H, t).

A compound represented by formula (C-2)

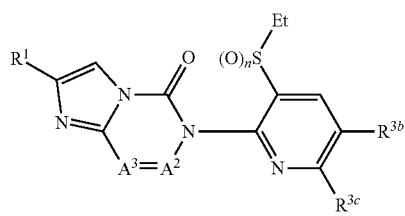

(C-2)

wherein the combination of R$^1$, A$^2$, A$^3$, R$^{3b}$, R$^{3c}$, and n represents any one combination indicated in [Table C2].

TABLE C2

| Present compound | R$^1$ | A$^2$ | A$^3$ | R$^{3b}$ | R$^{3c}$ | n |
|---|---|---|---|---|---|---|
| 5 | CF$_3$ | CH | CH | c-Pr | H | 2 |
| 6 | CF$_3$ | CH | CH | CF$_3$ | H | 2 |
| 9 | CF$_3$ | CH | CH | Br | H | 2 |
| 15 | C$_2$F$_5$ | CH | CH | H | H | 2 |
| 16 | C$_2$F$_5$ | CH | CH | Br | H | 2 |
| 17 | C$_2$F$_5$ | CH | CH | c-Pr | H | 2 |

Present compound 5: $^1$H-NMR (CDCl$_3$) δ: 8.60 (1H, d), 8.07 (1H, s), 8.02 (1H, d), 7.18 (1H, d), 6.78 (1H, d), 3.35 (2H, q), 2.14-2.07 (1H, m), 1.36 (3H, t), 1.30-1.26 (2H, m), 0.95-0.91 (2H, m).

Present compound 6: $^1$H-NMR (CDCl$_3$) δ: 9.13 (1H, d), 8.69 (1H, d), 8.09 (1H, s), 7.25 (1H, d), 6.85 (1H, d), 3.52-3.46 (2H, m), 1.43 (3H, t).

Present compound 9: $^1$H-NMR (CDCl$_3$) δ: 8.92 (1H, d), 8.58 (1H, d), 8.07 (1H, s), 7.19 (1H, d), 6.81 (1H, d), 3.42 (2H, m), 1.40 (3H, t).

Present compound 15: $^1$H-NMR (CDCl$_3$) δ: 8.89 (1H, dd), 8.50 (1H, dd), 8.12 (1H, s), 7.77 (1H, dd), 7.23 (1H, d), 6.83 (1H, d), 3.44-3.39 (2H, m), 1.39 (3H, t).

Present compound 16: $^1$H-NMR (CDCl$_3$) δ: 8.92 (1H, d), 8.58 (1H, d), 8.12 (1H, s), 7.22 (1H, d), 6.83 (1H, d), 3.43 (2H, q), 1.39 (3H, t).

Present compound 17: $^1$H-NMR (CDCl$_3$) δ: 8.60 (1H, d), 8.10 (1H, s), 8.02 (1H, d), 7.18 (1H, d), 6.80 (1H, d), 3.35 (2H, q), 2.13-2.08 (1H, m), 1.36 (3H, t), 1.31-1.24 (2H, m), 0.98-0.89 (2H, m).

A compound represented by formula (C-3)

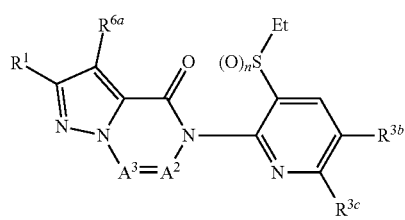

(C-3)

wherein the combination of R$^1$, R$^{6a}$, A$^2$, A$^3$, R$^{3b}$, R$^{3c}$, and n represents any one combination indicated in [Table C3].

TABLE C3

| Present compound | R$^1$ | R$^{6a}$ | A$^2$ | A$^3$ | R$^{3b}$ | R$^{3c}$ | n |
|---|---|---|---|---|---|---|---|
| 7 | CF$_3$ | H | CH | CH | H | H | 2 |
| 8 | CF$_3$ | H | CH | CH | c-Pr | H | 2 |
| 22 | CF$_3$ | H | CH | CBr | c-Pr | H | 2 |
| 23 | CF$_3$ | H | CH | CCl | c-Pr | H | 2 |
| 24 | CF$_3$ | Br | CH | CH | c-Pr | H | 2 |
| 25 | CF$_3$ | Cl | CH | CH | c-Pr | H | 2 |

Present compound 7: $^1$H-NMR (CDCl$_3$) δ: 8.89 (1H, dd), 8.49 (1H, dd), 7.73 (1H, dd), 7.60 (1H, dd), 7.39 (1H, s), 6.90 (1H, d), 3.41 (2H, m), 1.36 (3H, t).

Present compound 8: $^1$H-NMR (CDCl$_3$) δ: 8.61 (1H, d), 8.02 (1H, d), 7.58 (1H, d), 7.38 (1H, s), 6.85 (1H, d), 3.36 (2H, q), 2.10 (1H, m), 1.34 (3H, t), 1.26 (2H, m), 0.93 (2H, m).

Present compound 22: $^1$H-NMR (CDCl$_3$) δ: 8.60 (1H, d), 8.01 (1H, d), 7.52 (1H, s), 7.07 (1H, s), 3.37 (2H, q), 2.10 (1H, m), 1.35 (3H, t), 1.27 (2H, m), 0.92 (2H, m).

Present compound 23: $^1$H-NMR (CDCl$_3$) δ: 8.60 (1H, d), 8.01 (1H, d), 7.49 (1H, s), 7.00 (1H, s), 3.37 (2H, q), 2.09 (1H, m), 1.35 (3H, t), 1.27 (2H, m), 0.92 (2H, m).

Present compound 24: $^1$H-NMR (CDCl$_3$) δ: 8.60 (1H, d), 8.01 (1H, d), 7.51 (1H, d), 6.85 (1H, d), 3.39 (2H, m), 2.09 (1H, m), 1.36 (3H, t), 1.26 (2H, m), 0.92 (2H, m).

Present compound 25: $^1$H-NMR (CDCl$_3$) δ: 8.60 (1H, d), 8.01 (1H, d), 7.47 (1H, d), 6.83 (1H, d), 3.39 (2H, m), 2.09 (1H, m), 1.36 (3H, t), 1.26 (2H, m), 0.92 (2H, m).

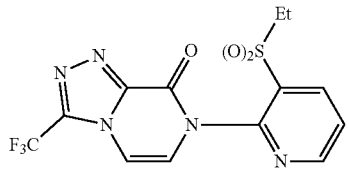

the Present compound 18: $^1$H-NMR (CDCl$_3$) δ: 8.90 (1H, dd), 8.50 (1H, dd), 7.77 (1H, dd), 7.33 (1H, d), 7.00 (1H, d), 3.47 (2H, q), 1.39 (3H, t).

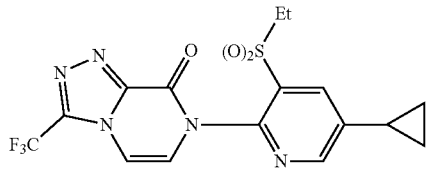

Present compound 19: $^1$H-NMR (CDCl$_3$) δ: 8.60 (1H, d), 8.02 (1H, d), 7.30 (1H, d), 6.94 (1H, d), 3.41 (2H, m), 2.10 (1H, m), 1.36 (3H, t), 1.27 (2H, m), 0.92 (2H, m).

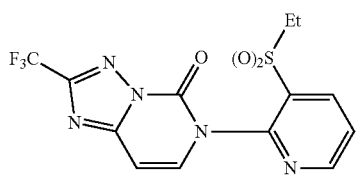

Present compound 20: $^1$H-NMR (CDCl$_3$) δ: 8.91 (1H, dd), 8.51 (1H, dd), 7.81 (1H, dd), 7.52 (1H, d), 6.93 (1H, d), 3.47 (2H, q), 1.39 (3H, t).

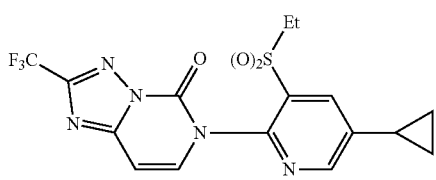

Present compound 21: ¹H-NMR (CDCl₃) δ: 8.61 (1H, d), 8.02 (1H, d), 7.46 (1H, d), 6.90 (1H, d), 3.42 (2H, m), 2.12 (1H, m), 1.37 (3H, t), 1.30 (2H, m), 0.94 (2H, m).

Preparation Example 2

A mixture of the Present compound 9 (0.3 g), 4-fluorophenylboronic acid (186 mg), [1,1-bis(diphenylphosphino)ferrocene]palladium(II) dichloride (51.3 mg), tripotassium phosphate (423 mg), water (0.3 mL), and DME (3.3 mL) was stirred at 80° C. for 2 hours. The resulting mixture was cooled to room temperature, water was added thereto, and the resulting mixture was extracted with ethyl acetate. The resulting organic layer was washed with saturated brine, dried over anhydrous sodium sulfate, and concentrated under reduced pressure. The resulting residue was subjected to silica gel chromatography (hexane:ethyl acetate=1:1) to give the Present compound 10 represented by the following formula (0.14 g).

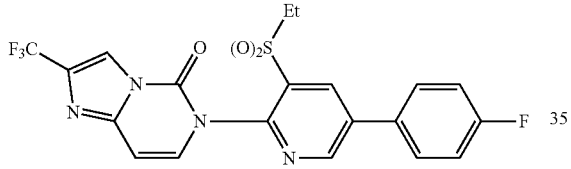

Present compound 10: ¹H-NMR (CDCl₃) δ: 9.02-9.00 (1H, m), 8.57-8.56 (1H, m), 8.10 (1H, s), 7.68-7.65 (2H, m), 7.30-7.24 (3H, m), 6.82 (1H, d), 3.43 (2H, q), 1.41 (3H, m).

Preparation Example 3

To the crude product of the Intermediate compound D-1 prepared in the Reference Preparation Example 18 were added water (1.6 mL), THF (0.4 mL), and sodium acetate (307 mg), and hydrogen peroxide (35% aqueous solution) was added dropwise thereto under ice-cooling. The resulting mixture was stirred under ice-cooling for 2 hours, a 1 M aqueous solution of sodium thiosulfate and a saturated aqueous solution of ammonium chloride were added thereto, and then the resulting mixture was extracted with ethyl acetate. The resulting organic layer was washed with a 1 M aqueous solution of sodium thiosulfate and saturated brine, dried over anhydrous sodium sulfate, and then concentrated under reduced pressure to give the Present compound 26.

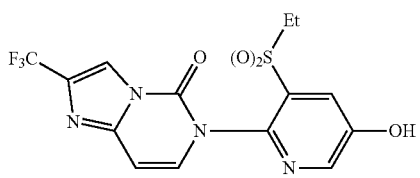

Present compound 26: ¹H-NMR (CDCl₃) δ: 8.45 (1H, br s), 8.08 (1H, s), 7.90 (1H, brs), 7.18 (1H, d), 6.77 (1H, d), 3.33 (2H, q), 1.35 (3H, t).

Preparation Example 4

To the Present compound 26 prepared in the Preparation Example 3 were added DMF (1.7 mL), cesium carbonate (244 mg), and iodoethane (0.06 mL), and the resulting mixture was stirred at room temperature for 1 hour. To the resulting mixture were added water and a saturated aqueous solution of ammonium chloride, and the resulting mixture was extracted with ethyl acetate. The resulting organic layer was dried over anhydrous sodium sulfate, and concentrated under reduced pressure. The resulting residue was subjected to silica gel chromatography (hexane:ethyl acetate=1:3) to give the Present compound 11 represented by the following formula (0.1 g).

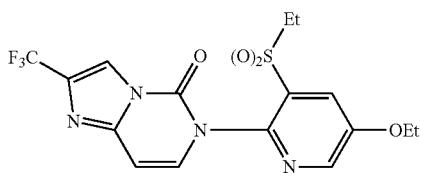

Present compound 11: ¹H-NMR (CDCl₃) δ: 8.47 (1H, d), 8.07 (1H, s), 7.87 (1H, d), 7.16 (1H, d), 6.77 (1H, d), 4.28-4.22 (2H, m), 3.34 (2H, q), 1.53 (3H, t), 1.36 (3H, t).

Preparation Example 4A

The compounds prepared according to the Preparation Example 4 and the physical properties thereof are shown below.

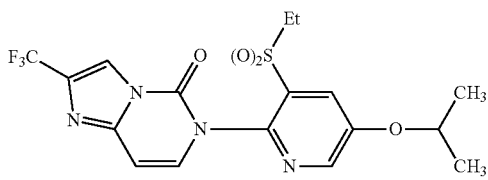

Present compound 12: ¹H-NMR (CDCl₃) δ: 8.43 (1H, d), 8.07 (1H, s), 7.85 (1H, d), 7.16 (1H, d), 6.77 (1H, d), 4.78-4.72 (1H, m), 3.34 (2H, q), 1.46 (6H, m), 1.37 (3H, t).

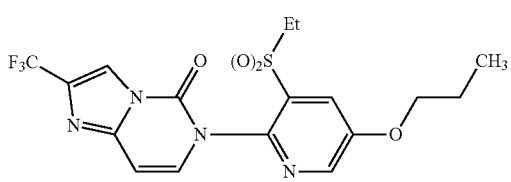

Present compound 13: ¹H-NMR (CDCl₃) δ: 8.48 (1H, d), 8.07 (1H, s), 7.88 (1H, d), 7.16 (1H, d), 6.77 (1H, dd), 4.13 (2H, q), 3.37-3.32 (2H, m), 1.92 (2H, m), 1.37 (3H, t), 1.10 (3H, t).

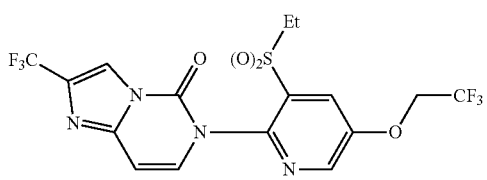

Present compound 14: ¹H-NMR (CDCl₃) δ: 8.59 (1H, d), 8.07 (1H, s), 7.98 (1H, d), 7.16 (1H, dd), 6.79 (1H, d), 4.59 (2H, q), 3.38 (2H, m), 1.38 (3H, t).

Preparation Example 5

The compounds which can be prepared according to the methods described in the Preparation Examples 1 to 4 are shown below.

A compound represented by formula (C-4)

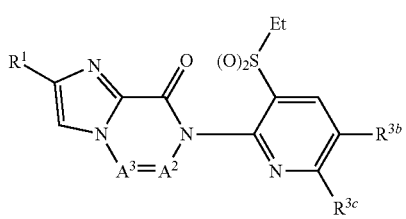

(C-4)

wherein the combination of $R^1$, $A^2$, $A^3$, $R^{3b}$, $R^{3c}$, and n represents any one combination indicated in [Table C4].

TABLE C4

| Present compound | $R^1$ | $A^2$ | $A^3$ | $R^{3b}$ | $R^{3c}$ | n |
|---|---|---|---|---|---|---|
| 27 | C₂F₅ | CH | CH | H | H | 2 |
| 28 | C₂F₅ | CH | CH | c-Pr | H | 2 |
| 29 | C₂F₅ | CH | CH | CF₃ | H | 2 |
| 30 | CF₃ | CH | N | H | H | 2 |
| 31 | CF₃ | CH | N | c-Pr | H | 2 |
| 32 | CF₃ | CH | N | CF₃ | H | 2 |

A compound represented by formula (C-5)

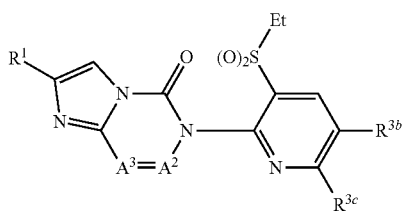

(C-5)

wherein the combination of $R^1$, $A^2$, $A^3$, $R^{3b}$, $R^{3C}$, and n represents any one combination indicated in [Table C5].

TABLE C5

| Present compound | $R^1$ | $A^2$ | $A^3$ | $R^{3b}$ | $R^{3c}$ | n |
|---|---|---|---|---|---|---|
| 33 | CF₃ | CH | N | c-Pr | H | 2 |
| 34 | C₂F₅ | CH | CH | CF₃ | H | 2 |
| 35 | CF₃ | CH | N | CF₃ | H | 2 |
| 36 | CF₃ | CH | N | Br | H | 2 |

TABLE C5-continued

| Present compound | $R^1$ | $A^2$ | $A^3$ | $R^{3b}$ | $R^{3c}$ | n |
|---|---|---|---|---|---|---|
| 37 | C₂F₅ | CH | N | H | H | 2 |
| 38 | C₂F₅ | CH | N | Br | H | 2 |
| 39 | C₂F₅ | CH | N | c-Pr | H | 2 |

A compound represented by formula (C-6)

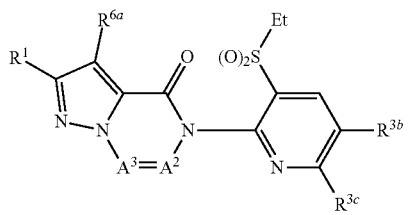

(C-6)

wherein the combination of $R^1$, $R^{6a}$, $A^2$, $A^3$, $R^{3b}$, $R^{3c}$, and n represents any one combination indicated in [Table C6].

TABLE C6

| Present compound | $R^1$ | $R^{6a}$ | $A^2$ | $A^3$ | $R^{3b}$ | $R^{3c}$ | n |
|---|---|---|---|---|---|---|---|
| 40 | CF₃ | H | CH | N | H | H | 2 |
| 41 | CF₃ | H | CH | N | c-Pr | H | 2 |
| 42 | C₂F₅ | H | CH | CH | H | H | 2 |
| 43 | C₂F₅ | H | CH | CH | c-Pr | H | 2 |
| 44 | CF₃ | Br | CH | N | c-Pr | H | 2 |
| 45 | CF₃ | Cl | CH | N | c-Pr | H | 2 |
| 46 | C₂F₅ | Br | CH | CH | c-Pr | H | 2 |
| 47 | C₂F₅ | Cl | CH | CH | c-Pr | H | 2 |

Next, examples of the Present compounds prepared according to any one of the Preparation Examples described in Examples and the processes described in the present description are shown below. In the following examples, Q11 to Q21 represent the following groups.

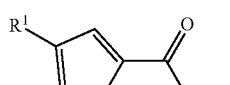

Q11

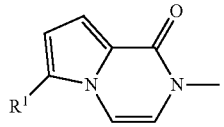

Q12

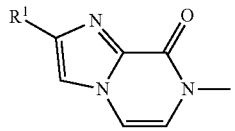

Q13

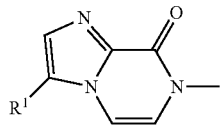

Q14

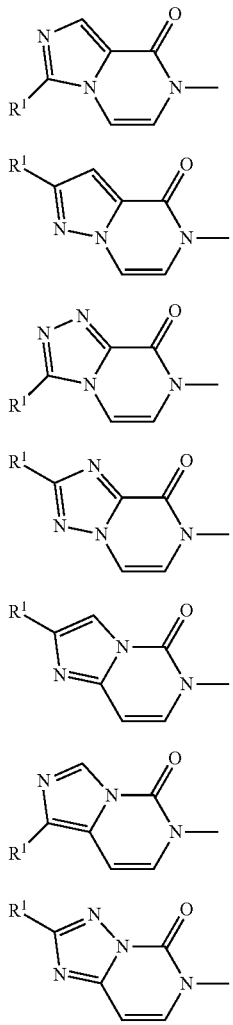

A compound represented by formula (L-1)

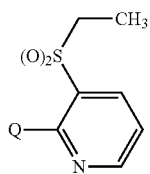

(hereinafter referred to as "Compound (L-1)"), wherein Q represents a group represented by Q11, and $R^1$ represents any one substituent described in [Table A1] or [Table A2](hereinafter referred to as "Compound group SX1").

TABLE A1

| |
| --- |
| $CF_3$ |
| $CHF_2$ |
| $CH_2CF_3$ |
| $CF_2CF_3$ |
| $CH_2CF_2CF_3$ |
| $CF_2CF_2CF_3$ |
| $CF_2CF_2CF_2CF_3$ |

TABLE A1-continued

| |
| --- |
| $CF_2CF_2CF_2CF_2CF_3$ |
| $C(CF_3)_3$ |
| $C(CH_3)_2CN$ |
| $OCF_3$ |
| $OCHF_2$ |
| $OCH_2CF_3$ |
| $OCH_2CHF_2$ |
| $OCF_2CF_3$ |
| $OCH(CH_3)CF_3$ |
| $OCH_2CF_2CHF_2$ |
| $OCH_2CF_2CF_3$ |
| $OCF_2CF_2CF_3$ |
| $OCH_2CF_2CHFCF_3$ |
| $OCH_2CF_2CF_2CF_3$ |
| $OCF_2CF_2CF_2CF_3$ |
| $OCH_2CF_2CF_2CF_2CF_3$ |
| $OS(O)_2CF_3$ |
| $OS(O)_2CF_2CF_3$ |
| $OS(O)_2CF_2CF_2CF_3$ |
| $SCF_3$ |
| $SCH_2CF_3$ |
| $SCF_2CF_3$ |
| $SCH_2CF_2CF_3$ |
| $SCF_2CF_2CF_3$ |
| $SCH_2CF_2CF_2CF_3$ |
| $SCF_2CF_2CF_2CF_3$ |
| $S(O)CF_3$ |
| $S(O)CH_2CF_3$ |
| $S(O)CF_2CF_3$ |
| $S(O)CH_2CF_2CF_3$ |
| $S(O)CF_2CF_2CF_3$ |
| $S(O)CH_2CF_2CF_2CF_3$ |
| $S(O)CF_2CF_2CF_2CF_3$ |
| $S(O)_2CF_3$ |
| $S(O)_2CH_2CF_3$ |
| $S(O)_2CF_2CF_3$ |
| $S(O)_2CH_2CF_2CF_3$ |
| $S(O)_2CF_2CF_2CF_3$ |
| $S(O)_2CH_2CF_2CF_2CF_3$ |
| $S(O)_2CF_2CF_2CF_2CF_3$ |
| c-Pr |
| 1-CN-c-Pr |
| 2-CN-c-Pr |
| 1-CN-c-Bu |
| $CF(CF_3)_2$ |

The Compound (L-1), wherein Q represents a group represented by Q12, and $R^1$ represents any one substituent described in [Table A1] or [Table A2] (hereinafter referred to as "Compound group SX2").

The Compound (L-1), wherein Q represents a group represented by Q13, and $R^1$ represents any one substituent described in [Table A1] or [Table A2] (hereinafter referred to as "Compound group SX3").

The Compound (L-1), wherein Q represents a group represented by Q14, and $R^1$ represents any one substituent described in [Table A1] or [Table A2] (hereinafter referred to as "Compound group SX4").

The Compound (L-1), wherein Q represents a group represented by Q15, and $R^1$ represents any one substituent described in [Table A1] or [Table A2] (hereinafter referred to as "Compound group SX5").

The Compound (L-1), wherein Q represents a group represented by Q16, and $R^1$ represents any one substituent described in [Table A1] or [Table A2] (hereinafter referred to as "Compound group SX6").

The Compound (L-1), wherein Q represents a group represented by Q17, and $R^1$ represents any one substituent described in [Table A1] or [Table A2] (hereinafter referred to as "Compound group SX7").

The Compound (L-1), wherein Q represents a group represented by Q18, and R¹ represents any one substituent described in [Table A1] or [Table A2] (hereinafter referred to as "Compound group SX8").

The Compound (L-1), wherein Q represents a group represented by Q19, and R¹ represents any one substituent described in [Table A1] or [Table A2] (hereinafter referred to as "Compound group SX9").

The Compound (L-1), wherein Q represents a group represented by Q20, and R¹ represents any one substituent described in [Table A1] or [Table A2] (hereinafter referred to as "Compound group SX10").

The Compound (L-1), wherein Q represents a group represented by Q21, and R¹ represents any one substituent described in [Table A1] or [Table A2] (hereinafter referred to as "Compound group SX11").

In the following examples, Q31 to Q52 represent the following groups.

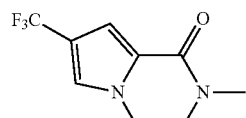

Q31

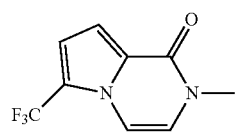

Q32

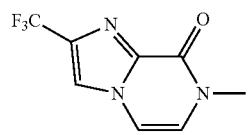

Q33

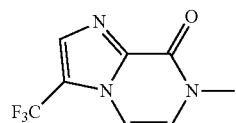

Q34

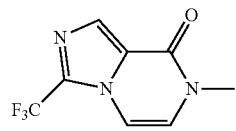

Q35

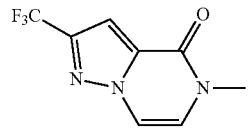

Q36

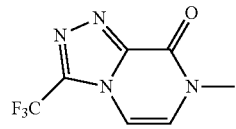

Q37

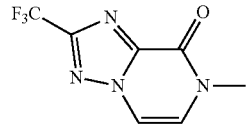

Q38

-continued

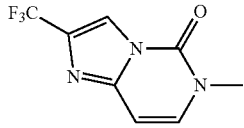

Q39

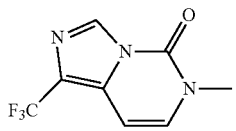

Q40

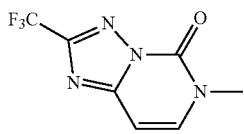

Q41

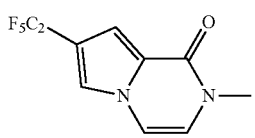

Q42

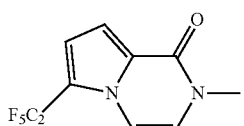

Q43

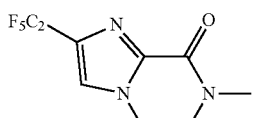

Q44

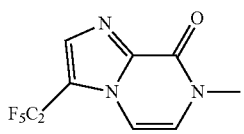

Q45

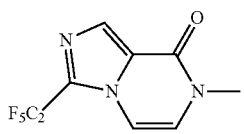

Q46

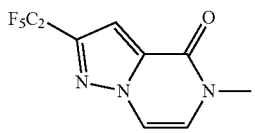

Q47

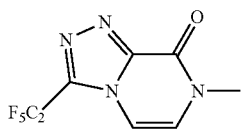

Q48

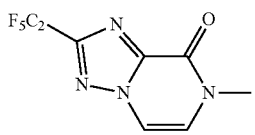

Q49

-continued

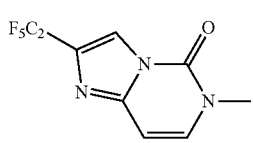

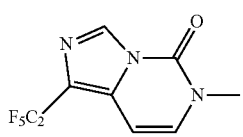

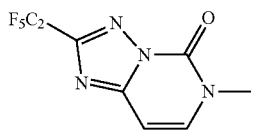

A compound represented by formula (L-2)

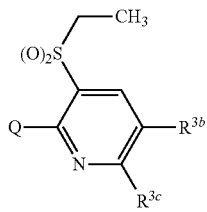

(L-2)

(hereinafter referred to as "Compound (L-2)"), wherein Q represents a group represented by Q31, $R^{3b}$ represents any one substituent described in [Table A3] to [Table A11], and $R^{3c}$ represents a hydrogen atom (hereinafter referred to as "Compound group SX12").

TABLE A3

F
Cl
Br
Me
Et
Pr
i-Pr
c-Pr
1-CN-c-Pr
OMe
OEt
OPr
Oi-Pr
$CF_3$
$NH_2$
$NHCH_2CF_3$
CN
C(O)OEt
NHC(O)c-Pr
NMeC(O)c-Pr
CH=N—OH
CH=N—OMe

TABLE A4

Ph
3-F—Ph
4-F—Ph
3-Cl—Ph
4-Cl—Ph

Q50

Q51

Q52

TABLE A4-continued

3-$CF_3$—Ph
4-$CF_3$-P—h
3-$NMe_2$—Ph
4-$NMe_2$—Ph
3-CN—Ph
4-CN—Ph
4-C(O)$NMe_2$—Ph
4-NHC(O)Me—Ph
3,4-$F_2$—Ph
3,5-$F_2$—Ph
2,4-$F_2$—Ph
3,4,5-$F_3$—Ph
3,4-$Cl_2$—Ph
3,5-$Cl_2$—Ph
3,5-$Cl_2$-4-F—Ph
OPh
O-2-F—Ph

TABLE A5

Py2
4-F—Py2
5-F—Py2
4-Cl—Py2
5-Cl—Py2
4-$CF_3$—Py2
5-$CF_3$—Py2
3-Me—Py2
4-Me—Py2
5-Me—Py2
6-Me—Py2
5-CN—Py2
5-$OCH_2CF_2CF_3$—Py2
3,5-$F_2$—Py2
Py3
6-$CF_3$—Py3
5-$CF_3$—Py3
6-F—Py3
6-Cl—Py3
Py4
OPy2
OPy3

TABLE A6

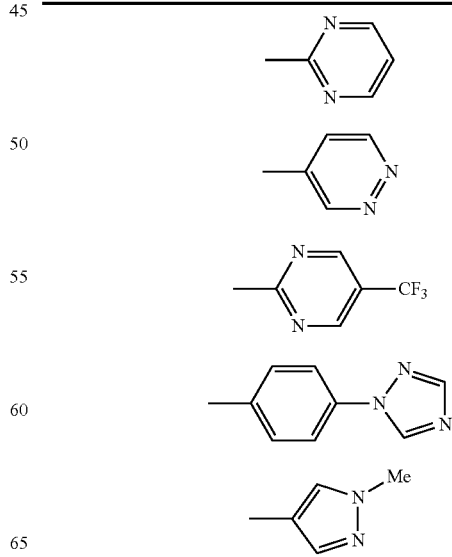

TABLE A6-continued

TABLE A7

TABLE A8

TABLE A8-continued

TABLE A9

TABLE A10

TABLE A10-continued

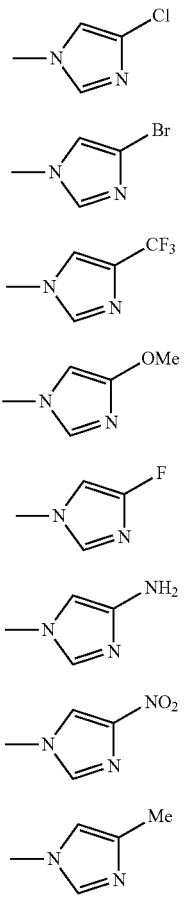

TABLE A11

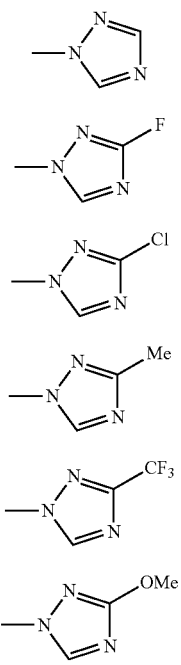

TABLE A11-continued

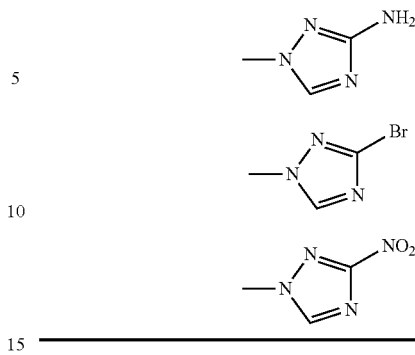

The Compound (L-2), wherein Q represents a group represented by Q31, $R^{3b}$ represents a hydrogen atom, and $R^{3c}$ represents any one substituent described in [Table A3] to [Table A11] (hereinafter referred to as "Compound group SX13").

The Compound (L-2), wherein Q represents a group represented by Q32, $R^{3b}$ represents any one substituent described in [Table A3] to [Table A11], and $R^{3c}$ represents a hydrogen atom (hereinafter referred to as "Compound group SX14").

The Compound (L-2), wherein Q represents a group represented by Q32, $R^{3b}$ represents a hydrogen atom, and $R^{3'}$ represents any one substituent described in [Table A3] to [Table A11] (hereinafter referred to as "Compound group SX15").

The Compound (L-2), wherein Q represents a group represented by Q33, $R^{3b}$ represents any one substituent described in [Table A3] to [Table A11], and $R^{3C}$ represents a hydrogen atom (hereinafter referred to as "Compound group SX16").

The Compound (L-2), wherein Q represents a group represented by Q33, $R^{3b}$ represents a hydrogen atom, and $R^{3c}$ represents any one substituent described in [Table A3] to [Table A11] (hereinafter referred to as "Compound group SX17").

The Compound (L-2), wherein Q represents a group represented by Q34, $R^{3b}$ represents any one substituent described in [Table A3] to [Table A11], and $R^{3c}$ represents a hydrogen atom (hereinafter referred to as "Compound group SX18").

The Compound (L-2), wherein Q represents a group represented by Q34, $R^{3b}$ represents a hydrogen atom, and $R^{3c}$ represents any one substituent described in [Table A3] to [Table A11] (hereinafter referred to as "Compound group SX19").

The Compound (L-2), wherein Q represents a group represented by Q35, $R^{3b}$ represents any one substituent described in [Table A3] to [Table A11], and $R^{3c}$ represents a hydrogen atom (hereinafter referred to as "Compound group SX20").

The Compound (L-2), wherein Q represents a group represented by Q35, $R^{3b}$ represents a hydrogen atom, and $R^{3c}$ represents any one substituent described in [Table A3] to [Table A11] (hereinafter referred to as "Compound group SX21").

The Compound (L-2), wherein Q represents a group represented by Q36, $R^{3b}$ represents any one substituent described in [Table A3] to [Table A11], and $R^{3c}$ represents a hydrogen atom (hereinafter referred to as "Compound group SX22").

The Compound (L-2), wherein Q represents a group represented by Q36, $R^{3b}$ represents a hydrogen atom, and $R^{3c}$ represents any one substituent described in [Table A3] to [Table A11] (hereinafter referred to as "Compound group SX23").

The Compound (L-2), wherein Q represents a group represented by Q37, $R^{3b}$ represents any one substituent described in [Table A3] to [Table A11], and $R^{3c}$ represents a hydrogen atom (hereinafter referred to as "Compound group SX24").

The Compound (L-2), wherein Q represents a group represented by Q37, $R^{3b}$ represents a hydrogen atom, and $R^{3c}$ represents any one substituent described in [Table A3] to [Table A11] (hereinafter referred to as "Compound group SX25").

The Compound (L-2), wherein Q represents a group represented by Q38, $R^{3b}$ represents any one substituent described in [Table A3] to [Table A11], and $R^{3c}$ represents a hydrogen atom (hereinafter referred to as "Compound group SX26").

The Compound (L-2), wherein Q represents a group represented by Q38, $R^{3b}$ represents a hydrogen atom, and $R^{3c}$ represents any one substituent described in [Table A3] to [Table A11] (hereinafter referred to as "Compound group SX27").

The Compound (L-2), wherein Q represents a group represented by Q39, $R^{3b}$ represents any one substituent described in [Table A3] to [Table A11], and $R^{3c}$ represents a hydrogen atom (hereinafter referred to as "Compound group SX28").

The Compound (L-2), wherein Q represents a group represented by Q39, $R^{3b}$ represents a hydrogen atom, and $R^{3c}$ represents any one substituent described in [Table A3] to [Table A11] (hereinafter referred to as "Compound group SX29").

The Compound (L-2), wherein Q represents a group represented by Q40, $R^{3b}$ represents any one substituent described in [Table A3] to [Table A11], and $R^{3c}$ represents a hydrogen atom (hereinafter referred to as "Compound group SX30").

The Compound (L-2), wherein Q represents a group represented by Q40, $R^{3b}$ represents a hydrogen atom, and $R^{3c}$ represents any one substituent described in [Table A3] to [Table A11] (hereinafter referred to as "Compound group SX31").

The Compound (L-2), wherein Q represents a group represented by Q41, $R^{3b}$ represents any one substituent described in [Table A3] to [Table A11], and $R^{3c}$ represents a hydrogen atom (hereinafter referred to as "Compound group SX32").

The Compound (L-2), wherein Q represents a group represented by Q41, $R^{3b}$ represents a hydrogen atom, and $R^{3c}$ represents any one substituent described in [Table A3] to [Table A11] (hereinafter referred to as "Compound group SX33").

The Compound (L-2), wherein Q represents a group represented by Q42, $R^{3b}$ represents any one substituent described in [Table A3] to [Table A11], and $R^{3c}$ represents a hydrogen atom (hereinafter referred to as "Compound group SX34").

The Compound (L-2), wherein Q represents a group represented by Q42, $R^{3b}$ represents a hydrogen atom, and $R^{3c}$ represents any one substituent described in [Table A3] to [Table A11] (hereinafter referred to as "Compound group SX35").

The Compound (L-2), wherein Q represents a group represented by Q43, $R^{3b}$ represents any one substituent described in [Table A3] to [Table A11], and $R^{3c}$ represents a hydrogen atom (hereinafter referred to as "Compound group SX36").

The Compound (L-2), wherein Q represents a group represented by Q43, $R^{3b}$ represents a hydrogen atom, and $R^{3c}$ represents any one substituent described in [Table A3] to [Table A11] (hereinafter referred to as "Compound group SX37").

The Compound (L-2), wherein Q represents a group represented by Q44, $R^{3b}$ represents any one substituent described in [Table A3] to [Table A11], and $R^{3c}$ represents a hydrogen atom (hereinafter referred to as "Compound group SX38").

The Compound (L-2), wherein Q represents a group represented by Q44, $R^{3b}$ represents a hydrogen atom, and $R^{3c}$ represents any one substituent described in [Table A3] to [Table A11] (hereinafter referred to as "Compound group SX39").

The Compound (L-2), wherein Q represents a group represented by Q45, $R^{3b}$ represents any one substituent described in [Table A3] to [Table A11], and $R^{3c}$ represents a hydrogen atom (hereinafter referred to as "Compound group SX40").

The Compound (L-2), wherein Q represents a group represented by Q45, $R^{3b}$ represents a hydrogen atom, and $R^{3c}$ represents any one substituent described in [Table A3] to [Table A11] (hereinafter referred to as "Compound group SX41").

The Compound (L-2), wherein Q represents a group represented by Q46, $R^{3b}$ represents any one substituent described in [Table A3] to [Table A11], and $R^{3c}$ represents a hydrogen atom (hereinafter referred to as "Compound group SX42").

The Compound (L-2), wherein Q represents a group represented by Q46, $R^{3b}$ represents a hydrogen atom, and $R^{3c}$ represents any one substituent described in [Table A3] to [Table A11] (hereinafter referred to as "Compound group SX43").

The Compound (L-2), wherein Q represents a group represented by Q47, $R^{3b}$ represents any one substituent described in [Table A3] to [Table A11], and $R^{3c}$ represents a hydrogen atom (hereinafter referred to as "Compound group SX44").

The Compound (L-2), wherein Q represents a group represented by Q47, $R^{3b}$ represents a hydrogen atom, and $R^{3c}$ represents any one substituent described in [Table A3] to [Table A11] (hereinafter referred to as "Compound group SX45").

The Compound (L-2), wherein Q represents a group represented by Q48, $R^{3b}$ represents any one substituent described in [Table A3] to [Table A11], and $R^{3c}$ represents a hydrogen atom (hereinafter referred to as "Compound group SX46").

The Compound (L-2), wherein Q represents a group represented by Q48, $R^{3b}$ represents a hydrogen atom, and $R^{3c}$ represents any one substituent described in [Table A3] to [Table A11] (hereinafter referred to as "Compound group SX47").

The Compound (L-2), wherein Q represents a group represented by Q49, $R^{3b}$ represents any one substituent described in [Table A3] to [Table A11], and $R^{3c}$ represents a hydrogen atom (hereinafter referred to as "Compound group SX48").

The Compound (L-2), wherein Q represents a group represented by Q49, $R^{3b}$ represents a hydrogen atom, and $R^{3c}$ represents any one substituent described in [Table A3] to [Table A11] (hereinafter referred to as "Compound group SX49").

The Compound (L-2), wherein Q represents a group represented by Q50, $R^{3b}$ represents any one substituent described in [Table A3] to [Table A11], and $R^{3c}$ represents a hydrogen atom (hereinafter referred to as "Compound group SX50").

The Compound (L-2), wherein Q represents a group represented by Q50, $R^{3b}$ represents a hydrogen atom, and $R^{3c}$ represents any one substituent described in [Table A3] to [Table A11] (hereinafter referred to as "Compound group SX51").

The Compound (L-2), wherein Q represents a group represented by Q51, $R^{3b}$ represents any one substituent described in [Table A3] to [Table A11], and $R^{3c}$ represents a hydrogen atom (hereinafter referred to as "Compound group SX52").

The Compound (L-2), wherein Q represents a group represented by Q51, $R^{3b}$ represents a hydrogen atom, and $R^{3c}$ represents any one substituent described in [Table A3] to [Table A11] (hereinafter referred to as "Compound group SX53").

The Compound (L-2), wherein Q represents a group represented by Q52, $R^{3b}$ represents any one substituent described in [Table A3] to [Table A11], and $R^{3c}$ represents a hydrogen atom (hereinafter referred to as "Compound group SX54").

The Compound (L-2), wherein Q represents a group represented by Q52, $R^{3b}$ represents a hydrogen atom, and $R^{3c}$ represents any one substituent described in [Table A3] to [Table A11] (hereinafter referred to as "Compound group SX55").

A compound represented by formula (L-3)

(L-3)

(hereinafter referred to as "Compound (L-3)"), wherein Q represents a group represented by Q11, and $R^1$ represents any one substituent described in [Table A1] or [Table A2](hereinafter referred to as "Compound group SX56").

The Compound (L-3), wherein Q represents a group represented by Q12, and $R^1$ represents any one substituent described in [Table A1] or [Table A2] (hereinafter referred to as "Compound group SX57").

The Compound (L-3), wherein Q represents a group represented by Q13, and $R^1$ represents any one substituent described in [Table A1] or [Table A2] (hereinafter referred to as "Compound group SX58").

The Compound (L-3), wherein Q represents a group represented by Q14, and $R^1$ represents any one substituent described in [Table A1] or [Table A2] (hereinafter referred to as "Compound group SX59").

The Compound (L-3), wherein Q represents a group represented by Q15, and $R^1$ represents any one substituent described in [Table A1] or [Table A2] (hereinafter referred to as "Compound group SX60").

The Compound (L-3), wherein Q represents a group represented by Q16, and $R^1$ represents any one substituent described in [Table A1] or [Table A2] (hereinafter referred to as "Compound group SX61").

The Compound (L-3), wherein Q represents a group represented by Q17, and $R^1$ represents any one substituent described in [Table A1] or [Table A2] (hereinafter referred to as "Compound group SX62").

The Compound (L-3), wherein Q represents a group represented by Q18, and $R^1$ represents any one substituent described in [Table A1] or [Table A2] (hereinafter referred to as "Compound group SX63").

The Compound (L-3), wherein Q represents a group represented by Q19, and $R^1$ represents any one substituent described in [Table A1] or [Table A2] (hereinafter referred to as "Compound group SX64").

The Compound (L-3), wherein Q represents a group represented by Q20, and $R^1$ represents any one substituent described in [Table A1] or [Table A2] (hereinafter referred to as "Compound group SX65").

The Compound (L-3), wherein Q represents a group represented by Q21, and $R^1$ represents any one substituent described in [Table A1] or [Table A2] (hereinafter referred to as "Compound group SX66").

A compound represented by formula (L-4)

(L-4)

(hereinafter referred to as "Compound (L-4)"), wherein Q represents a group represented by Q31, $R^{3b}$ represents any one substituent described in [Table A3] to [Table A11], and $R^{3c}$ represents a hydrogen atom (hereinafter referred to as "Compound group SX67").

The Compound (L-4), wherein Q represents a group represented by Q31, $R^{3b}$ represents a hydrogen atom, and $R^{3c}$ represents any one substituent described in [Table A3] to [Table A11] (hereinafter referred to as "Compound group SX68").

The Compound (L-4), wherein Q represents a group represented by Q32, $R^{3b}$ represents any one substituent described in [Table A3] to [Table A11], and $R^{3c}$ represents a hydrogen atom (hereinafter referred to as "Compound group SX69").

The Compound (L-4), wherein Q represents a group represented by Q32, $R^{3b}$ represents a hydrogen atom, and $R^{3c}$ represents any one substituent described in [Table A3] to [Table A11] (hereinafter referred to as "Compound group SX70").

The Compound (L-4), wherein Q represents a group represented by Q33, $R^{3b}$ represents any one substituent described in [Table A3] to [Table A11], and $R^{3c}$ represents a hydrogen atom (hereinafter referred to as "Compound group SX71").

The Compound (L-4), wherein Q represents a group represented by Q33, $R^{3b}$ represents a hydrogen atom, and $R^{3c}$ represents any one substituent described in [Table A3] to [Table A11] (hereinafter referred to as "Compound group SX72").

The Compound (L-4), wherein Q represents a group represented by Q34, $R^{3b}$ represents any one substituent described in [Table A3] to [Table A11], and $R^{31}$ represents a hydrogen atom (hereinafter referred to as "Compound group SX73").

The Compound (L-4), wherein Q represents a group represented by Q34, $R^{3b}$ represents a hydrogen atom, and $R^{3c}$ represents any one substituent described in [Table A3] to [Table A11] (hereinafter referred to as "Compound group SX74").

The Compound (L-4), wherein Q represents a group represented by Q35, $R^{3b}$ represents any one substituent described in [Table A3] to [Table A11], and $R^{3c}$ represents a hydrogen atom (hereinafter referred to as "Compound group SX75").

The Compound (L-4), wherein Q represents a group represented by Q35, $R^{3b}$ represents a hydrogen atom, and $R^{3c}$ represents any one substituent described in [Table A3] to [Table A11] (hereinafter referred to as "Compound group SX76").

The Compound (L-4), wherein Q represents a group represented by Q36, $R^{3b}$ represents any one substituent described in [Table A3] to [Table A11], and $R^{37}$ represents a hydrogen atom (hereinafter referred to as "Compound group SX77").

The Compound (L-4), wherein Q represents a group represented by Q36, $R^{3b}$ represents a hydrogen atom, and $R^{3c}$ represents any one substituent described in [Table A3] to [Table A11] (hereinafter referred to as "Compound group SX78").

The Compound (L-4), wherein Q represents a group represented by Q37, $R^{3b}$ represents any one substituent described in [Table A3] to [Table A11], and $R^{3c}$ represents a hydrogen atom (hereinafter referred to as "Compound group SX79").

The Compound (L-4), wherein Q represents a group represented by Q37, $R^{3b}$ represents a hydrogen atom, and $R^{3c}$ represents any one substituent described in [Table A3] to [Table A11] (hereinafter referred to as "Compound group SX80").

The Compound (L-4), wherein Q represents a group represented by Q38, $R^{3b}$ represents any one substituent described in [Table A3] to [Table A11], and $R^{31}$ represents a hydrogen atom (hereinafter referred to as "Compound group SX81").

The Compound (L-4), wherein Q represents a group represented by Q38, $R^{3b}$ represents a hydrogen atom, and $R^{3c}$ represents any one substituent described in [Table A3] to [Table A11] (hereinafter referred to as "Compound group SX82").

The Compound (L-4), wherein Q represents a group represented by Q39, $R^{3b}$ represents any one substituent described in [Table A3] to [Table A11], and $R^{31}$ represents a hydrogen atom (hereinafter referred to as "Compound group SX83").

The Compound (L-4), wherein Q represents a group represented by Q39, $R^{3b}$ represents a hydrogen atom, and $R^{3c}$ represents any one substituent described in [Table A3] to [Table A11] (hereinafter referred to as "Compound group SX84").

The Compound (L-4), wherein Q represents a group represented by Q40, $R^{3b}$ represents any one substituent described in [Table A3] to [Table A11], and $R^{3c}$ represents a hydrogen atom (hereinafter referred to as "Compound group SX85").

The Compound (L-4), wherein Q represents a group represented by Q40, $R^{3b}$ represents a hydrogen atom, and $R^{3c}$ represents any one substituent described in [Table A3] to [Table A11] (hereinafter referred to as "Compound group SX86").

The Compound (L-4), wherein Q represents a group represented by Q41, $R^{3b}$ represents any one substituent described in [Table A3] to [Table A11], and $R^{37}$ represents a hydrogen atom (hereinafter referred to as "Compound group SX87").

The Compound (L-4), wherein Q represents a group represented by Q41, $R^{3b}$ represents a hydrogen atom, and $R^{3c}$ represents any one substituent described in [Table A3] to [Table A11] (hereinafter referred to as "Compound group SX88").

The Compound (L-4), wherein Q represents a group represented by Q42, $R^{3b}$ represents any one substituent described in [Table A3] to [Table A11], and $R^{3c}$ represents a hydrogen atom (hereinafter referred to as "Compound group SX89").

The Compound (L-4), wherein Q represents a group represented by Q42, $R^{3b}$ represents a hydrogen atom, and $R^{3c}$ represents any one substituent described in [Table A3] to [Table A11] (hereinafter referred to as "Compound group SX90").

The Compound (L-4), wherein Q represents a group represented by Q43, $R^{3b}$ represents any one substituent described in [Table A3] to [Table A11], and $R^{31}$ represents a hydrogen atom (hereinafter referred to as "Compound group SX91").

The Compound (L-4), wherein Q represents a group represented by Q43, $R^{3b}$ represents a hydrogen atom, and $R^{3c}$ represents any one substituent described in [Table A3] to [Table A11] (hereinafter referred to as "Compound group SX92").

The Compound (L-4), wherein Q represents a group represented by Q44, $R^{3b}$ represents any one substituent described in [Table A3] to [Table A11], and $R^{31}$ represents a hydrogen atom (hereinafter referred to as "Compound group SX93").

The Compound (L-4), wherein Q represents a group represented by Q44, $R^{3b}$ represents a hydrogen atom, and $R^{3c}$ represents any one substituent described in [Table A3] to [Table A11] (hereinafter referred to as "Compound group SX94").

The Compound (L-4), wherein Q represents a group represented by Q45, $R^{3b}$ represents any one substituent described in [Table A3] to [Table A11], and $R^{3c}$ represents a hydrogen atom (hereinafter referred to as "Compound group SX95").

The Compound (L-4), wherein Q represents a group represented by Q45, $R^{3b}$ represents a hydrogen atom, and $R^{3c}$ represents any one substituent described in [Table A3] to [Table A11] (hereinafter referred to as "Compound group SX96").

The Compound (L-4), wherein Q represents a group represented by Q46, $R^{3b}$ represents any one substituent described in [Table A3] to [Table A11], and $R^{37}$ represents a hydrogen atom (hereinafter referred to as "Compound group SX97").

The Compound (L-4), wherein Q represents a group represented by Q46, $R^{3b}$ represents a hydrogen atom, and $R^{3c}$ represents any one substituent described in [Table A3] to [Table A11] (hereinafter referred to as "Compound group SX98").

The Compound (L-4), wherein Q represents a group represented by Q47, $R^{3b}$ represents any one substituent described in [Table A3] to [Table A11], and $R^{3c}$ represents a hydrogen atom (hereinafter referred to as "Compound group SX99").

The Compound (L-4), wherein Q represents a group represented by Q47, $R^{3b}$ represents a hydrogen atom, and $R^{3c}$ represents any one substituent described in [Table A3] to [Table A11] (hereinafter referred to as "Compound group SX100").

The Compound (L-4), wherein Q represents a group represented by Q48, $R^{3b}$ represents any one substituent described in [Table A3] to [Table A11], and $R^1$ represents a hydrogen atom (hereinafter referred to as "Compound group SX101").

The Compound (L-4), wherein Q represents a group represented by Q48, $R^{3b}$ represents a hydrogen atom, and $R^{3c}$ represents any one substituent described in [Table A3] to [Table A11] (hereinafter referred to as "Compound group SX102").

The Compound (L-4), wherein Q represents a group represented by Q49, $R^{3b}$ represents any one substituent described in [Table A3] to [Table A11], and $R^{31}$ represents a hydrogen atom (hereinafter referred to as "Compound group SX103").

The Compound (L-4), wherein Q represents a group represented by Q49, $R^{3b}$ represents a hydrogen atom, and $R^{3c}$ represents any one substituent described in [Table A3] to [Table A11] (hereinafter referred to as "Compound group SX104").

The Compound (L-4), wherein Q represents a group represented by Q50, $R^{3b}$ represents any one substituent described in [Table A3] to [Table A11], and $R^{3c}$ represents a hydrogen atom (hereinafter referred to as "Compound group SX105").

The Compound (L-4), wherein Q represents a group represented by Q50, $R^{3b}$ represents a hydrogen atom, and $R^{3c}$ represents any one substituent described in [Table A3] to [Table A11] (hereinafter referred to as "Compound group SX106").

The Compound (L-4), wherein Q represents a group represented by Q51, $R^{3b}$ represents any one substituent described in [Table A3] to [Table A11], and $R^3$ represents a hydrogen atom (hereinafter referred to as "Compound group SX107").

The Compound (L-4), wherein Q represents a group represented by Q51, $R^{3b}$ represents a hydrogen atom, and $R^{3c}$ represents any one substituent described in [Table A3] to [Table A11] (hereinafter referred to as "Compound group SX108").

The Compound (L-4), wherein Q represents a group represented by Q52, $R^{3b}$ represents any one substituent described in [Table A3] to [Table A11], and $R^{3c}$ represents a hydrogen atom (hereinafter referred to as "Compound group SX109").

The Compound (L-4), wherein Q represents a group represented by Q52, $R^{3b}$ represents a hydrogen atom, and $R^{3c}$ represents any one substituent described in [Table A3] to [Table A11] (hereinafter referred to as "Compound group SX110").

Next, Formulation Examples of the Present compound X are shown below. The "part(s)" represents "part(s) by weight". Also, the expression of "Present compound S" represents the compounds described in the Compound groups SX1 to SX110.

Formulation Example 1

Any one of the Present compound S (10 parts) is mixed with a mixture of xylene (35 parts) and DMF (35 parts), and then polyoxyethylene styryl phenyl ether (14 parts) and calcium dodecylbenzene sulfonate (6 parts) are added thereto, followed by mixing them to obtain each formulation.

Formulation Example 2

Sodium lauryl sulfate (4 parts), calcium lignin sulfonate (2 parts), wet silica (20 parts), and diatomaceous earth (54 parts) are mixed, and further any one of the Present compound S (20 parts) is added thereto, followed by mixing them to obtain each formulation.

Formulation Example 3

To any one of the Present compound S (2 parts) are added wet silica (1 part), calcium lignin sulfonate (2 parts), bentonite (30 parts), and kaolin clay (65 parts), followed by mixing them to obtain a mixture. To the mixture is then added an appropriate amount of water, the resulting mixture is additionally stirred, and subjected to granulation with a granulator and forced-air drying to obtain each formulation.

Formulation Example 4

Any one of the Present compound S (1 part) is mixed with an appropriate amount of acetone, and then wet silica (5 parts), acidic isopropyl phosphate (0.3 part), and kaolin clay (93.7 parts) are added thereto, followed by mixing with stirring thoroughly and removal of acetone from the mixture by evaporation to obtain each formulation.

Formulation Example 5

A mixture of polyoxyethylene alkyl ether sulfate ammonium salt and wet silica (weight ratio of 1:1) (35 parts), any one of the Present compound S (20 parts), and water (45 parts) are thoroughly mixed to obtain each formulation.

Formulation Example 6

Any one of the Present compound S (0.1 part) is mixed with a mixture of xylene (5 parts) and trichloroethane (5 parts), and the resulting mixture is then mixed with kerosene (89.9 parts) to obtain each formulation.

Formulation Example 7

Any one of the Present compound S (10 mg) is mixed with acetone (0.5 mL), and the solution is added dropwise to a solid feed powder for an animal (solid feed powder for rearing and breeding CE-2, manufactured by CLEA Japan, Inc.) (5 g), followed by mixing the resulting mixture uniformly, and then by drying it by evaporation of acetone to obtain each poison bait.

Formulation Example 8

Any one of the Present compound S (0.1 part) and Neothiozole (manufactured by Chuo Kasei Co., Ltd.) (49.9 parts) are placed into an aerosol can. After mounting an aerosol valve, dimethyl ether (25 parts) and LPG (25 parts) are filled, followed by shaking and further mounting an actuator to obtain each oily aerosol.

Formulation Example 9

A mixture of any one of the Present compound S (0.6 part), 2,6-di-tert-butyl-4-methylphenol (0.01 part), xylene (5 parts), kerosene (3.39 parts), and Rheodol (registered trademark) MO-60 (1 part), and distilled water (50 parts) are filled into an aerosol container, and a valve part is attached. Then, LPG (40 parts) is filled therein through the valve to obtain each aqueous aerosol.

Formulation Example 10

Any one of the Present compound S (0.1 g) is mixed with propylene glycol (2 mL), and the resulting solution is impregnated into a ceramic plate having a size of 4.0 cm×4.0 cm and a thickness of 1.2 cm to obtain each thermal smoking agent.

Formulation Example 11

Any one of the Present compound S (5 parts) and ethylene-methyl methacrylate copolymer (the ratio of the methyl methacrylate relative to the total weight of the copolymer: 10% by weight) (95 parts) are melted and kneaded, and the resulting kneaded product is extruded from an extrusion molding machine to obtain each rod-shaped molded product having a length of 15 cm and a diameter of 3 mm.

Formulation Example 12

Any one of the Present compound S (5 parts) and a flexible vinyl chloride resin (95 parts) are melted and kneaded, and the resulting kneaded product is extruded from an extrusion molding machine to obtain each rod-shaped molded product having a length of 15 cm and a diameter of 3 mm.

Formulation Example 13

Any one of the Present compound S (100 mg), lactose (68.75 mg), corn starch (237.5 mg), microcrystalline cellulose (43.75 mg), polyvinylpyrrolidone (18.75 mg), sodium carboxymethyl starch (28.75 mg), and magnesium stearate (2.5 mg) are mixed, and the resulting mixture is compressed to an appropriate size to obtain each tablet.

Formulation Example 14

Any one of the Present compound S (25 mg), lactose (60 mg), corn starch (25 mg), carmellose calcium (6 mg), and an appropriate amount of 5% hydroxypropyl methylcellulose are mixed, and the resulting mixture is filled into a hard shell gelatin capsule or a hydroxypropyl methylcellulose capsule to obtain each capsule.

Formulation Example 15

To any one of the Present compound S (100 mg), fumaric acid (500 mg), sodium chloride (2,000 mg), methylparaben (150 mg), propylparaben (50 mg), granulated sugar (25,000 mg), sorbitol (70% solution) (13,000 mg), Veegum (registered trademark) K (100 mg), perfume (35 mg), and colorant (500 mg) is added distilled water so that the final volume is set to be 100 mL, followed by mixing them to obtain each suspension for oral administration.

Formulation Example 16

Any one of the Present compound S (5 parts) is mixed with an emulsifier (5 parts), benzyl alcohol (3 parts), and propylene glycol (30 parts), and phosphate buffer is added thereto so that the pH of the solution is set to be 6.0 to 6.5, and then water is added thereto as the rest parts to obtain each solution for oral administration.

Formulation Example 17

Aluminum distearate (5 parts) is added to fractional distillated coconut oil (57 parts) and polysorbate 85 (3 parts), and dispersed by heating. The resulting mixture is cooled to room temperature, and saccharin (25 parts) is dispersed in the oil vehicle. Any one of the Present compound S (10 parts) is distributed thereto to obtain each paste-like formulation for oral administration.

Formulation Example 18

Any one of the Present compound S (5 parts) is mixed with a limestone filler (95 parts), followed by a wet granulation of the resulting mixture to obtain each granule for oral administration.

Formulation Example 19

Any one of the Present compound S (5 parts) is mixed with diethylene glycol monoethyl ether (80 parts), propylene carbonate (15 parts) is added thereto, and the resulting mixture is mixed to obtain each spot-on solution.

Formulation Example 20

Any one of the Present compound S (10 parts) is mixed with diethylene glycol monoethyl ether (70 parts), 2-octyldodecanol (20 parts) is added thereto, and the resulting mixture is mixed to obtain each pour-on solution.

Formulation Example 21

Any one of the Present compound S (0.1 part), sodium polyoxyethylene lauryl ether sulfate (25% aqueous solution) (40 parts), lauramidopropyl betaine (5 parts), coconut oil fatty acid ethanolamide (5 parts), carboxyvinyl polymer (0.5 part), and purified water (49.4 parts) are thoroughly mixed to obtain each shampoo formulation.

Formulation Example 22

Any one of the Present compound S (0.15 part), an animal feed (95 parts), and a mixture (4.85 parts) consisting of calcium hydrogen phosphate, diatomaceous earth, Aerosil (registered trademark), and carbonate (or chalk) are mixed with stirring thoroughly to obtain each premix for an animal feed.

Formulation Example 23

Any one of the Present compound S (7.2 g) and Hosco (registered trademark) S-55 (92.8 g) are mixed at 100° C., and the resulting mixture is poured into a suppository mold, followed by performing a cooling solidification to obtain each suppository.

Next, Test Examples are used to show effects of the Present compounds X on harmful arthropods. In the following Test Examples, the tests were carried out at 25° C.

Test Method 1

Each test compound is formulated according to the process described in the Formulation Example 5 to obtain each formulation, and water containing Sindaine (registered trademark) (0.03% by volume) is added thereto to prepare a diluted solution containing a prescribed concentration of each test compound.

Cucumber (*Cucumis sativus*) seedlings (on the developmental stage of the second true leaf) are planted in a container and approximately 30 cotton aphids (*Aphis gossypii*) (all stages of life) are released onto the cucumber seedlings. After 1 day, each of said diluted solutions is sprayed into the seedlings in a ratio of 10 mL/seedling. After additional 5 days, the number of the surviving insects is examined and the controlling value is calculated by the following equation.

Controlling value(%)={1−(Cb×Tai)/(Cai×Tb)}×100 wherein the symbols in the equation represent the following meanings.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group Here the "untreated group" represents a group where a similar treatment procedure to that of the treated group except not using each test compound is done.

Test Example 1-1

When the prescribed concentration was 500 ppm and each of the following Present compounds was used as a test compound to carry out a test according to the Test method 1, each of the following Present compounds showed 90% or greater as the controlling value.

Present compounds: 1, 2, 3, 4, 5, 7, 9, 10, 11, 12, 13, 14, 15, 16, 17, 20, 22, 23, and 25

Test Example 1-2

When the prescribed concentration was 200 ppm and each of the following Present compounds was used as a test compound to carry out a test according to the Test method 1, each of the following Present compounds showed 90% or greater as the controlling value.

Present compounds: 1, 2, 3, 4, 5, 6, 7, 8, 9, 10, 11, 12, 13, 14, 15, 16, 17, 20, 21, 22, 23, 24, and 25

Test Method 2

Each test compound is formulated according to the process described in the Formulation Example 5 to obtain each formulation, and water is added thereto to prepare a diluted solution containing a prescribed concentration of each test compound.

Cucumber seedlings (on the developmental stage of the second true leaf) are planted in a container, and each of said diluted solutions is irrigated into the plant foot in a ratio of 5 mL/seedling. After 7 days, approximately 30 cotton aphids (*Aphis gossypii*) (all stages of life) are released onto the surfaces of leaves of the cucumber seedlings. After additional 6 days, the number of the surviving insects is examined and the controlling value is calculated by the following equation.

Controlling value(%)={1−(Cb×Tai)/(Cai×Tb)}×100 wherein the symbols in the equation represent the following meanings.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group Here the "untreated group" represents a group where a similar treatment procedure to that of the treated group except not using each test compound is done.

Test Example 2

When the prescribed concentration was 1000 ppm and each of the following Present compounds was used as a test compound to carry out a test according to the Test method 2, each of the following Present compounds showed 90% or greater as the controlling value.

Present compounds: 1, 2, 3, 4, 5, 6, 7, 8, 9, 11, 12, 13, 14, 15, 16, 17, 21, and 24

Test Method 3

Each test compound is formulated according to the process described in the Formulation Example 5 to obtain each formulation, and water containing Sindaine (registered trademark) (0.03% by volume) is added thereto to prepare a diluted solution containing a prescribed concentration of each test compound.

Cabbage (*Brassicae oleracea*) seedlings (on the developmental stage of the second to third true leaf) are planted in a container, and each of said diluted solutions is sprayed into the seedlings in a ratio of 20 mL/seedling. Thereafter, the stem and leaf of the seedlings are cut out, and placed into a container lined with a filter paper. Five (5) the 2nd instar larvae of diamondback moth (*Plutella xylostella*) are released into the container. After 5 days, the number of the surviving insects is counted, and the mortality of insects is calculated by the following equation.

Mortality(%)=(1−Number of surviving insects/5)×100

Test Example 3

When the prescribed concentration was 500 ppm and each of the following Present compounds was used as a test compound to carry out a test according to the Test method 3, each of the following Present compounds showed 80% or greater as the mortality.

Present compounds: 2, 4, 5, 7, 9, 10, 11, 12, 13, 14, 15, 16, 17, 20, 22, 23, and 25

Test Method 4

Each test compound is formulated according to the process described in the Formulation Example 5 to obtain each formulation, and water containing a spreader (0.03% by volume) is added thereto to prepare a diluted solution containing a prescribed concentration of each test compound.

Cabbage (*Brassicae oleracea*) seedlings (on the developmental stage of the third to fourth true leaf) are planted in a container, and each of said diluted solutions is sprayed into the seedlings in a ratio of 20 mL/seedling. Thereafter, 10 the 3rd instar larvae of diamondback moth (*Plutella xylostella*) are released into the cabbage seedlings. After 5 days, the number of the surviving insects is counted, and the mortality of insects is calculated by the following equation.

Mortality(%)=(1−Number of surviving insects/10)×100

Test Example 4

When the prescribed concentration was 200 ppm and each of the following Present compounds was used as a test compound to carry out a test according to the Test method 4, each of the following Present compounds showed 90% or greater as the mortality.

Present compounds: 4, 5, 6, 8, 9, 10, 11, 12, 13, 15, 17, 21, 22, 23, 24, and 25

Test Method 5

Each test compound is formulated according to the process described in the Formulation Example 5 to obtain each formulation, and water containing Sindaine (registered trademark) (0.03% by volume) is added thereto to prepare a diluted solution containing a prescribed concentration of each test compound.

Cabbage (*Brassicae oleracea*) seedlings (on the developmental stage of the second to third true leaf) are planted in a container, and each of said diluted solutions is sprayed into the seedlings in a ratio of 20 mL/seedling. Thereafter, the stem and leaf of the seedlings are cut out, and placed into a container lined with a filter paper. Five (5) the 2nd instar larvae of cotton worm (*Spodoptera litura*) are released into the container. After 5 days, the number of the surviving insects is counted, and the mortality of insects is calculated by the following equation.

Mortality(%)=(1−Number of surviving insects/5)×100

Test Example 5

When the prescribed concentration was 500 ppm and each of the following Present compounds was used as a test compound to carry out a test according to the Test method 5, each of the following Present compounds showed 80% or greater as the mortality.

Present compounds: 5, 7, 9, 10, 11, 12, 13, 14, 15, 16, and Test Method 6

Each test compound is dissolved into a mixed solution (50 μL) of polyoxyethylene sorbitan mono-cocoate and acetone (at a volume ratio of polyoxyethylene sorbitan mono-cocoate:acetone=5:95) per 1 mg of the test compound. Water containing Sindaine (registered trademark) (0.03% by volume) is added thereto to prepare a diluted solution containing a prescribed concentration of each test compound.

Young seedlings of corns (*Zea mays*) are immersed into each of said diluted solutions for 30 seconds. Thereafter, two of said seedlings are placed into a petri dish (diameter: 90 mm), and 10 the 2nd instar larvae of western corn rootworm (*Diabrotica virgifera virgifera*) are released into the dish. After 5 days, the number of the dead insects is counted, and the mortality of insects is calculated by the following equation.

Mortality(%)=(Number of dead insects/10)×100

Test Example 6

When the prescribed concentration was 500 ppm and each of the following Present compounds was used as a test compound to carry out a test according to the Test method 6, each of the following Present compounds showed 80% or greater as the mortality.

Present compounds: 4, 5, 8, 9, 10, 14, 15, 16, 17, 21, 23, and 25

Test Method 7

Each test compound is formulated according to the process described in the Formulation Example 5 to obtain each formulation, and water is added thereto to prepare a diluted solution containing a prescribed concentration of each test compound.

A filter paper having a diameter of 5.5 cm is lined with the inside bottom of a cup having a diameter of 5.5 cm, each of said diluted solutions (0.7 mL) is added dropwise on the filter paper, and sucrose (30 mg) is homogeneously placed into said cup as a feed. Ten (10) female adult house flies (*Musca domestica*) are released into said cup, and the cup is covered. After 24 hours, life and death of the house flies are examined, the number of the dead insects is counted, and the mortality of insects is calculated by the following equation.

Mortality(%)=(Number of dead insects/Number of test insects)×100

Test Example 7

When the prescribed concentration was 500 ppm and each of the following Present compounds was used as a test compound to carry out a test according to the Test method 7, each of the following Present compounds showed 100% as the mortality.

Present compounds: 10, 11, 12, and 17

Test Method 8

Each test compound is formulated according to the process described in the Formulation Example 5 to obtain each formulation, and water is added thereto to prepare a diluted solution containing a prescribed concentration of each test compound.

A filter paper having a diameter of 5.5 cm is lined with the inside bottom of a cup having a diameter of 5.5 cm, each of said diluted solutions (0.7 mL) is added dropwise on the filter paper, and sucrose (30 mg) is homogeneously placed into said cup as a feed. Two (2) male adult German cockroaches (*Blattella germanica*) are released into said cup, and the cup is covered. After 6 days, life and death of the German cockroach are examined, the number of the dead insects is counted, and the mortality of insects is calculated by the following equation.

Mortality(%)=(Number of dead insects/Number of test insects)×100

Test Example 8

When the prescribed concentration was 500 ppm and the following Present compound was used as a test compound to carry out a test according to the Test method 8, the following Present compound showed 100% as the mortality.

Present compound: 12

Test Example 9

The Present compound (1 mg) is dissolved into a mixed solution (10 μL) of xylene, DMF, and surfactant (at a volume ratio of xylene:DMF:surfactant=4:4:1), and the resulting solution is diluted with water containing a spreader (0.02% by volume) to prepare a diluted solution A containing a prescribed concentration of the Present compound.

The Present ingredient (1 mg) is dissolved into a mixed solution (10 μL) of xylene, DMF, and surfactant (at a volume ratio of xylene:DMF:surfactant=4:4:1), and the resulting solution is diluted with water containing a spreader (0.02% by volume) to prepare a diluted solution B containing a prescribed concentration of the Present ingredient.

The diluted solution A and the diluted solution B are mixed to prepare a diluted solution C.

A lamina (length: 1.5 cm) of cucumber cotyledon is placed into each well of a 24 well microplate, then two (2) wingless adults and eight (8) larvae of cotton aphids (*Aphis* gossypii) are released into each well, and 20 μL of the diluted solution C is sprayed into each well. Said well is defined as "treated group".

A well into which 20 μL of water containing a spreader (0.02% by volume) instead of the diluted solution C is sprayed is defined as "untreated group".

After the diluted solution C is dried, the upper part of the microplate is covered by a film sheet. After 5 days, the number of the surviving insects in each well is examined.

The controlling value is calculated by the following equation.

Controlling value(%)={1−(Tai)/(Cai)}×100 wherein the symbols in the equation represent the following meanings.

Cai: Number of the surviving insects at the time of the investigation in untreated group;

Tai: Number of the surviving insects at the time of the investigation in treated group Specific examples of the diluted solution C of which the effects can be confirmed in the Test Example 9 include the following 1) to 5).

1) A diluted solution C of any one combination described in the List A, wherein the concentration of the Present compound is 200 ppm and the concentration of the Present ingredient is 2,000 ppm. In the List A, Comp X represents any one compound selected from the Present compounds 1 to 45.

List A:

Comp X+clothianidin; Comp X+thiamethoxam; Comp X+imidacloprid; Comp X+thiacloprid; Comp X+flupyradifurone; Comp X+sulfoxaflor; Comp X+triflumezopyrim; Comp X+dicloromezotiaz; Comp X+beta-cyfluthrin; Comp X+tefluthrin; Comp X+fipronil; Comp X+chlorantraniliprole; Comp X+cyantraniliprole; Comp X+tetraniliprole; Comp X+thiodicarb; Comp X+carbofuran; Comp X+fluxametamide; Comp X+afoxolaner; Comp X+fluralaner; Comp X+broflanilide; Comp X+abamectin; Comp X+fluopyram; Comp X+fluensulfone; Comp X+fluazaindolizine; Comp X+tioxazafen; Comp X+flupyrimin; Comp X+mycorrhizal fungi; Comp X+*Bradyrhizobium japonicum* TA-11; Comp X+*Bacillus firmus*; Comp X+*Bacillus firmus* I-1582; Comp X+*Bacillus amyloliquefaciens*; Comp X+*Bacillus amyloliquefaciens* FZB42; Comp X+*Pasteuria nishizawae*; Comp X+*Pasteuria nishizawae* Pn1; Comp X+*Pasteuria penetrans*; Comp X+tebuconazole; Comp X+prothioconazole; Comp X+metconazole; Comp X+ipconazole; Comp X+triticonazole; Comp X+difenoconazole; Comp X+imazalil; Comp X+triadimenol; Comp X+tetraconazole; Comp X+flutriafol; Comp X+mandestrobin; Comp X+azoxystrobin; Comp X+pyraclostrobin; Comp X+trifloxystrobin; Comp X+fluoxastrobin; Comp X+picoxystrobin; Comp X+fenamidone; Comp X+metalaxyl; Comp X+metalaxyl-M; Comp X+fludioxonil; Comp X+sedaxane; Comp X+penflufen; Comp X+fluxapyroxad; Comp X+benzovindiflupyr; Comp X+boscalid; Comp X+carboxin; Comp X+penthiopyrad; Comp X+flutolanil; Comp X+captan; Comp X+thiram; Comp X+tolclofos-methyl; Comp X+thiabendazole; Comp X+ethaboxam; Comp X+mancozeb; Comp X+picarbutrazox; Comp X+oxathiapiprolin; Comp X+silthiofam; Comp X+inpyrfluxam.

2) A diluted solution C of any one combination described in the List A, wherein the concentration of the Present compound is 200 ppm and the concentration of the Present ingredient is 200 ppm.

3) A diluted solution C of any one combination described in the List A, wherein the concentration of the Present compound is 500 ppm and the concentration of the Present ingredient is 50 ppm.

4) A diluted solution C of any one combination described in the List A, wherein the concentration of the Present compound is 500 ppm and the concentration of the Present ingredient is 5 ppm.

5) A diluted solution C of any one combination described in the List A, wherein the concentration of the Present compound is 500 ppm and the concentration of the Present ingredient is 0.5 ppm.

INDUSTRIAL APPLICABILITY

The Present compounds X have excellent control effects on harmful arthropods.

The invention claimed is:

1. A compound represented by formula (I) or an N-oxide compound thereof,

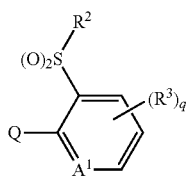

(I)

[wherein:
Q represents a group represented by Q1 or a group represented by Q2;

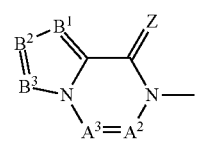

Q1

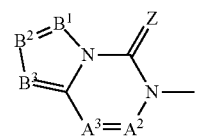

Q2

Z represents an oxygen atom or a sulfur atom;
$A^1$ represents a nitrogen atom or a $CR^5$;
$R^5$ represents a halogen atom or a hydrogen atom;
$A^2$ and $A^3$ represents a combination, which is
a combination wherein $A^2$ represents a $CR^{4a}$ and $A^3$ represents a nitrogen atom or a $CR^{4b}$; or
a combination wherein $A^2$ represents a nitrogen atom and $A^3$ represents a $CR^{4b}$;
$B^1$, $B^2$, and $B^3$ represents a combination, which is
a combination wherein $B^1$ represents a $CR^1$, $B^2$ represents a nitrogen atom or a $CR^{6b}$, and $B^3$ represents a nitrogen atom or a $CR^{6c}$;
a combination wherein $B^1$ represents a nitrogen atom or a $CR^{6a}$, $B^2$ represents a $CR^1$, and $B^3$ represents a nitrogen atom or a $CR^{6c}$; or
a combination wherein $B^1$ represents a nitrogen atom or a $CR^{6a}$, $B^2$ represents a nitrogen atom or a $CR^{6b}$, and $B^3$ represents a $CR^1$;

R¹ represents a C1-C6 chain hydrocarbon group having one or more substituent(s) selected from the group consisting of a cyano group and a halogen atom, a C3-C4 cycloalkyl group optionally having one or more substituent(s) selected from the group consisting of a cyano group and a halogen atom, a —SR⁸, a —S(O)R⁸, a —S(O)₂R⁸, a —OR⁸, or a —OS(O)₂R⁸;

R⁸ represents a C1-C6 chain hydrocarbon group having one or more substituent(s) selected from the group consisting of a cyano group and a halogen atom, or a C3-C4 cycloalkyl group optionally having one or more substituent(s) selected from the group consisting of a cyano group and a halogen atom;

R⁴ᵃ, R⁴ᵇ, R⁶ᵃ, R⁶ᵇ, and R⁶ᶜ are identical to or different from each other, and each represent a C1-C6 chain hydrocarbon group optionally having one or more halogen atom(s), a C3-C7 cycloalkyl group optionally having one or more halogen atom(s), a C1-C6 alkoxy group optionally having one or more halogen atom(s), a —NR⁹R¹⁰, a —C(O)R⁷, a —C(O)OR⁷, a —C(O)NR¹⁹R²⁰, a —NR⁹C(O)R¹⁸, a —NR⁹C(O)OR¹⁸, a —NR⁹C(O)NR¹⁹R²⁰, a cyano group, a halogen atom, or a hydrogen atom;

R⁹ and R¹⁹ are identical to or different from each other, and each represent a C1-C6 chain hydrocarbon group optionally having one or more halogen atom(s), or a hydrogen atom;

R¹⁰ represents a C1-C6 chain hydrocarbon group optionally having one or more substituent(s) selected from Group F, a C3-C7 cycloalkyl group optionally having one or more substituent(s) selected from Group J, a C3-C7 cycloalkenyl group optionally having one or more substituent(s) selected from Group J, a phenyl group optionally having one or more substituent(s) selected from Group D, a 6 membered aromatic heterocyclic group optionally having one or more substituent(s) selected from Group D, a hydrogen atom, or a —S(O)₂R²¹;

R²¹ represents a C1-C6 chain hydrocarbon group optionally having one or more halogen atom(s), a C3-C7 cycloalkyl group optionally having one or more halogen atom(s), or a phenyl group optionally having one or more substituent(s) selected from Group D;

R⁷, R¹⁸, and R²⁰ are identical to or different from each other, and each represent a C1-C6 chain hydrocarbon group optionally having one or more substituent(s) selected from Group F, a C3-C7 cycloalkyl group optionally having one or more substituent(s) selected from Group J, or a hydrogen atom;

R² represents a C1-C6 chain hydrocarbon group optionally substituted with one or more halogen atom(s), a cyclopropyl group, or a cyclopropylmethyl group;

n represents 0, 1, or 2;

R³ represents a C1-C6 chain hydrocarbon group optionally having one or more substituent(s) selected from Group B, a C3-C7 cycloalkyl group optionally having one or more substituent(s) selected from Group E, a C3-C7 cycloalkenyl group optionally having one or more substituent(s) selected from Group J, a phenyl group optionally having one or more substituent(s) selected from Group H, a 5 or 6 membered aromatic heterocyclic group optionally having one or more substituent(s) selected from Group H, —OR¹², a —NR¹¹R¹², a —NR¹¹ᵃR¹²ᵃ, a —NR²⁴NR¹¹R¹², a —NR²⁴OR¹¹, a —NR¹¹C(O)R¹³, a —NR²⁴NR¹¹C(O)R¹³, a —NR¹¹C(O)OR¹⁴, a —NR²⁴NR¹¹C(O)OR¹⁴, a —NR¹¹C(O)NR¹⁵ᵃR¹⁶ᵃ, a —NR²⁴NR¹¹C(O)NR¹⁵ᵃR¹⁶ᵃ, a —N=CR²⁴NR¹⁵ᵃR¹⁶ᵃ, a —N=S(O)ₓR¹⁵R¹⁶, a —C(O)R¹³, a —C(O)OR¹⁷, a —C(O)NR¹⁵ᵃR¹⁶ᵃ, a —C(O)NR¹¹S(O)₂R²³, a —CR²⁴=NOR¹⁷, a —NR¹¹CR²⁴=NOR¹⁷, a cyano group, a nitro group, or a halogen atom;

q represents 0, 1, 2, or 3, wherein when q represents 2 or 3, two or three R³ may be identical to or different from each other;

When two R³ are adjacent with each other, the two R³ may be combined with the two carbon atoms to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring {wherein said benzene ring, said pyrrole ring, said furan ring, said thiophene ring, said pyrazole ring, said imidazole ring, said triazole ring, said oxazole ring, said isoxazole ring, said thiazole ring, said pyridine ring, said pyridazine ring, said pyrimidine ring, and said pyrazine ring may optionally have one or more substituent(s) selected from Group H};

R¹⁷ represents a C1-C6 chain hydrocarbon group optionally having one or more halogen atom(s), a phenyl group optionally having one or more substituent(s) selected from Group D, or a hydrogen atom;

R¹¹, R¹⁵ᵃ and R²⁴ are identical to or different from each other, and each represent a C1-C6 chain hydrocarbon group optionally having one or more halogen atom(s), or a hydrogen atom;

R¹² represents a C1-C6 chain hydrocarbon group optionally having one or more substituent(s) selected from Group F, a C3-C7 cycloalkyl group optionally having one or more substituent(s) selected from Group J, a C3-C7 cycloalkenyl group optionally having one or more substituent(s) selected from Group J, a phenyl group optionally having one or more substituent(s) selected from Group D, a 6 membered aromatic heterocyclic group optionally having one or more substituent(s) selected from Group D, a hydrogen atom, or a —S(O)₂R²³;

R²³ represents a C1-C6 chain hydrocarbon group optionally having one or more halogen atom(s), a C3-C7 cycloalkyl group optionally having one or more halogen atom(s), or a phenyl group optionally having one or more substituent(s) selected from Group D;

R¹¹ᵃ and R¹²ᵃ may be combined with the nitrogen atom to which they are attached to form a 3-7 membered nonaromatic heterocyclic group optionally having one or more substituent(s) selected from Group E;

R¹³ represents a C1-C6 chain hydrocarbon group optionally having one or more halogen atom(s), a C3-C7 cycloalkyl group optionally having one or more halogen atom(s), a (C3-C6 cycloalkyl)C1-C3 an alkyl group optionally having one or more halogen atom(s), a phenyl group optionally having one or more substituent(s) selected from Group D, a 5 or 6 membered aromatic heterocyclic group optionally having one or more substituent(s) selected from Group D, or a hydrogen atom;

R¹⁴ represents a C1-C6 chain hydrocarbon group optionally having one or more halogen atom(s), a C3-C7 cycloalkyl group optionally having one or more halogen atom(s), a (C3-C6 cycloalkyl)C1-C3 an alkyl group optionally having one or more halogen atom(s), or a (phenyl optionally having one or more substituent(s) selected from Group D)C1-C3 an alkyl group;

$R^{15}$ and $R^{16}$ are identical to or different from each other, and each represent a C1-C6 an alkyl group optionally having one or more halogen atom(s);

$R^{16a}$ represents a C1-C6 chain hydrocarbon group optionally having one or more substituent(s) selected from Group F, a C3-C7 cycloalkyl group optionally having one or more substituent(s) selected from Group J, or a hydrogen atom; and x represents 0 or 1;

Group B: a group consisting of a C1-C6 alkoxy group optionally having one or more halogen atom(s), a C3-C6 alkenyloxy group optionally having one or more halogen atom(s), a C3-C6 alkynyloxy group optionally having one or more halogen atom(s), a C1-C6 alkylsulfanyl group optionally having one or more halogen atom(s), a C1-C6 alkylsulfinyl group optionally having one or more halogen atom(s), a C1-C6 alkylsulfonyl group optionally having one or more halogen atom(s), a C3-C6 cycloalkyl group optionally having one or more halogen atom(s), a (C1-C6 alkyl optionally having one or more halogen atom(s))amino group, a di(C1-C4 alkyl)amino group optionally having one or more halogen atom(s), a C2-C6 alkylcarbonyl group optionally having one or more halogen atom(s), a C2-C6 alkoxycarbonyl group optionally having one or more halogen atom(s), a C2-C6 alkoxycarbonyloxy group optionally having one or more halogen atom(s), an aminocarbonyl group, a (C1-C6 alkyl optionally having one or more halogen atom(s))aminocarbonyl group, a (di(C1-C4 alkyl)amino optionally having one or more halogen atom(s))carbonyl group, a (C2-C6 alkoxycarbonyl optionally having one or more halogen atom(s)) amino group, a (C2-C6 alkoxycarbonyl)(C1-C6 alkyl) amino group optionally having one or more halogen atom(s), a cyano group, an amino group, a nitro group, a hydroxy group, and a halogen atom;

Group D; a group consisting of a C1-C6 chain hydrocarbon group optionally having one or more halogen atom(s), a C1-C6 alkoxy group optionally having one or more halogen atom(s), a C3-C6 alkenyloxy group optionally having one or more halogen atom(s), a C3-C6 alkynyloxy group optionally having one or more halogen atom(s), a C1-C6 alkylsulfanyl group optionally having one or more halogen atom(s), a C1-C6 alkylsulfinyl group optionally having one or more halogen atom(s), a C1-C6 alkylsulfonyl group optionally having one or more halogen atom(s), a C3-C6 cycloalkyl group optionally having one or more halogen atom(s), a (C1-C6 alkyl optionally having one or more halogen atom(s))amino group, a di(C1-C4 alkyl)amino group optionally having one or more halogen atom(s), a C2-C6 alkylcarbonyl group optionally having one or more halogen atom(s), a C2-C6 alkoxycarbonyl group optionally having one or more halogen atom(s), a C2-C6 alkoxycarbonyloxy group optionally having one or more halogen atom(s), an aminocarbonyl group, a (C1-C6 alkyl optionally having one or more halogen atom(s))aminocarbonyl group, a (di(C1-C4 alkyl)amino optionally having one or more halogen atom(s))carbonyl group, a (C2-C6 alkoxycarbonyl optionally having one or more halogen atom(s))amino group, a (C2-C6 alkoxycarbonyl)(C1-C6 alkyl)amino group optionally having one or more halogen atom(s), a cyano group, an amino group, a nitro group, a hydroxy group, and a halogen atom;

Group E: a group consisting of a C1-C6 chain hydrocarbon group optionally having one or more halogen atom(s), a C1-C6 alkoxy group optionally having one or more halogen atom(s), a C3-C6 alkenyloxy group optionally having one or more halogen atom(s), a C3-C6 alkynyloxy group optionally having one or more halogen atom(s), a (C1-C6 alkyl optionally having one or more halogen atom(s))amino group, a di(C1-C4 alkyl)amino group optionally having one or more halogen atom(s), a C2-C6 alkylcarbonyl group optionally having one or more halogen atom(s), a C2-C6 alkoxycarbonyl group optionally having one or more halogen atom(s), a C2-C6 alkoxycarbonyloxy group optionally having one or more halogen atom(s), an aminocarbonyl group, a (C1-C6 alkyl optionally having one or more halogen atom(s))aminocarbonyl group, a (di(C1-C4 alkyl)amino optionally having one or more halogen atom(s))carbonyl group, a (C2-C6 alkoxycarbonyl optionally having one or more halogen atom(s)) amino group, a (C2-C6 alkoxycarbonyl)(C1-C6 alkyl) amino group optionally having one or more halogen atom(s), a cyano group, an amino group, a nitro group, a hydroxy group, an oxo group, and a halogen atom;

Group F: a group consisting of a C3-C6 cycloalkyl group optionally having one or more halogen atom(s), a phenyl group optionally having one or more substituent(s) selected from Group D, a 5 or 6 membered aromatic heterocyclic group optionally having one or more substituent(s) selected from Group D, a C1-C6 alkoxy group optionally having one or more halogen atom(s), a (C1-C6 alkyl optionally having one or more halogen atom(s))amino group, a di(C1-C4 alkyl)amino group optionally having one or more halogen atom(s), a cyano group, an amino group, a nitro group, a hydroxy group, and a halogen atom;

Group H: a group consisting of a C1-C6 chain hydrocarbon group optionally having one or more halogen atom(s), a C3-C6 cycloalkyl group optionally having one or more halogen atom(s), a phenyl group optionally having one or more substituent(s) selected from Group D, a 5 or 6 membered aromatic heterocyclic group optionally having one or more substituent(s) selected from Group D, a C1-C6 alkoxy group optionally having one or more halogen atom(s), a (C1-C6 alkyl optionally having one or more halogen atom(s))amino group, a di(C1-C4 alkyl)amino group optionally having one or more halogen atom(s), a C2-C6 alkylcarbonyl group optionally having one or more halogen atom(s), a C2-C6 alkoxycarbonyl group optionally having one or more halogen atom(s), a C2-C6 alkoxycarbonyloxy group optionally having one or more halogen atom(s), an aminocarbonyl group, a (C1-C6 alkyl optionally having one or more halogen atom(s))aminocarbonyl group, a (di(C1-C4 alkyl)amino optionally having one or more halogen atom(s))carbonyl group, a (C2-C6 alkoxycarbonyl optionally having one or more halogen atom(s))amino group, a (C2-C6 alkoxycarbonyl)(C1-C6 alkyl)amino group optionally having one or more halogen atom(s), a cyano group, an amino group, a nitro group, a hydroxy group, and a halogen atom;

Group J: a group consisting of a C1-C6 an alkyl group optionally having one or more halogen atom(s), a C1-C6 alkoxy group optionally having one or more halogen atom(s), a C2-C6 alkoxycarbonyl group optionally having one or more halogen atom(s), an amino group, a cyano group, and a halogen atom] and a halogen atom].

2. The compound represented by formula (I) according to claim 1.

3. The compound according to claim 1, wherein $A^1$ represents a CH.

4. The compound according to claim 1, wherein $A^1$ represents a nitrogen atom.

5. The compound according to claim 1, wherein Q represents the group represented by Q1.

6. The compound according to claim 1, wherein Q represents the group represented by Q2.

7. The compound according to claim 1, wherein $R^1$ represents a C1-C6 an alkyl group having one or more substituent(s) selected from the group consisting of a cyano group and a halogen atom, a cyclopropyl group optionally having one or more substituent(s) selected from the group consisting of a cyano group and a halogen atom, or a —OS(O)$_2$R$^8$.

8. The compound according to claim 1, wherein $R^3$ represents a C1-C6 an alkyl group optionally having one or more substituent(s) selected from Group B, a C3-C7 cycloalkyl group optionally having one or more substituent(s) selected from Group E, a phenyl group optionally having one or more substituent(s) selected from Group J, a 5 membered aromatic heterocyclic group comprising 1 to 4 nitrogen atom(s) optionally having one or more substituent(s) selected from Group J, a 6 membered aromatic heterocyclic group optionally having one or more substituent(s) selected from Group J, a —OR$^{12}$, a —NR$^{11}$R$^{12}$, a —NR$^{11}$C(O)OR$^{14}$, or a halogen atom.

9. The compound according to claim 1, wherein $R^2$ represents an ethyl group.

10. The compound according to claim 1, wherein Z represents an oxygen atom.

11. A composition for controlling a harmful arthropod comprising the compound according to claim 1 and an inert carrier.

12. A method for controlling a harmful arthropod which comprises applying an effective amount of the compound according to claim 1 to a harmful arthropod or a habitat where a harmful arthropod lives.

13. A composition comprising one or more ingredient(s) selected from the group consisting of Group (a) and Group (b), and the compound according to claim 1:
    Group (a): a group consisting of insecticidal active ingredients, miticidal active ingredients, and nematicidal active ingredients;
    Group (b): fungicidal active ingredients.

14. A method for controlling a harmful arthropod which comprises applying an effective amount of the composition according to claim 13 to a harmful arthropod or a habitat where a harmful arthropod lives.

15. A seed or a vegetative reproduction organ holding an effective amount of the compound according to claim 1.

16. A seed or a vegetative reproduction organ holding an effective amount of the composition according to claim 13.

* * * * *